(12) United States Patent
Chen et al.

(10) Patent No.: US 8,980,909 B2
(45) Date of Patent: Mar. 17, 2015

(54) HDAC INHIBITING DERIVATIVES OF CAMPTOTHECIN

(75) Inventors: Yi Chen, Pleasanton, CA (US); Yu Chen, San Jose, CA (US)

(73) Assignee: Crystal Biopharmaceutical LLC, Wyoming, DE (US)

( * ) Notice: Subject to any disclaimer, the term of this patent is extended or adjusted under 35 U.S.C. 154(b) by 0 days.

(21) Appl. No.: 13/977,413

(22) PCT Filed: Jan. 6, 2012

(86) PCT No.: PCT/US2012/020398
§ 371 (c)(1),
(2), (4) Date: Jun. 28, 2013

(87) PCT Pub. No.: WO2012/096832
PCT Pub. Date: Jul. 19, 2012

(65) Prior Publication Data
US 2013/0281402 A1    Oct. 24, 2013

Related U.S. Application Data

(60) Provisional application No. 61/431,842, filed on Jan. 12, 2011, provisional application No. 61/561,243, filed on Nov. 17, 2011.

(51) Int. Cl.
| | | |
|---|---|---|
| *A61K 31/44* | (2006.01) | |
| *A01N 43/42* | (2006.01) | |
| *C07D 491/22* | (2006.01) | |
| *A61K 31/4745* | (2006.01) | |
| *A61K 31/496* | (2006.01) | |
| *A61K 31/506* | (2006.01) | |
| *A61K 31/695* | (2006.01) | |
| *A61K 45/06* | (2006.01) | |
| *C07F 7/10* | (2006.01) | |

(52) U.S. Cl.
CPC .......... *C07D 491/22* (2013.01); *A61K 31/4745* (2013.01); *A61K 31/496* (2013.01); *A61K 31/506* (2013.01); *A61K 31/695* (2013.01); *A61K 45/06* (2013.01); *C07F 7/10* (2013.01)
USPC ................ 514/283; 514/279; 514/253.02

(58) Field of Classification Search
CPC ............ A61K 31/4745; A61K 31/496; A61K 31/506; A61K 45/06
USPC ........... 514/252.11, 252.18, 253.02, 279, 283
See application file for complete search history.

(56) References Cited

U.S. PATENT DOCUMENTS

| | | | | |
|---|---|---|---|---|
| 8,101,616 | B2 * | 1/2012 | Angibaud et al. | ........ 514/252.14 |
| 8,163,765 | B2 * | 4/2012 | Angibaud et al. | ............ 514/275 |
| 8,609,864 | B2 * | 12/2013 | Chen et al. | ................. 548/309.7 |
| 2007/0123580 | A1 | 5/2007 | Atadja et al. | |
| 2009/0325996 | A1 | 12/2009 | Lu et al. | |
| 2010/0016435 | A1 | 1/2010 | White et al. | |

FOREIGN PATENT DOCUMENTS

| | | |
|---|---|---|
| EP | 0540099 B1 | 4/1996 |
| KR | 10-0246154 B1 | 4/2000 |

OTHER PUBLICATIONS

Noureen et al., "Ligand based pharmacophore modelling of anticancer histone deacetylase inhibitors", Jun. 21, 2010, African Journal of Biotechnology, vol. 9(25), pp. 3923-3931.*
Bailly et al., "The Camptothecin-Resistant Topoisomerase I Mutant F361S Is Cross-Resistant to Antitumor Rebeccamycin Derivatives. A Model for Topoisomerase I Inhibition by Indolocarbazoles", 1999, Biochemistry, vol. 38, No. 27, pp. 8605-8611.*
Beretta et al., "Biological Properties of IDN5174, a New Synthetic Camptothecin with the Open Lactone Ring," *Cancer Res.*, 66:10976-10982 (2006).
Bhatt et al., "Synthesis and in Vivo Antitumor Activity of Poly(L-glutamic acid) Conjugates of 20(S)-Camptothecin," *J. Med. Chem.*, 46(1):190-193 (2003).
Cai et al, "Discovery of 7-(4-(3-Ethynylphenylamino)-7-methoxyquinazolin-6-yloxy)-N-hydroxyheptanamide (CUDC-101) as a Potent Multi-Acting HDAC, EGFR, and HER2 Inhibitor for the Treatment of Cancer," *J. Med. Chem.*, 53(5):2000-2009 (2010) doi: 10.1021/jm901453q.
Huang et al., "Chimmitecan, a Novel 9-Substituted Camptothecin, with Improved Anticancer Pharmacologic Profiles In vitro and In vivo," *Clin. Cancer Res.*, 13(4):1298-1307 (2007).
Koster et al., "Antitumour drugs impede DNA uncoiling by topoisomerase I," *Nature*, 448:213-217 (2007).
Kurtzberg et al., "Genz-644282, a Novel Non-Camptothecin Topoisomerase I Inhibitor for Cancer Treatment," *Clin. Cancer Res.*, 17(9):2777-2787 (2011).
Lorence et al., "Camptothecin, over four decades of surprising findings," *Phytochem.*, 65:2735-2749 (2004).
Luo et al., "Potent antitumor activity of 10-methoxy-9-nitrocamptothecin," *Mol. Cancer Ther.*, (4):962-968 (2006).
Marks and Xu, "Histone deacetylase inhibitors: potential in cancer therapy," *J. Cell. Biochem.*, 107:600-608 (2009).
Marks, "Discovery and development of SAHA as an anticancer agent," *Oncogene*, 26(9):1351-1356 (2007).
Moradei, "Histone Deacetylase Inhibitors: Latest Developments, Trends and Prospects," *Curr. Med. Chem. Anticancer Agents*, 5(5):529-560 (2005).

(Continued)

*Primary Examiner* — My-Chau T Tran
(74) *Attorney, Agent, or Firm* — McCarter & English, LLP; Elizabeth A. Hanley, Esq.; Yu Lu

(57) ABSTRACT

The disclosure includes hydroxamic compounds of Formula I: (Formula I) wherein Z, L, $R_1$, $R_2$, and $R_3$ are defined herein. Also disclosed is a method for treating a neoplastic disease or an immune disease with these compounds.

15 Claims, No Drawings

(56) References Cited

OTHER PUBLICATIONS

Okuno et al., "Complete Regression of Xenografted Human Carcinomas by Camptothecin Analogue-Carboxymethyl Dextran Conjugate (T-0128)," *Cancer Res.*, 60(11):2988-2995 (2000).

Pommier, "Topoisomerase I inhibitors: camptothecins and beyond," *Nat. Rev. Cancer*, 6(10):789-802 (2006).

Pratesi et al., "Pattern of Antitumor Activity of a Novel Camptothecin, ST1481, in a Large Panel of Human Tumor Xenografts," *Clin. Cancer Res.*, 8(12):3904-3909 (2002).

Sapra et al., "Novel Delivery of SN38 Markedly Inhibits Tumor Growth in Xenografts, Including a Camptothecin-11-Refractory Model," *Clin. Cancer Res.*, 14(6):1888-1896 (2008).

Schluep et al., "Preclinical Efficacy of the Camptothecin-Polymer Conjugate IT-101 in Multiple Cancer Models," *Clin. Cancer Res.*, 12(5):1606-1614 (2006).

Ulukan and Swaan, "Camptothecins, A Review of Their Chemotherapeutic Potential," *Drugs*, 62(14):2039-2057 (2002).

Veltkamp et al., "Clinical and Pharmacologic Study of the Novel Prodrug Delimotecan (MEN 4901/T-0128) in Patients with Solid Tumors," *Clin. Cancer Res.*, 14(22):7535-7544 (2008).

Walsh et al., "Pharmacokinetics and Antitumor Efficacy of XMT-1001, a Novel, Polymeric Topoisomerase I Inhibitor, in Mice Bearing HT-29 Human Colon Carcinoma Xenografts," *Clin. Cancer Res.*, 18(9):2591-602 (2012).

Wang, "Toward Selective Histone Deacetylase inhibitor Design: Homology Modeling, Docking Studies, and Molecular Dynamics Simulations of Human Class I histone Deacetylases," *J. Med. Chem.*, 48(22):6936-6947 (2005).

Xie et al., "Quantitative Structure-Activity Relationship Study of Histone Deacetylase Inhibitors," *Curr. Med. Chem. Anticancer Agents*, 4(3):273-299 (2004).

English abstract of KR 10-0246154.

\* cited by examiner

HDAC INHIBITING DERIVATIVES OF CAMPTOTHECIN

RELATED APPLICATIONS

This application is a U.S. national stage application filed under 35 U.S.C. §371, which is based on International Application No. PCT/US2012/020398, filed on Jan. 6, 2012, which claims the benefit of the filing dates of U.S. Provisional Application No. 61/431,842, filed on Jan. 12, 2011, and U.S. Provisional Application No. 61/561,243, filed on Nov. 17, 2011. The entire contents of each of the above applications are incorporated herein by reference.

BACKGROUND

Cancer is one of the most life threatening diseases in which cells in a part of the body experience out-of-control growth. According to the latest data from American Cancer Society, cancer is the $2^{nd}$ leading cause of death in the USA (second only to heart disease) and claimed more than 550,000 lives in 2011. In fact, it is estimated that 50% of all men and 33% of all women living in the United States will develop some type of cancer in their lifetime. Therefore cancer constitutes a major public health burden and represents a significant cost in the United States. For decades, surgery, chemotherapy, and radiation were the established treatments for various cancers. Patients usually receive a combination of these treatments depending on the type and extent of the disease. But chemotherapy is most important treatment option when other treatments are impossible.

Topoisomerase inhibitors (also commonly referred as topoisomerase poisons) are one of the most important chemotherapy for cancer treatment. Topoisomerases are enzymes that regulate the topology of DNA by actions such as breaking, relaxing, passing, and rejoining strands of DNA in cells [Yves Pommie, *Nature Reviews Cancer*, 2006, 6, 789-802]. The mammalian genome encodes seven topoisomerase genes: four that encode type I topoisomerases and three that encode type II topoisomerases (TOP2alpha, TOP2beta, and SPO11). The 4 mammalian type I topoisomerase genes include nuclear topoisomerase I (generally abbreviated TOP1), the mitochondrial topoisomerase I (TOP1MT) gene and two genes that encode TOP3alpha and TOP3beta. The type I topoisomerases have been subdivided into two groups, type IA and IB, on the basis of the side of the DNA break to which the enzyme becomes covalently bound as it forms its catalytic tyrosyl-DNA cleavage intermediate, referred to as the cleavage complex. Top3 enzymes and bacterial TOP1 belong to the type IA group, as they form 5'-DNA tyrosyl adducts similar to the type II topoisomerases. TOP1 and TOP1mt belong to the type IB group, are the only known enzymes that form 3'-phosphotyrosyl bonds in eukaryotic cells. Topoisomerase has held the great interest of cancer researchers owing to the discovery that it is targeted by active anticancer drugs, notably topotecan, irinotecan, mitoxantrone, etoposide, doxorubicin, and so on.

Camptothecin, a cytotoxic quinoline alkaloid, is a natural product which inhibits the DNA enzyme topoisomerase I. Camptothecin was first isolated from the bark of the Chinese tree, camptotheca acuminata. It was discovered and developed by the US National Cancer Institute (NCI) at about the same time and by the same groups that were also working on paclitaxel (Taxol). Camptothecin binds to the topo I and DNA complex (the covalent complex) resulting in a ternary complex, and thereby stabilizing it. This prevents DNA re-ligation and therefore causes DNA damage which results in apoptosis. Camptothecin showed remarkable anticancer activity in preliminary clinical trials in the mid 1970s, but also low solubility and high adverse drug reaction. Because of these disadvantages, synthetic and medicinal chemists have synthesized many derivatives of Camptothecin to increase the benefits of the chemical, with good results. Two semisynthetic camptothecin derivatives have been approved by US FDA for cancer chemotherapy: topotecan and irinotecan. Topotecan is the water-soluble semisynthetic derivative of camptothecin and was approved to treat ovarian cancer ($2^{nd}$ line), cervical cancer ($2^{nd}$ line), and small cell lung cancer ($2^{nd}$ line). Irinotecan was approved as the first line treatment with 5-FU and Leucovorin for colon cancer. Some of the camptothecin derivatives are shown as following:

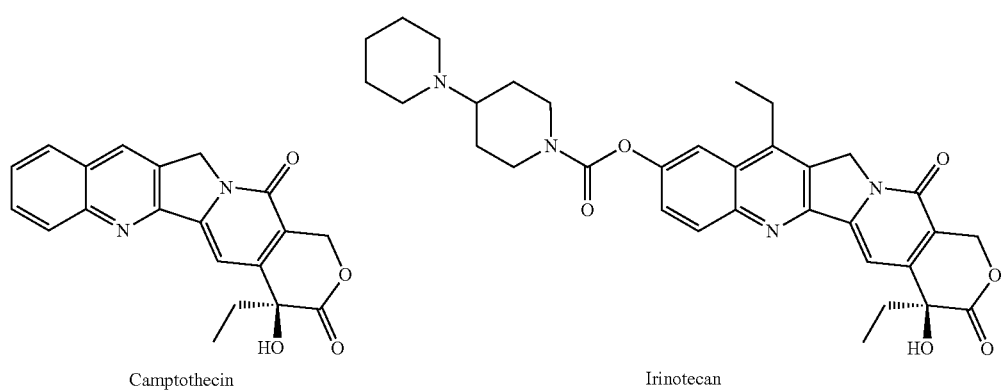

Camptothecin           Irinotecan

-continued
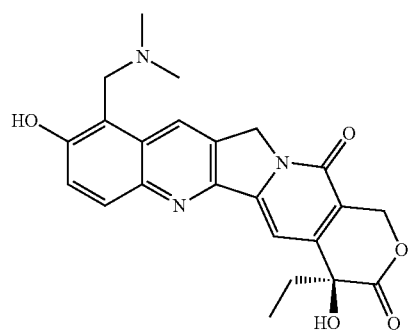
Topotecan
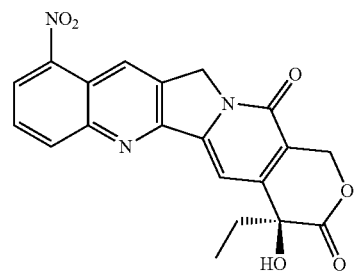
Rubitecan
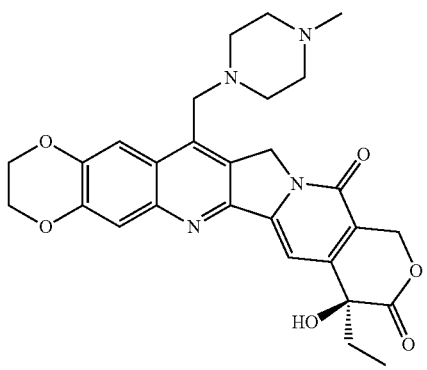
Lurtotecan
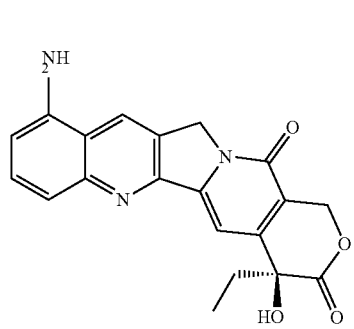
9-AC
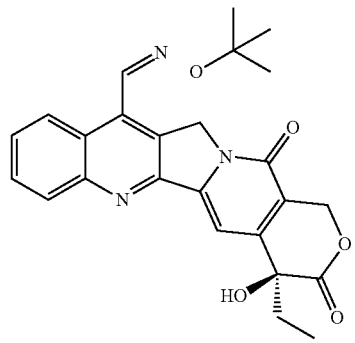
Gimatecan
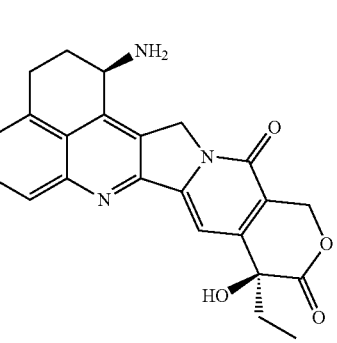
Exatecan
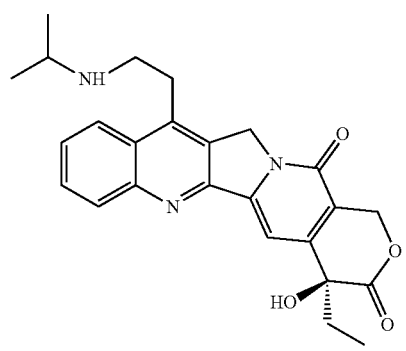
Belotecan
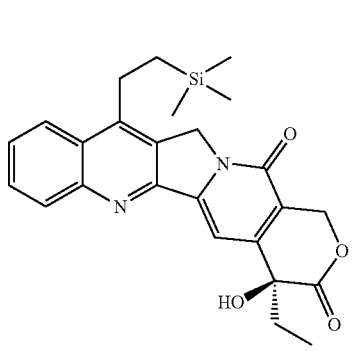
Karenitecin
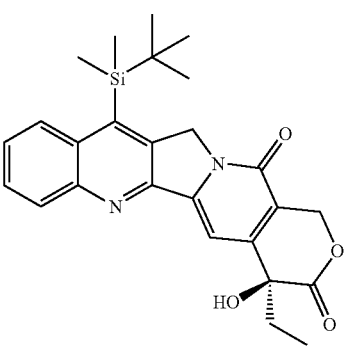
Silatecan
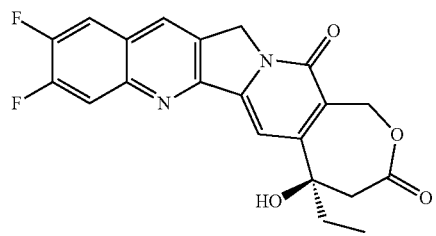
Diflomotecan -continued

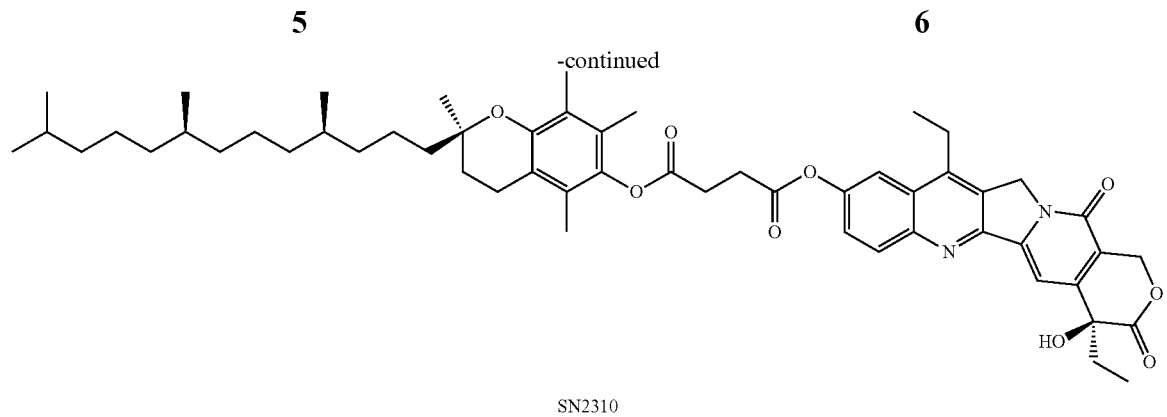

CRLX101 (Phase II)     EZN2208 (Phase II)
(Polymer-CPT Conjugate) (structure not available)

SN2310

Although the conventional camptothecin derivatives have made a significant contribution to cancer treatment, the dose-limiting toxicities and drug resistance remain significant hurdles in the use of these drugs.

In recent years, histone deacetylases (HDAC) has emerged as an important disease target for cancer treatment [Minucci, S. et al., *Nat Rev Cancer* 2006, 6, 38-51]. The human HDAC enzymes have 18 isoforms grouped into Class I-IV according to their sequence homology. Class I, II and IV, commonly referred to as the classical HDACs, are comprised of 11 family members. Class III HDACs consists of 7 enzymes and they are distinct from other HDAC family members, therefore are given a unique term sirtuins. The major difference between classical HDACs and sirtuins reside on their catalytic mechanisms. Classical HDAC contains a catalytic pocket with a $Zn^{2+}$ ion at its base that can be inhibited by $Zn^{2+}$ chelating compound. In contrary, all sirtuins are using $NAD^+$ as cofactor in their deacetylase action.

The inhibition of HDAC enzyme leads to histone acetylation which is associated with the remodelling of chromatin and plays a key role in the epigenetic regulation of gene expression. In addition, HDAC inhibitors have been shown to evoke the acetylation of many important non-histone proteins such as HSP90, alpha-tubulin, Ku-70, Bcl-6, importin, cortactin, p53, STAT1, E2F1, GATA-1 and NF-kB, which can alter many important signaling networks related to cancer treatment. The underlying mechanism of action of HDAC inhibitors includes the differentiation, cell cycle arrest, inhibition of DNA repair, induction of apoptosis, upregulation of tumor suppressors, down regulation of growth factors, oxidative stress and autophagy. In the last decade, a large number of structurally diverse HDAC inhibitors have been identified and at least 12 HDAC inhibitors are currently in human clinical trials for cancer treatments, including short-chain fatty acid (valproic acid), hydroxamates (SAHA, LBH589, PXD101, JNJ-26481585, ITF2357, CUDC-101), cyclic tetrapeptides (FK-228), benzamide (MS-275), and several other compounds (CHR-3996, 4SC-201, SB939). Among them, SAHA and FK-228 has been approved by the US FDA for the treatment of advanced cutaneous T-cell lymphoma.

Certain HDAC inhibitors and camptothecin derivatives (such as Topotecan, Irinotecan) synergistically block cell proliferation when used in combination (Bruzzese et al, Mol Cancer Ther. 2009 November; 8(11):3075-87; Sarcar B, et al, J. Neurooncol. 2010, September; 99(2):201-7; Sato A, et al. Oncol Res. 2011; 19(5):217-23).

SUMMARY OF THE INVENTION

The present invention relates to a novel class of rationally designed HDAC-inhibiting semisynthetic derivatives of camptothecin. More specifically, the present invention relates to a novel class of successfully designed dual-functional semisynthetic Camptothecin/HDAC inhibitors, in which the hydroxamic acid pharmacophore functionally capable of inhibiting HDAC is covalently linked to the camptothecin pharmacophore. The single dual-functional molecule of the invention not only attacks the cancer cells from two distinct pathway simultaneously (HDAC pathway and topoisomerase pathway), but also improves drug efficacy of the conventional camptothecin without increasing its dose-limiting toxicities. Thus, the compounds of the present invention may be useful in treating a patient having a tumor, such as one treatable by the camptothecin family of chemotherapeutic drugs and/or the HDAC inhibitors. The compounds of the invention may additionally be useful in the prevention and treatment of an immune disease.

Thus, in one aspect, this invention relates to an anti-cancer agent (e.g., a molecule) simultaneously containing a hydroxamic acid pharmacophore capable of inhibiting histone deacetylases (HDAC) and a pharmacophore capable of inhibiting topoisomerases.

In certain embodiments, the pharmacophore capable of inhibiting topoisomerases (e.g., topoisomerase I) is a camptothecin pharmacophore.

In certain embodiments, the agent is a hydroxamic compound of Formula I:

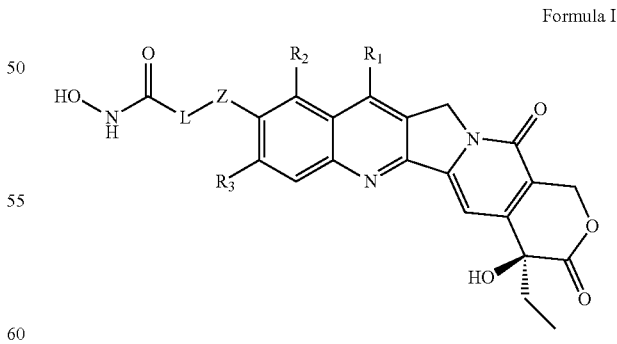

Formula I

In certain embodiments, Z is deleted, $C(R_aR_b)$, $(CH_2)_p$, $(CH_2)_pNH(CH_2)_q$, CH=N, O, S, C(O), $N(R_a)$, $SO_2$, OC(O), C(O)O, $OSO_2$, $S(O_2)O$, C(O)S, SC(O), C(O)C(O), C(O)N $(R_a)$, $N(R_a)C(O)$, $S(O_2)N(R_a)$, $N(R_a)S(O_2)$, OC(O)N$(R_a)$, OC(O)O, OC(O)S, $OC(O)NH(CH_2)_{p+1}NH(CH_2)_q$, $N(R_a)C(O)O$, $N(R_a)C(O)S$, or $N(R_a)C(O)N(R_b)$, in which each of $R_a$ and $R_b$, independently, is H, alkyl, alkenyl, or alkynyl; each of p and q, independently, is 0, 1, 2, 3, or 4; each $R_1$, $R_2$, and $R_3$, independently, is H, alkyl, alkenyl, alkynyl, cycloalkyl, heterocycloalkyl, cycloalkenyl, heterocycloalkenyl, aryl, heteroaryl, halo, nitro, —CH=NH, oxo, cyano, Si($R_c R_c R_c$), alkyl-SnR$_c R_c R_c$), alkyl-R$_c$, alkyl-NR$_c R_c$, —CH=NOR$_c$, OR$_c$, OC(O)R$_c$, OC(O)OR$_c$, OC(O)SR$_c$, SR$_c$, C(O)R$_c$, C(O)OR$_c$, C(O)SR$_c$, C(O)NR$_c R_c$, SOR$_c$, SO$_2$R$_c$, NR$_c R_c$, N(R$_c$)C(O)R$_c$, in which each of R$_c$ independently, is H, alkyl, alkenyl, alkynyl, cycloalkyl, heterocycloalkyl, aryl, heteroaryl, halo, cyano, nitro, amino, hydroxyl, alkylamino, haloalkyl, or alkoxy, or $R_1$, $R_2$, and the atoms to which they are attached are taken together form a ring, which is optionally substituted with R$_c$; L is —(CH$_2$)$_m$—,

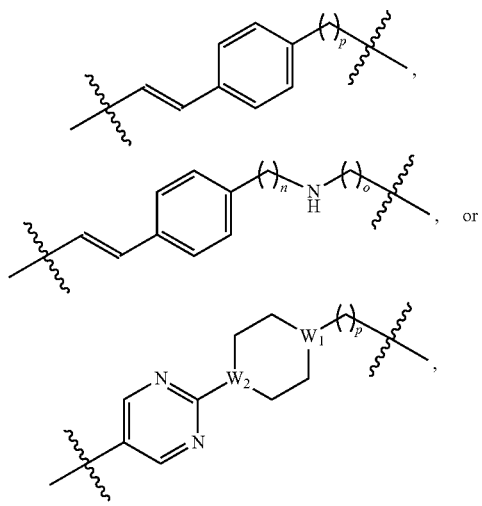

in which m is 5, 6, 7, 8, 9, 10, 11, 12, 13, 14, 15, or 16; each of n and o, independently, is 1, 2, 3, or 4; and each $W_1$ and $W_2$, independently, is CH or N.

In certain embodiments, Z is deleted, (CH$_2$)$_p$, (CH$_2$)$_p$NH(CH$_2$)$_q$, CH=N, O, CO, NH, SO$_2$, OC(O), OSO$_2$, C(O)O, C(O)S, NHC(O), C(O)NH, OC(O)NH(CH$_2$)$_{p+1}$NH(CH$_2$)$_q$, OC(O)NH, OC(O)O, or OC(O)S; m is 5, 6, 7 or 8; and each $R_1$, $R_2$, and $R_3$, independently, is H, alkyl, alkenyl, alkynyl, cycloalkyl, heterocycloalkyl, nitro, oxo, halo, cyano, —CH=NH, Si($R_c R_c R_c$), alkyl-Si($R_c R_c R_c$), alkyl-R$_c$, alkyl-NR$_c R_c$, CH=NOR$_c$, or NR$_c R_c$.

In certain embodiments, Z is O, OC(O), OSO$_2$, OC(O)NH, OC(O)O, OC(O)S, or OC(O)NH(CH$_2$)$_{p+1}$NH(CH$_2$)$_q$; m is 6 or 7; $R_3$ is H or F; each R$_c$ independently, is H, alkyl, alkenyl, alkynyl, cycloalkyl, heterocycloalkyl, amino, hydroxyl, alkylamino, haloalkyl, or alkoxy; and $W_2$ is N.

In certain embodiments, each $R_1$ and $R_2$, independently, is H, alkyl, alkenyl, alkynyl, cycloalkyl, heterocycloalkyl, nitro, Si($R_c R_c R_c$), alkyl-Si($R_c R_c R_c$), alkyl-R$_c$, alkyl-NR$_c R_c$, CH=NOR$_c$, or NR$_c R_c$.

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such hydroxamic compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable pro-drug derivatives, deuterium-enriched hydroxamic compounds, and conjugate with polyethylene glycol, dextran, polyvinyl alcohol, carbohydrate polymer, antibody, biomolecule such as Vitamin E or its derivatives, or mixtures thereof.

It should be recognized that the compounds of the present invention may be present and optionally administered in the form of salts or solvates. The invention encompasses any pharmaceutically acceptable salts and solvates of any one of the above-described hydroxamic compounds and modifications thereof.

Also within the scope of this invention is a pharmaceutical composition containing one or more of the hydroxamic compounds, modifications, and/or salts and thereof described above for use in treating a neoplastic disease, or an immune disorder, therapeutic uses thereof, and use of the compounds for the manufacture of a medicament for treating the disease/disorder.

This invention also relates to a method of treating a neoplastic disorder (e.g., cancer, myelodysplastic syndrome, or myeloproliferative disease) by administering to a subject in need thereof an effective amount of one or more of the hydroxamic compounds, modifications, and/or salts, and compositions thereof described above.

Furthermore, this invention relates to a method of treating an immune disease (e.g., rheumatoid arthritis and multiple sclerosis) by administering to a subject in need thereof an effective amount of one or more of the hydroxamic compounds, modifications, and/or salts, and compositions thereof described above.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

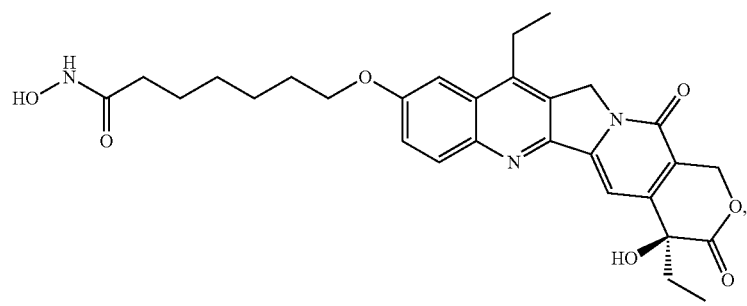

-continued
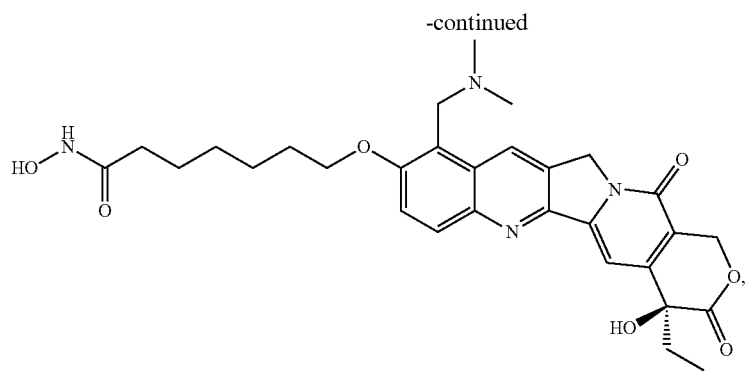
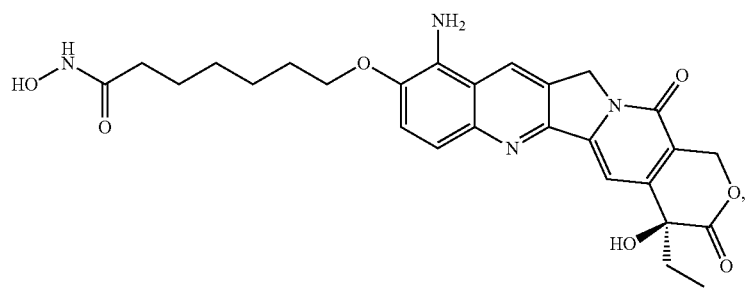
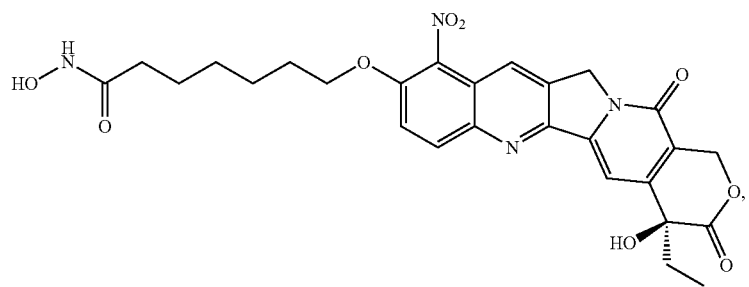
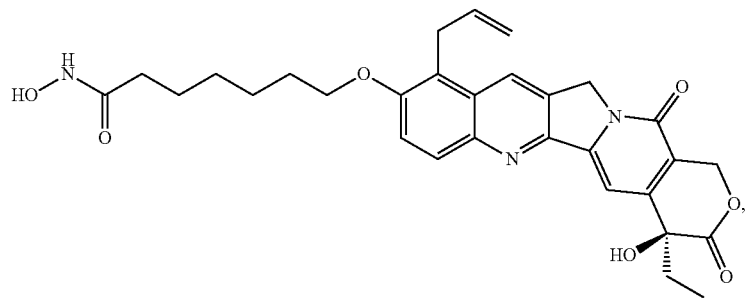
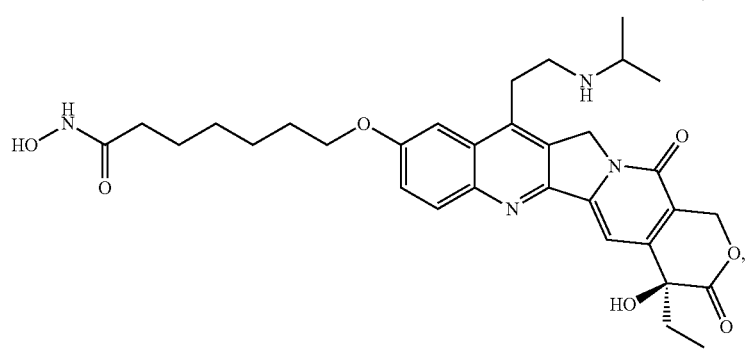

-continued
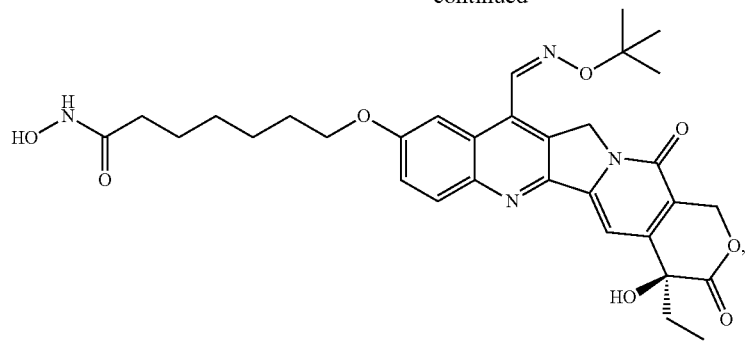
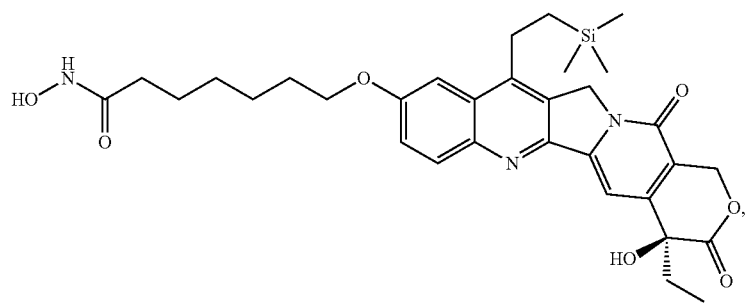
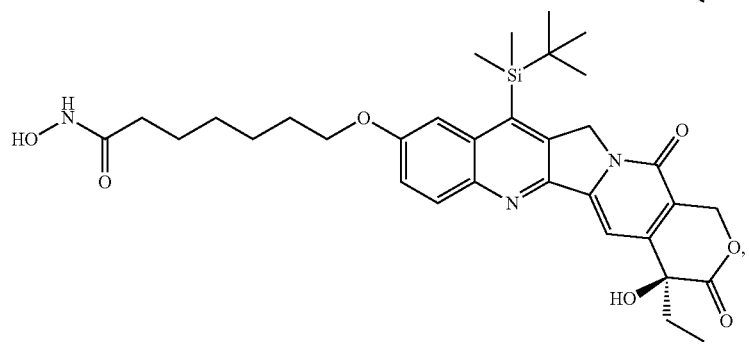
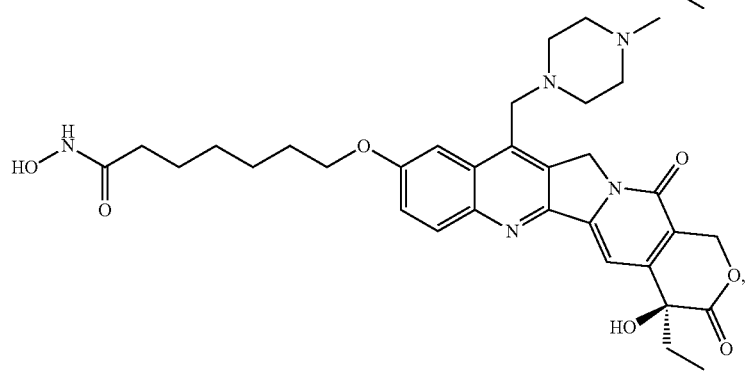
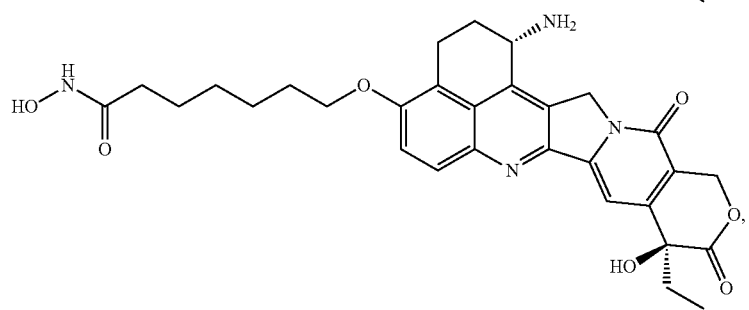

-continued
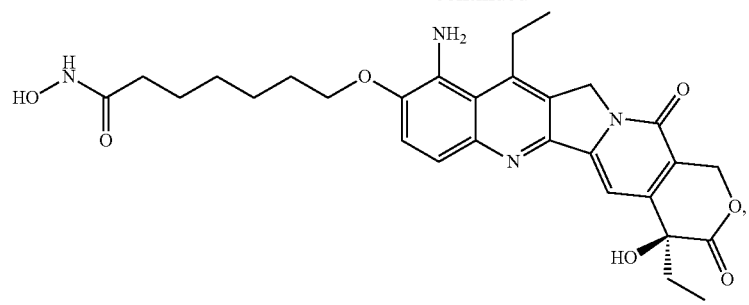
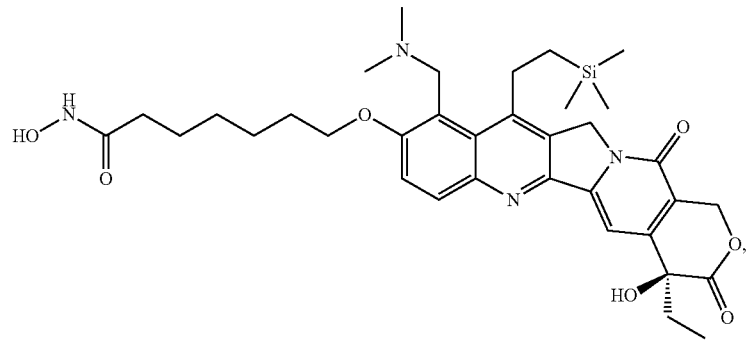
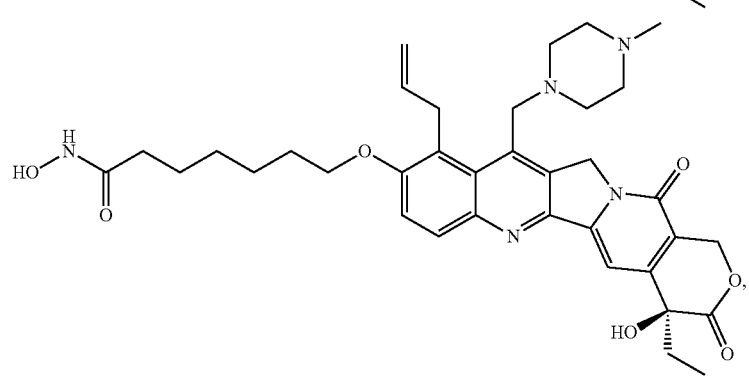
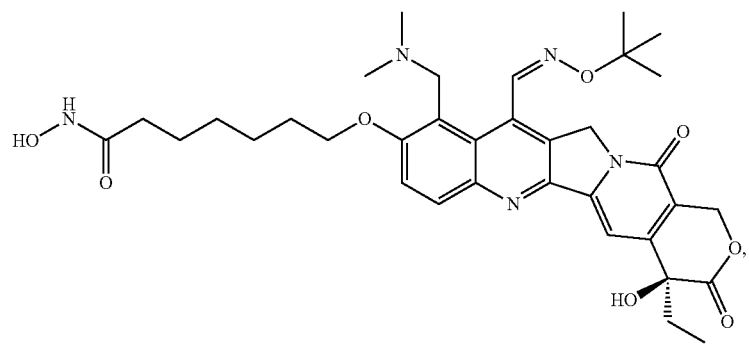
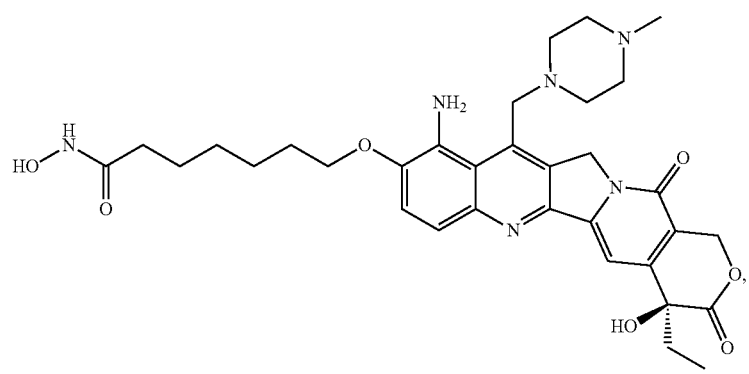

-continued
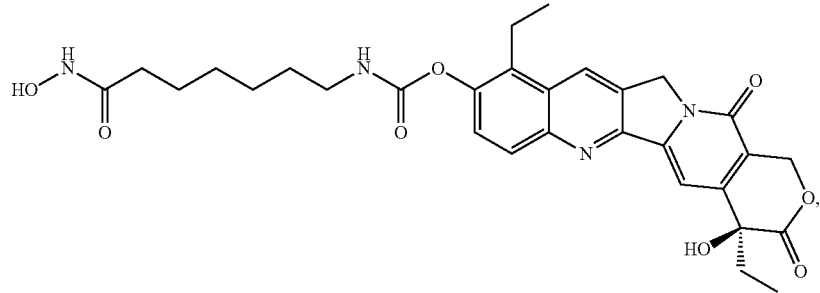
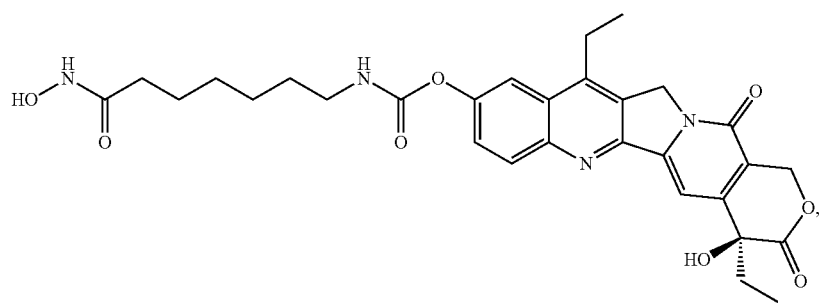
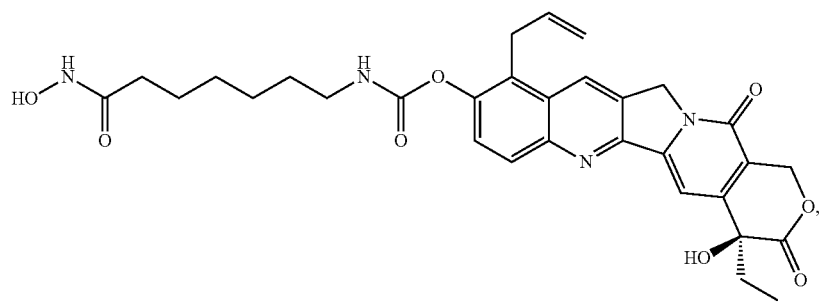
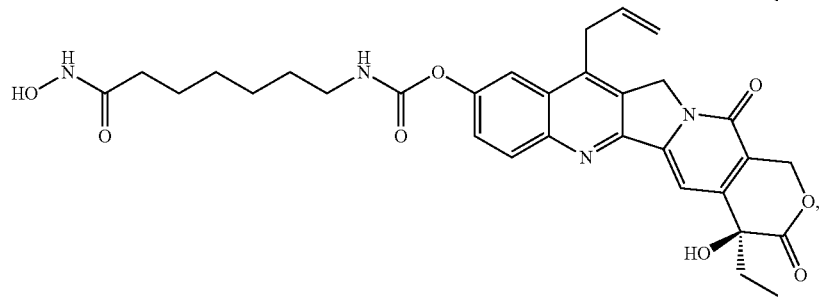
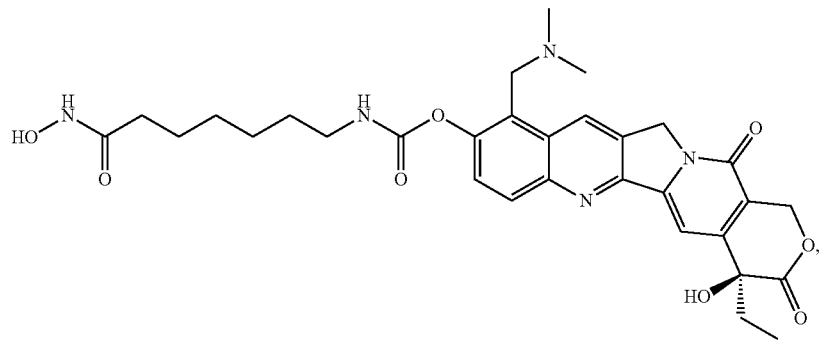

-continued
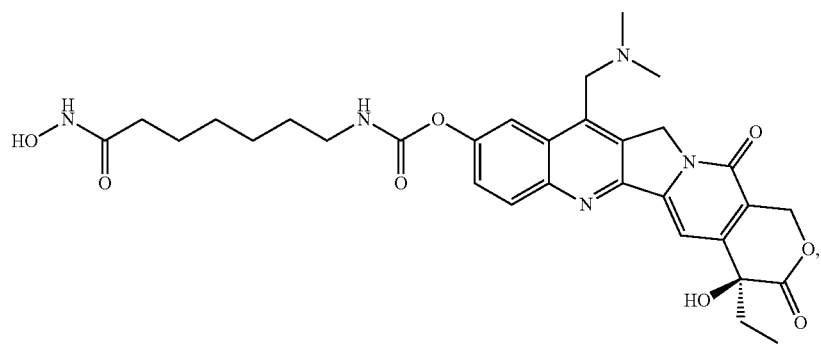
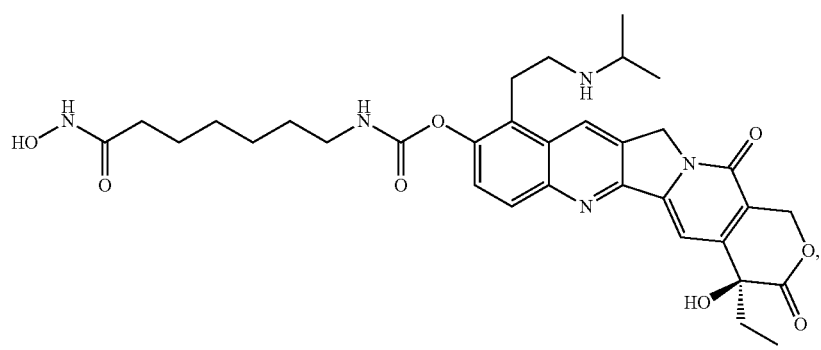
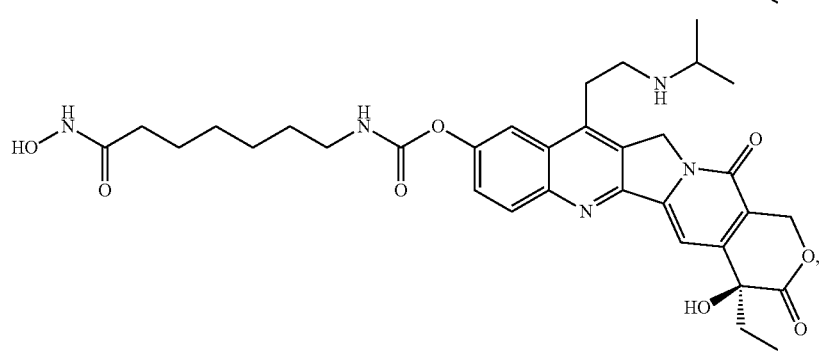
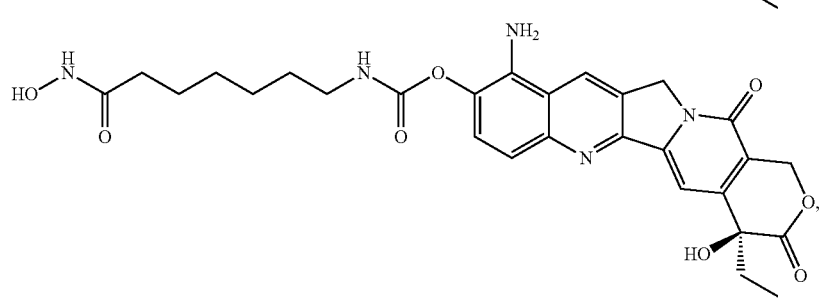
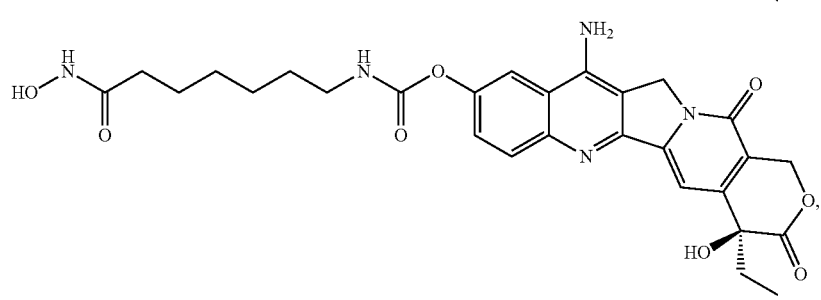

-continued
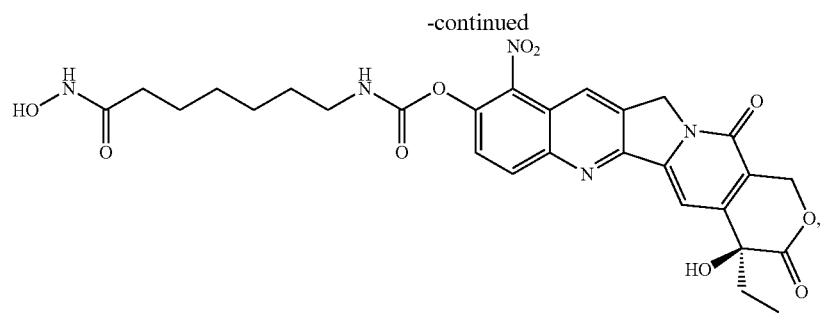
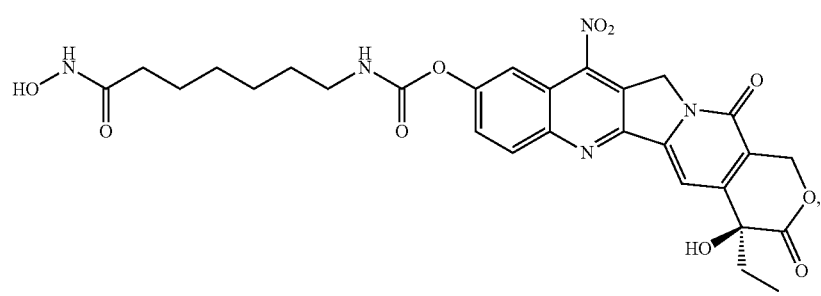
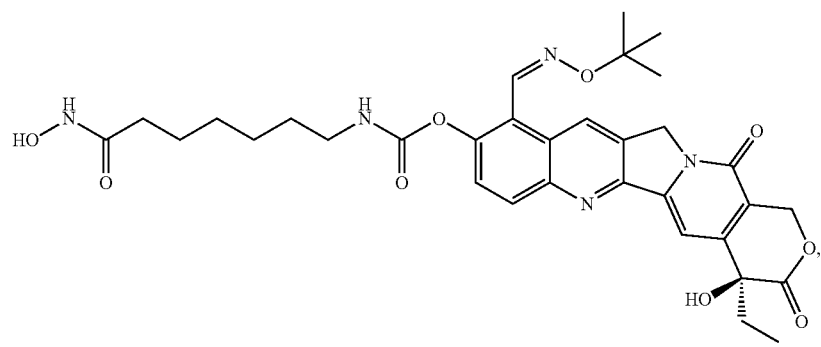
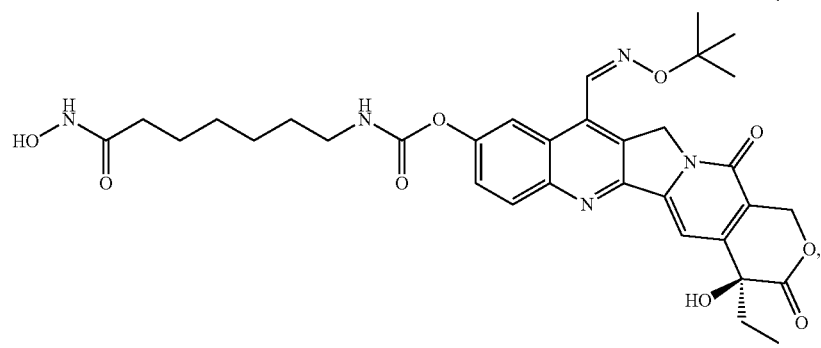
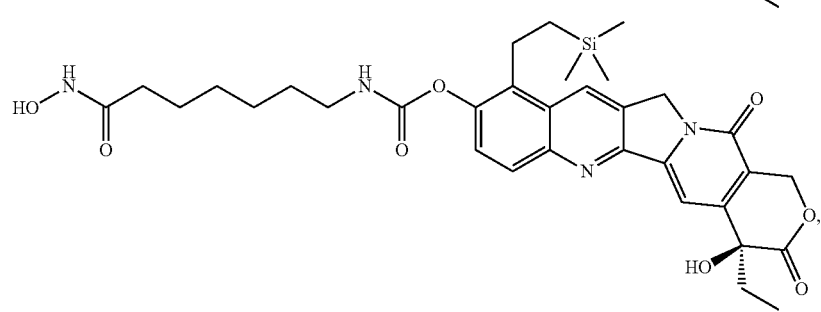

-continued
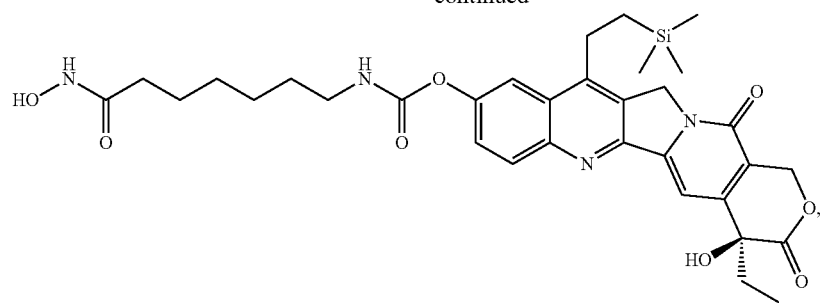
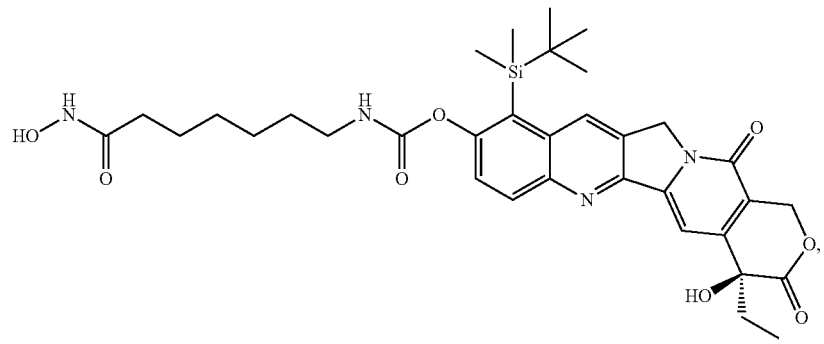
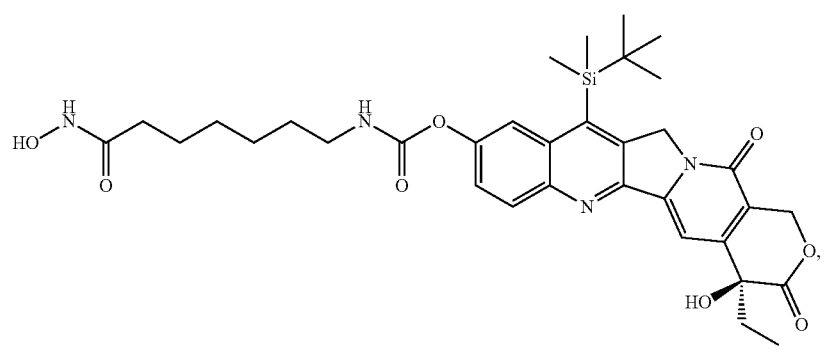
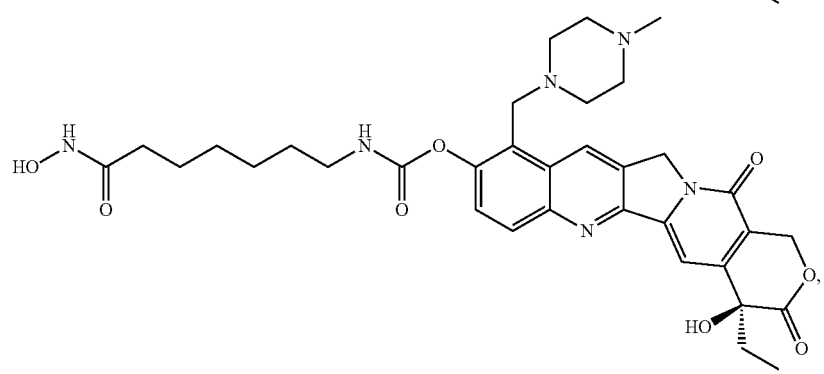
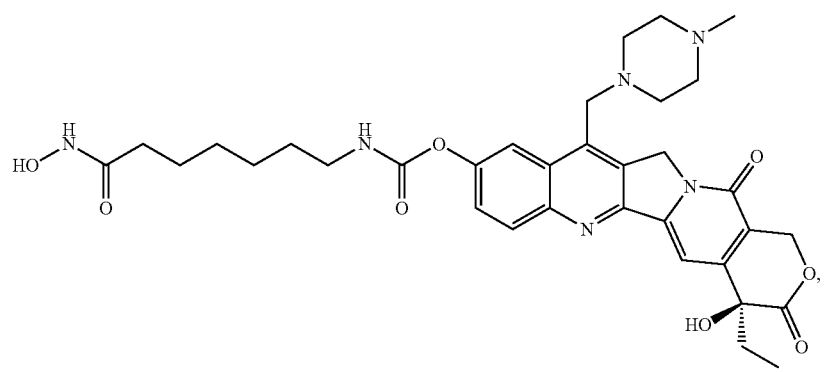

-continued
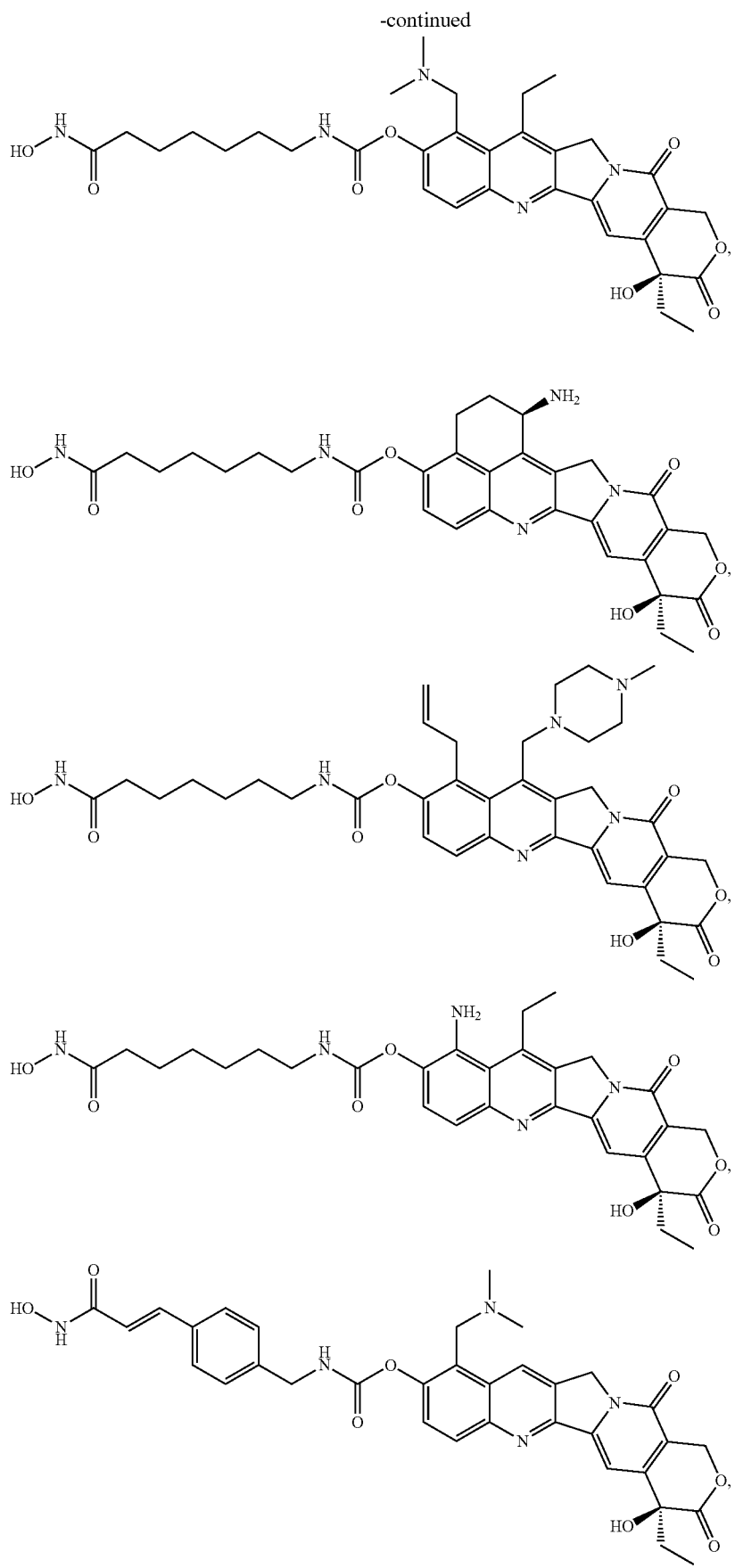

-continued
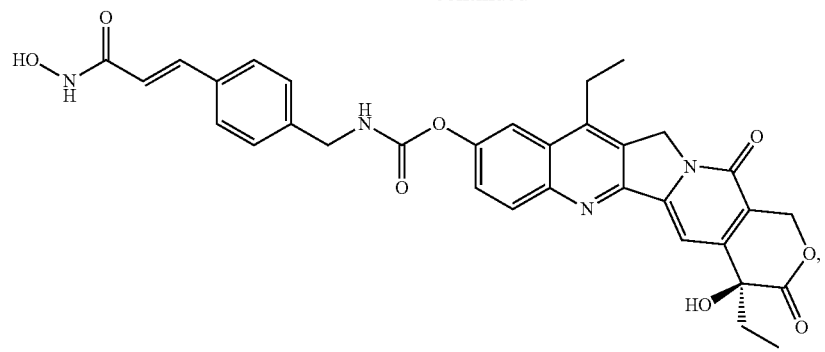
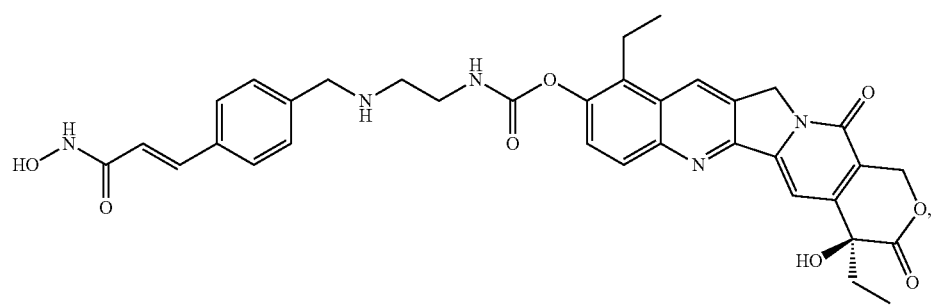
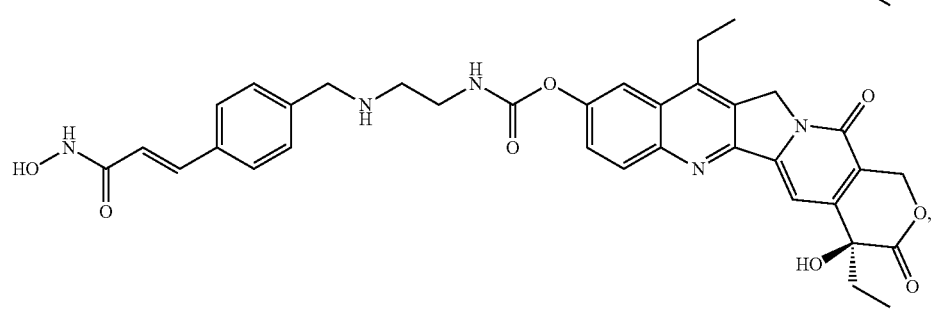
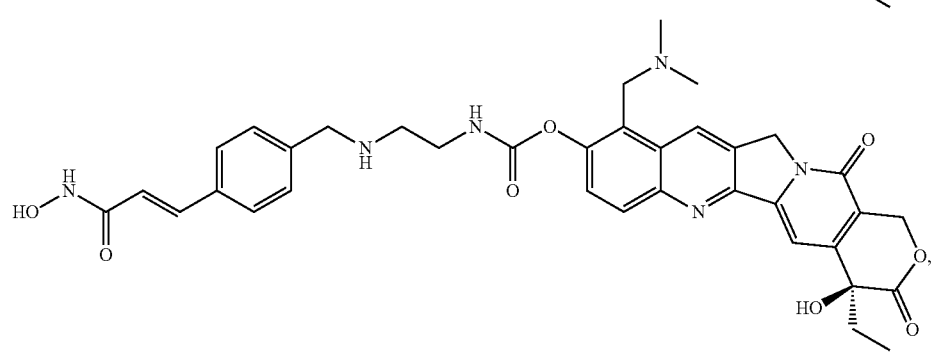
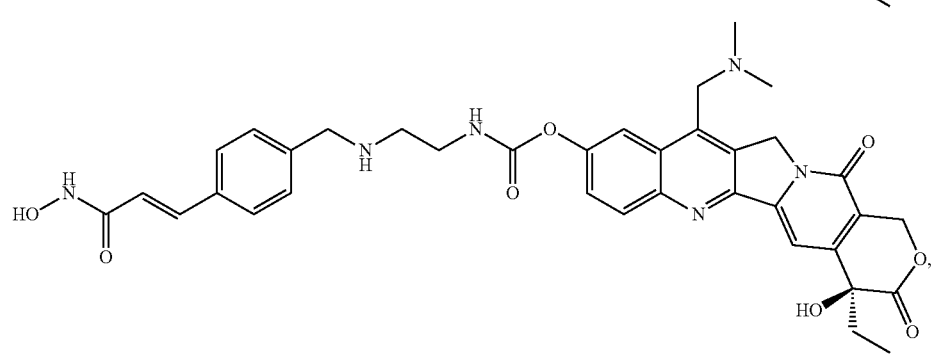

-continued
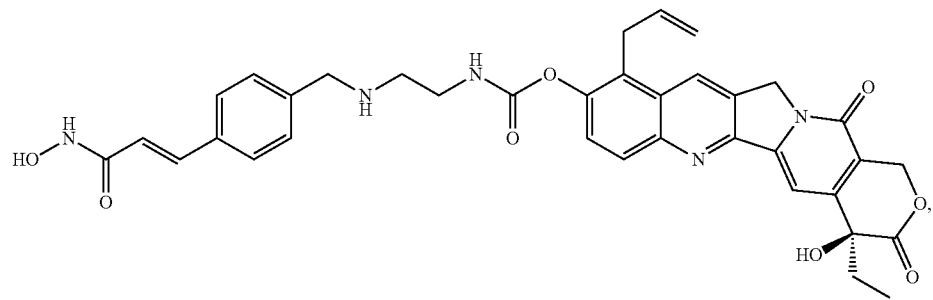
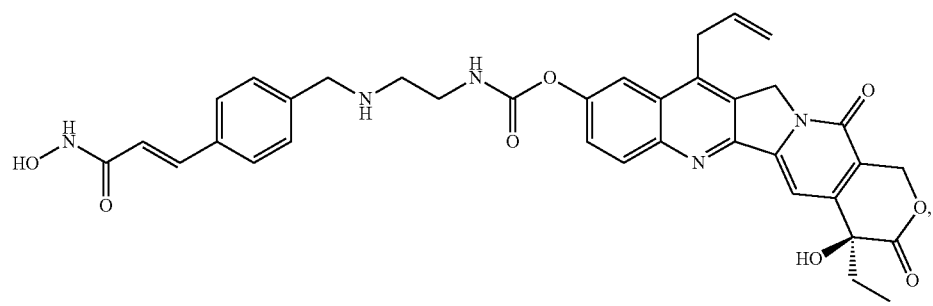
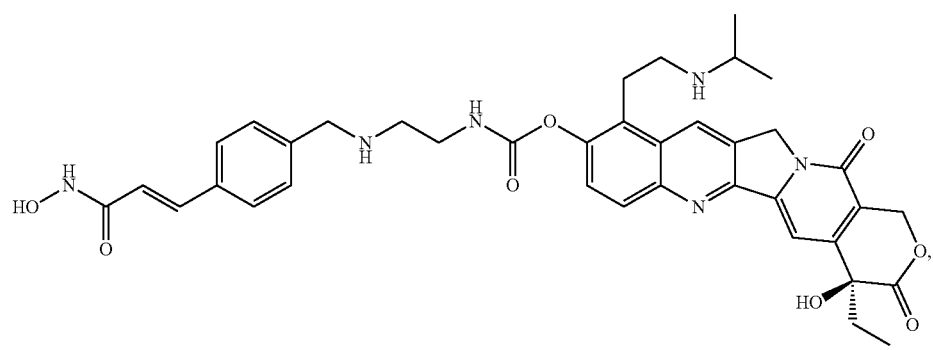
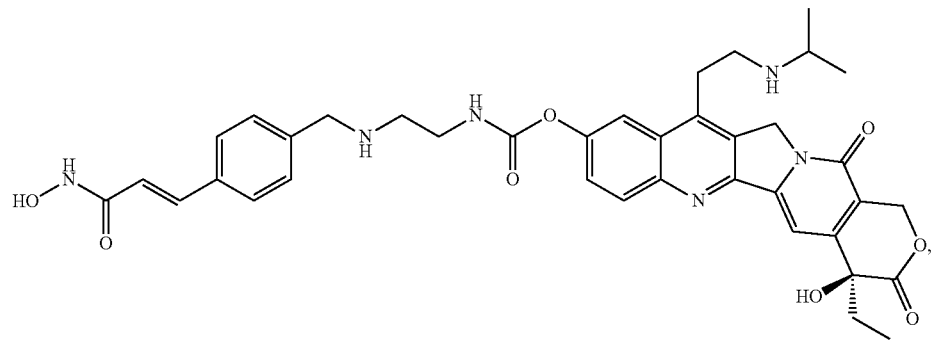
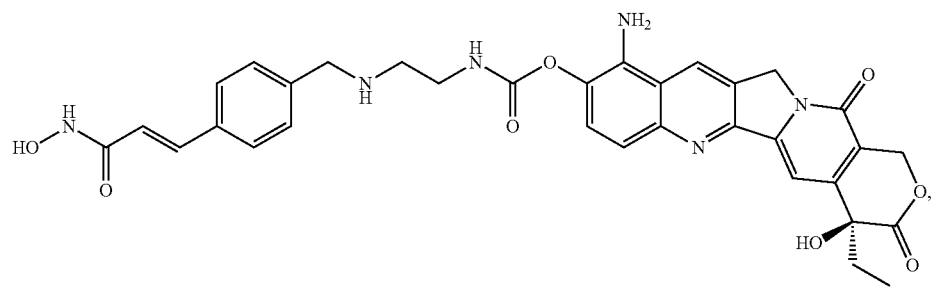

-continued
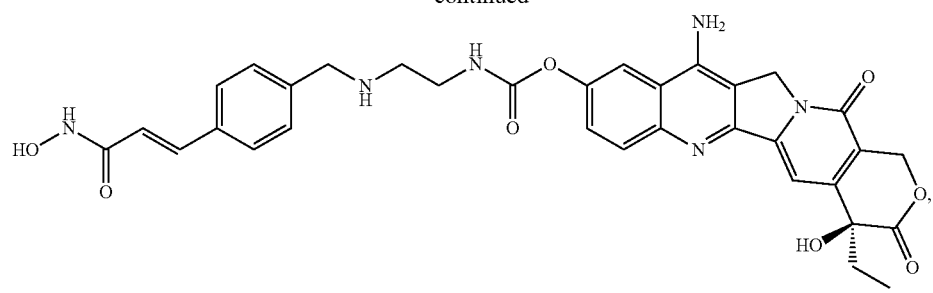
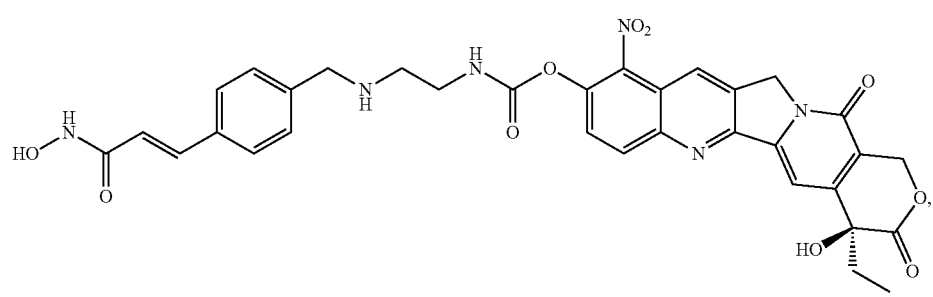
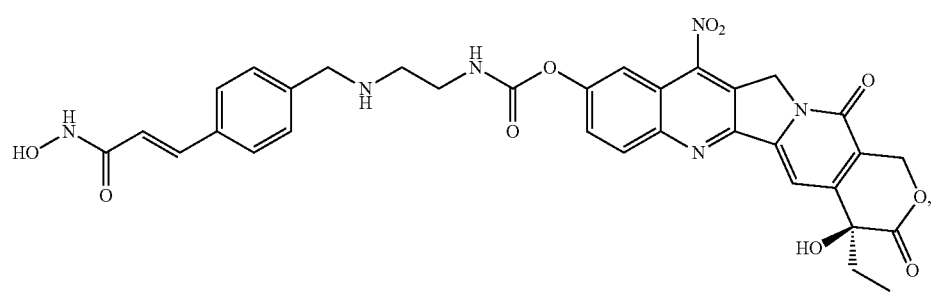
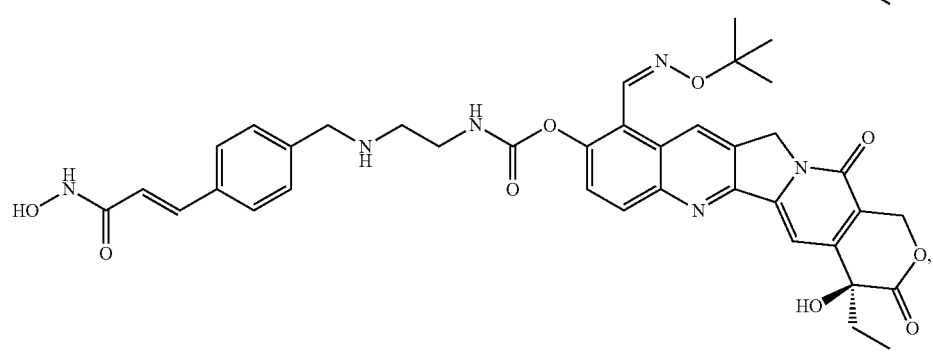
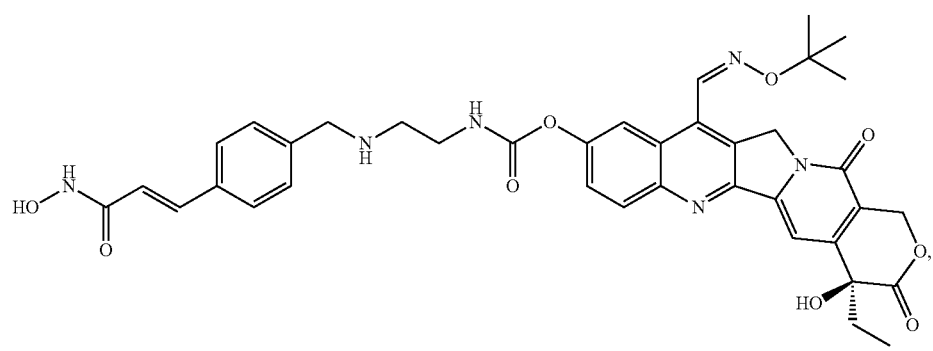

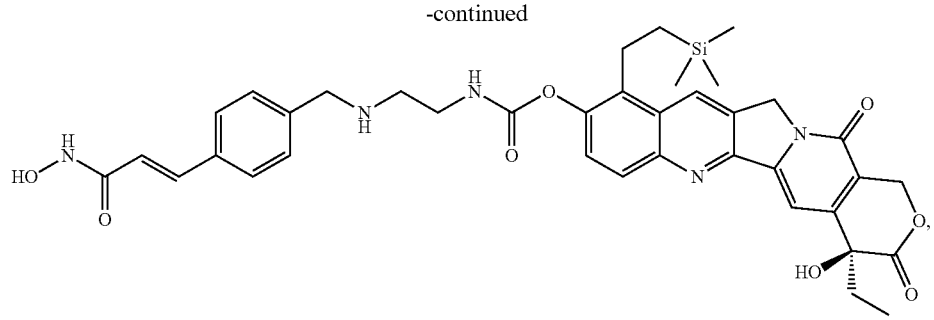
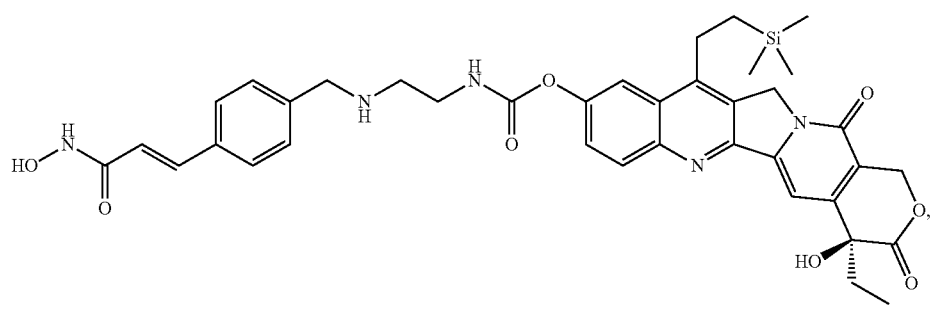
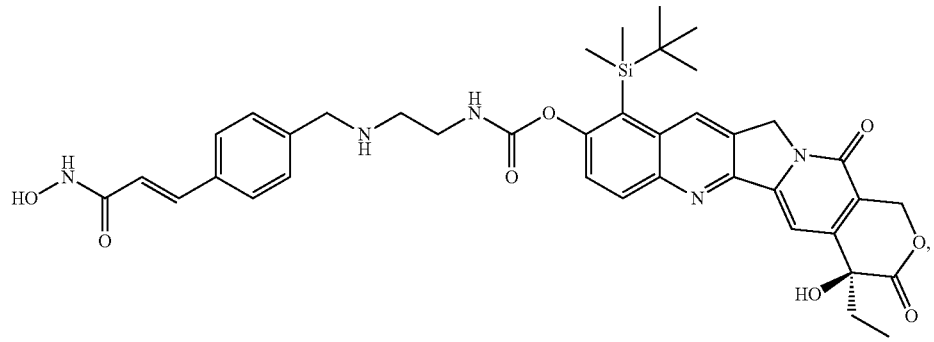
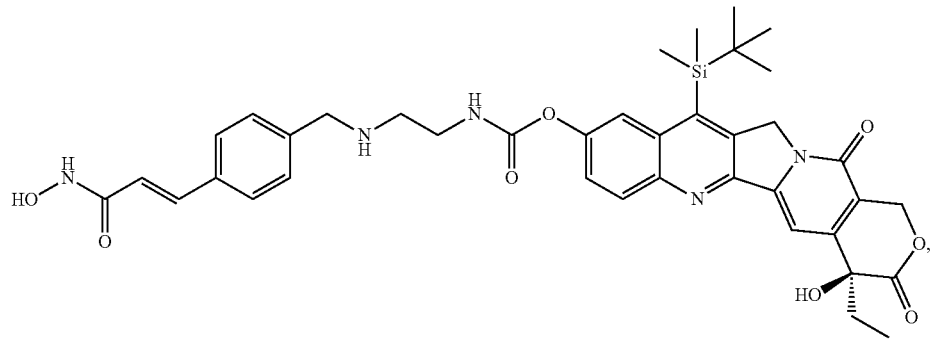
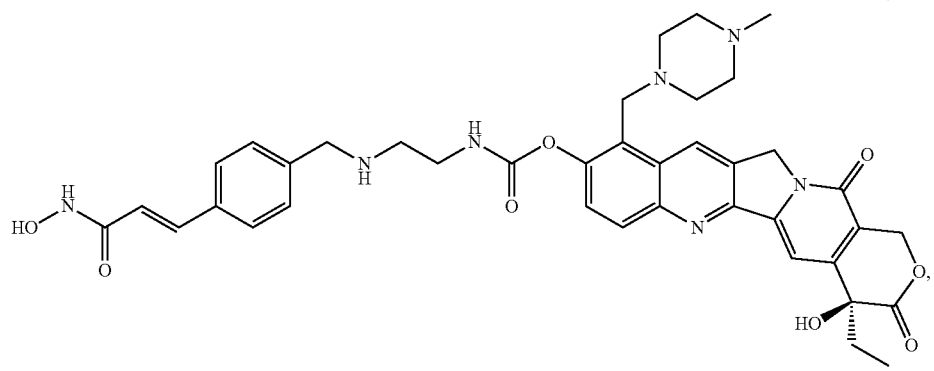

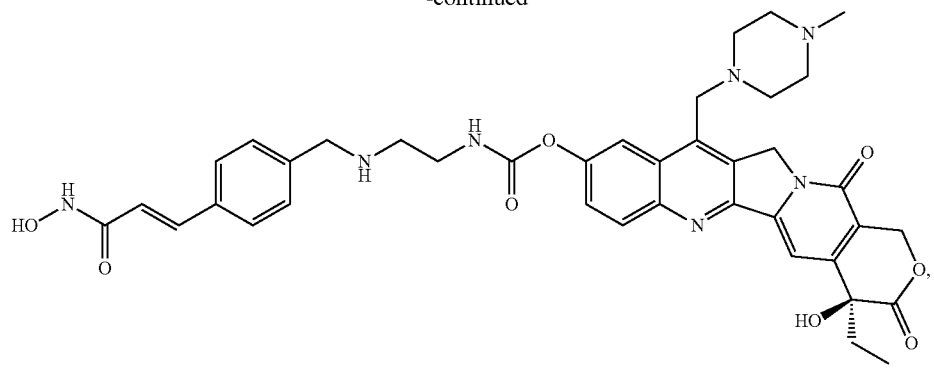
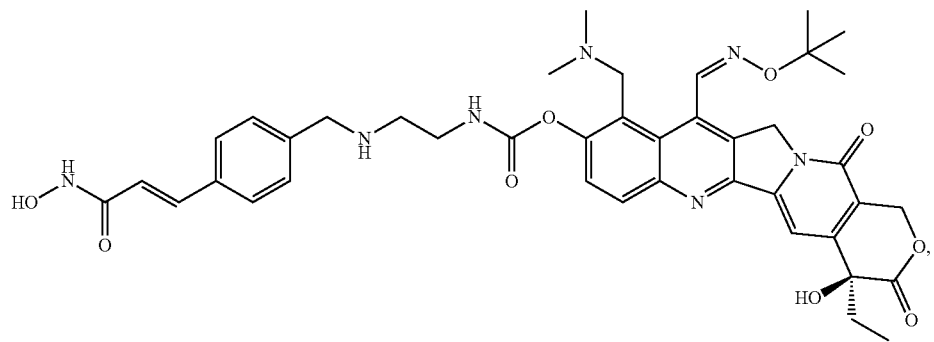
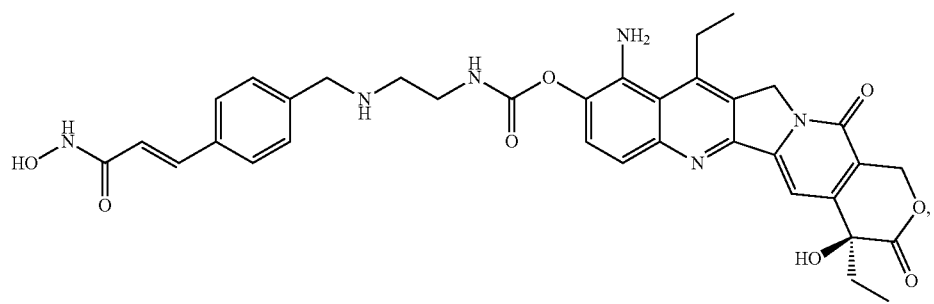
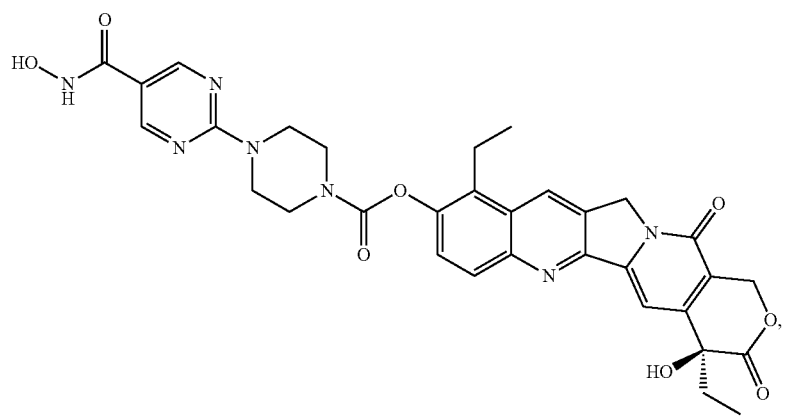

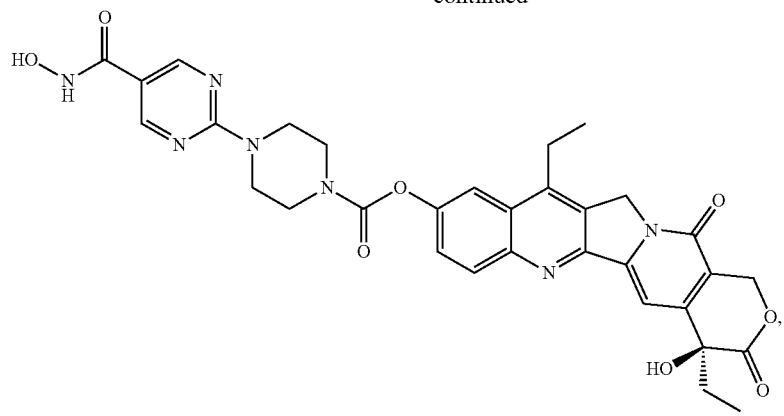
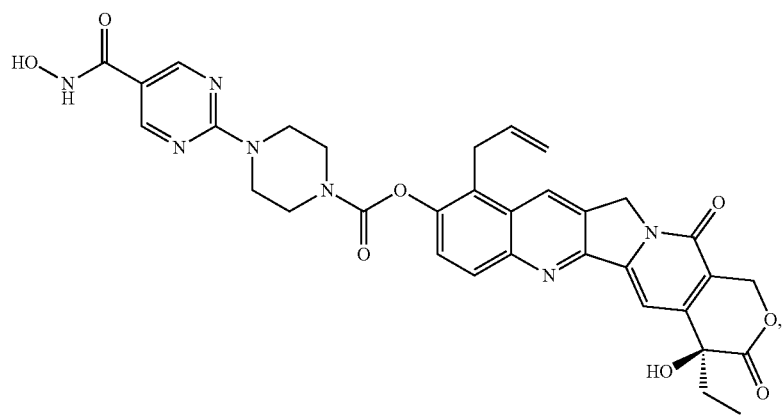
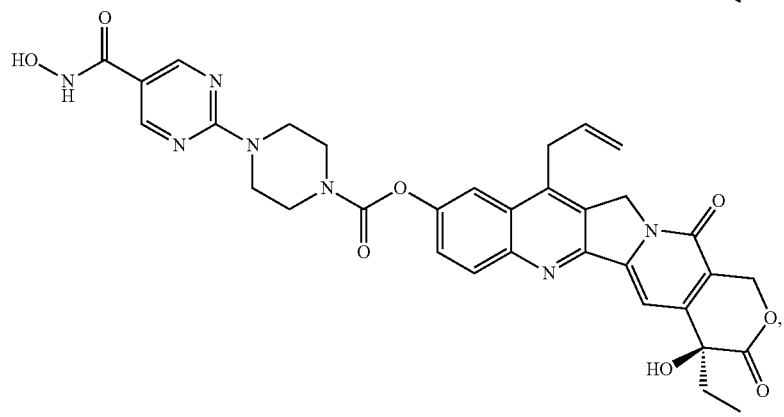
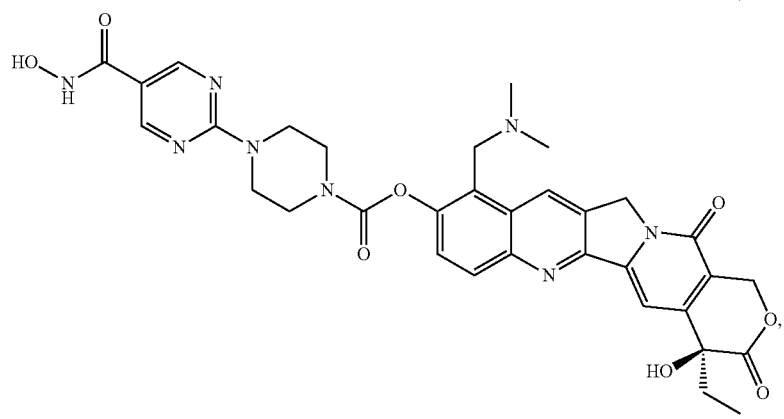

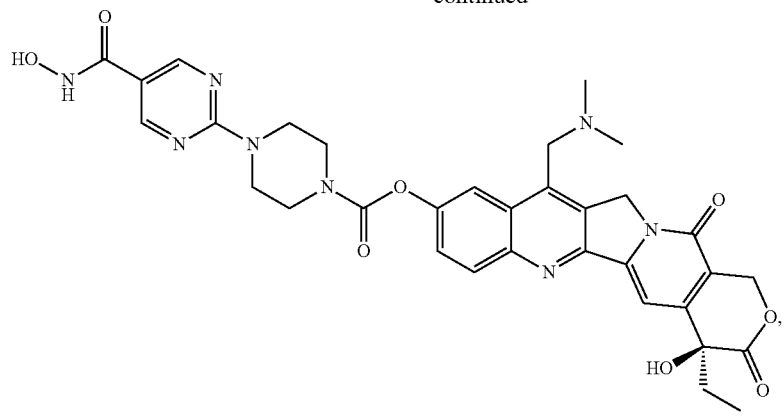
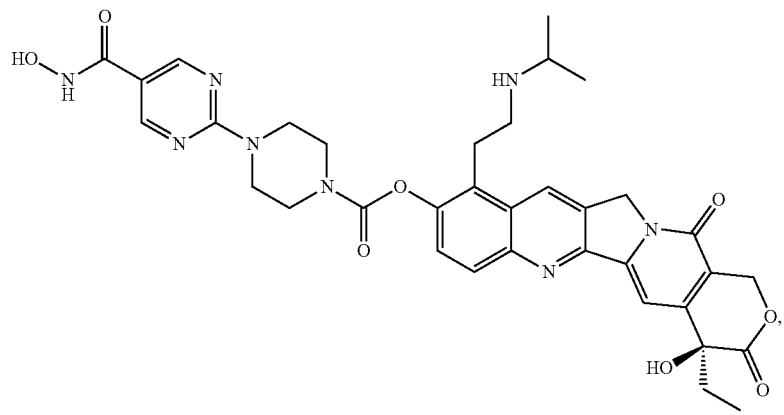
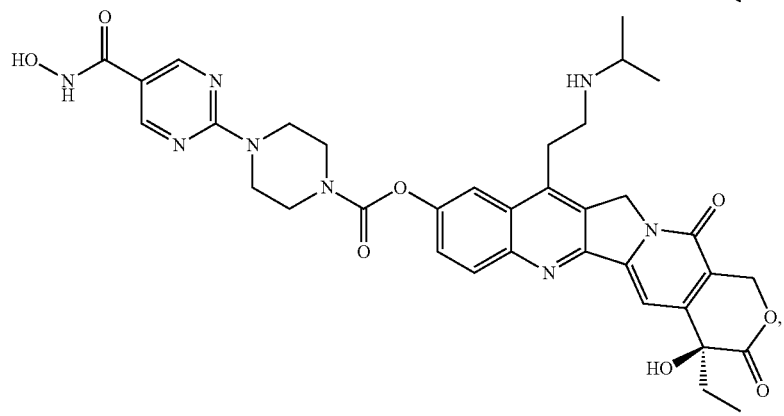
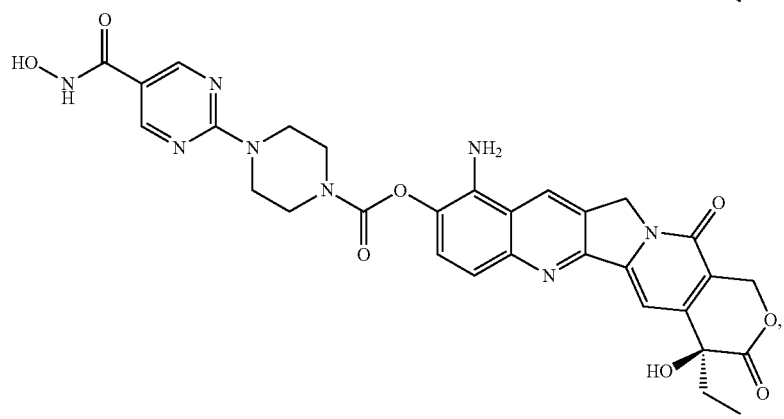

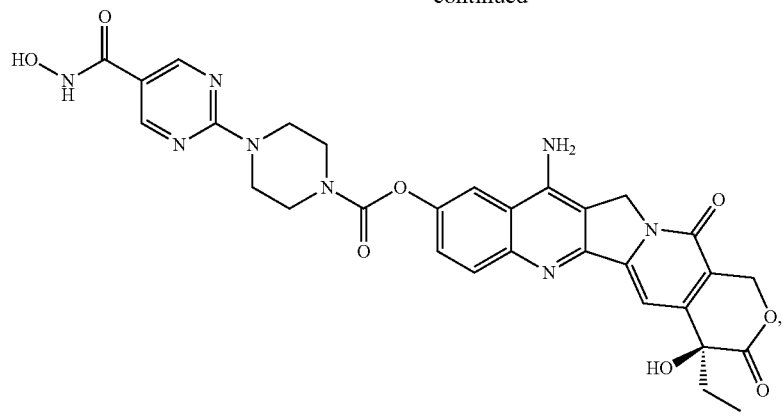
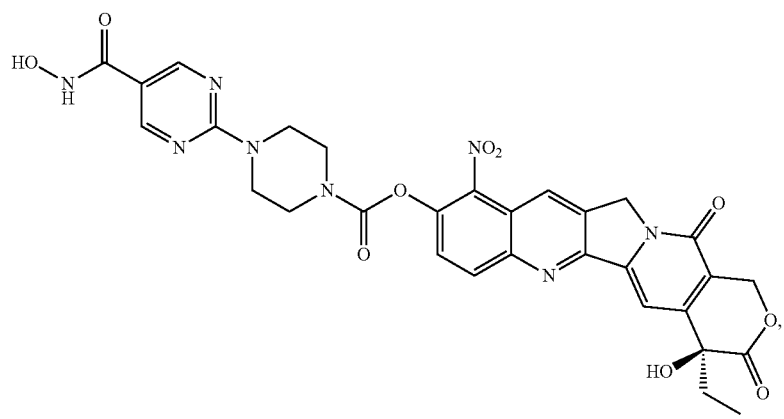
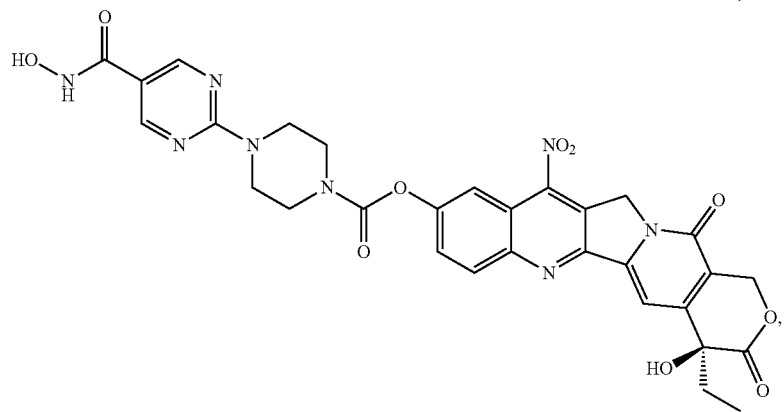
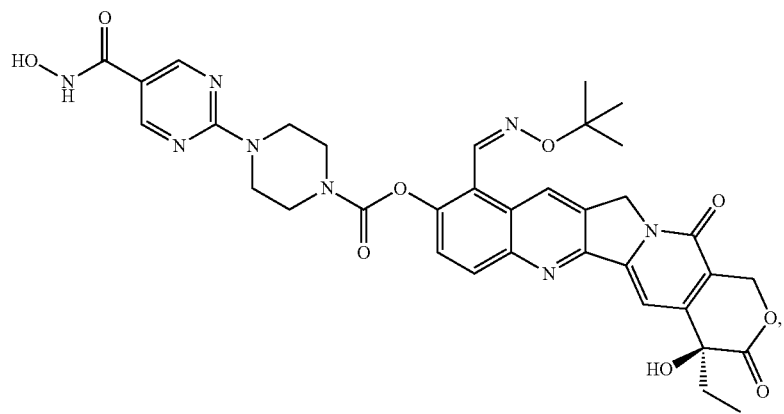

-continued
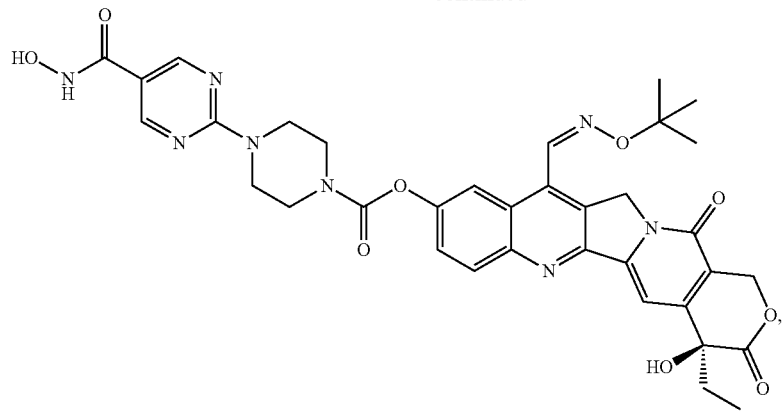
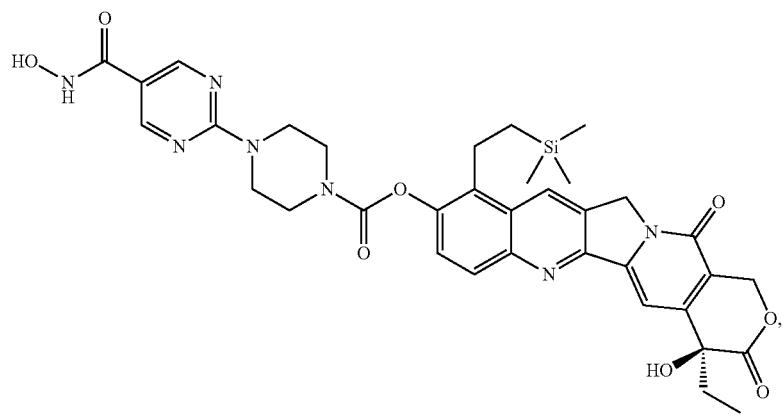
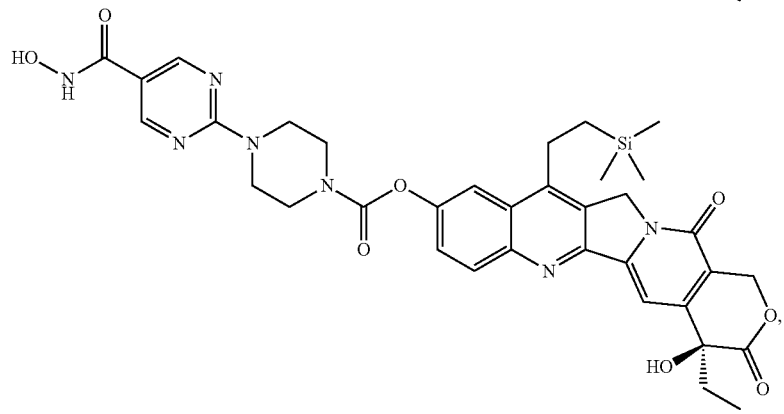
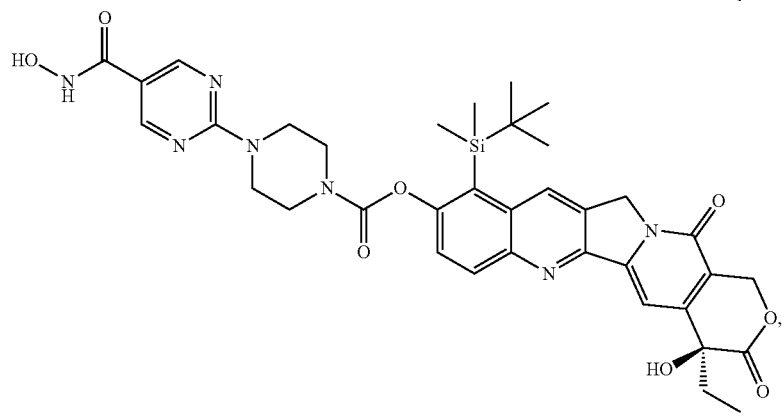

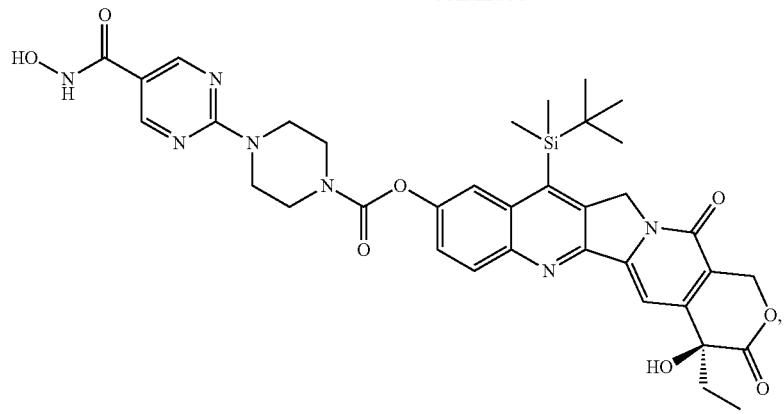
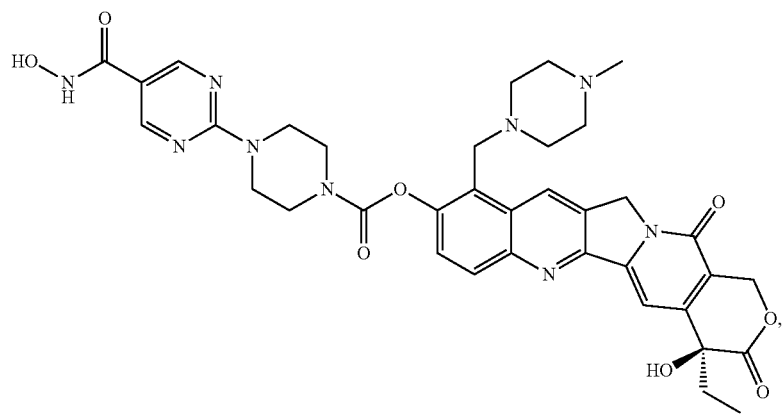
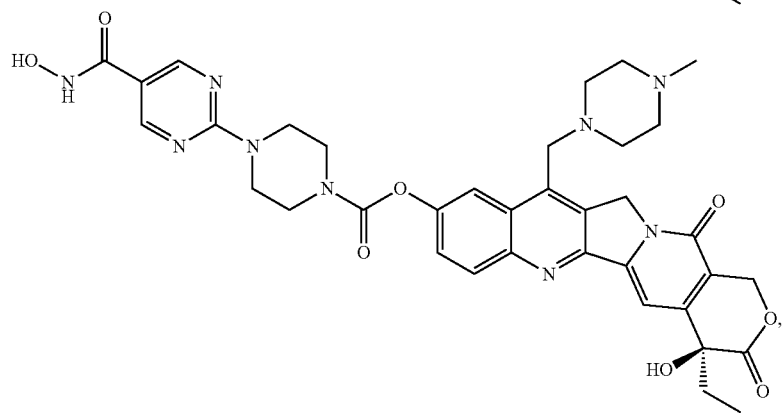
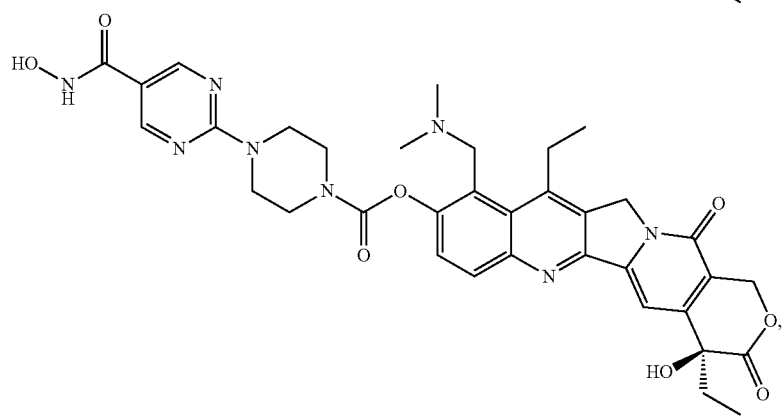

-continued

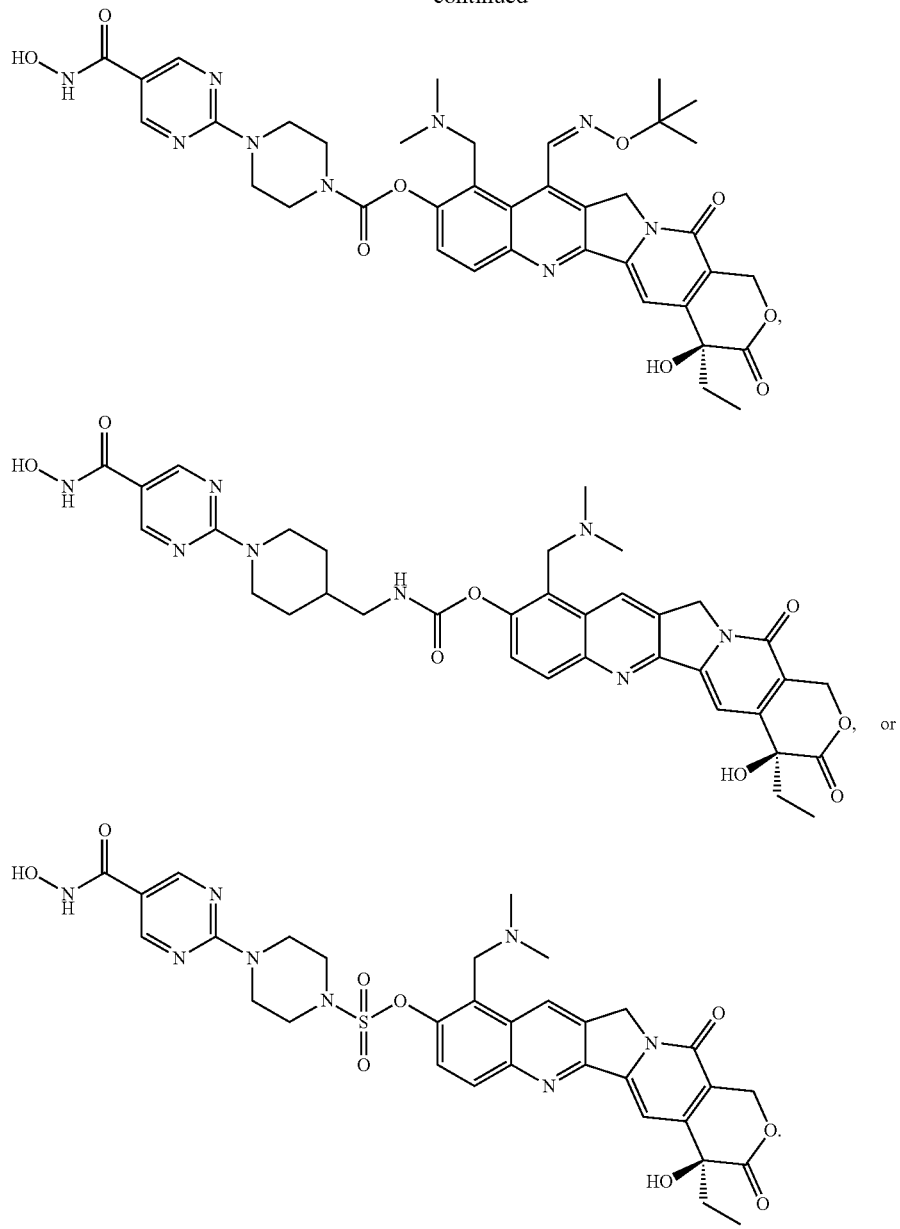

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such hydroxamic compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, the deuterium-enriched hydroxamic compounds, and hydroxamic compound conjugates with polyethylene glycol, dextran, polyvinyl alcohol, carbohydrate polymer, antibody, small biomolecule such as Vitamin E or its derivatives, or mixtures thereof. For example:

Prodrug derivatives: prodrugs, upon administration to a subject, will converted in vivo into active hydroxamic compounds of the present invention [*Nature Reviews of Drug Discovery*, 2008, Volume 7, p255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters*, 1994, Vol. 4, p. 1985.

Deuterium-enriched hydroxamic compounds: deuterium (D or $^2$H) is a stable, non-radioactive isotope of hydrogen and has an atomic weight of 2.0144. Hydrogen naturally occurs as a mixture of the isotopes $^x$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

Hydroxamic compound-polymer conjugates: 20(S)-camptothecin and many of its derivatives exhibit excellent antitumor activity against human cancer cell lines and in vivo animal xenografts. However, their water insolubility makes it difficult to administer these drugs. Additionally, the pharmacologically important lactone ring of 20(S) camptothecin and its analogs is unstable in the presence of human plasma albumin which results in the conversion of the active drug to the inactive carboxylate form which is bound to the albumin. One approach to overcome the pharmaceutical and pharmacokinetic shortcomings of 20(S)-camptothecin and its derivatives is to covalently bind them to polymers such as polyethylene glycol, dextran, polyvinyl alcohol, and carbohydrate polymer. Using this approach, the water solubility of the most active camptothecins can be improved such that the polymeric conjugated can be parenterally administered in aqueous medium.

Hydroxamic compound-antibody conjugates: For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed. The toxic agent is most commonly a chemotherapy drug, although particle-emitting radionuclides, or bacterial or plant toxins have also been conjugated to MAbs, especially for the therapy of cancer (Sharkey and Goldenberg, C A Cancer J. Clin. 2006 July-August; 56(4):226-243). The advantages of using MAb-chemotherapy drug conjugates are that (a) the chemotherapy drug itself is structurally well defined; (b) the chemotherapy drug is linked to the MAb protein using very well defined conjugation chemistries, often at specific sites remote from the MAbs antigen binding regions; (c) MAb-chemotherapy drug conjugates can be made more reproducibly than chemical conjugates involving MAbs and bacterial or plant toxins, and as such are more amenable to commercial development and regulatory approval; and (d) the MAb-chemotherapy drug conjugates are orders of magnitude less toxic systemically than radionuclide MAb conjugates.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as ($C_{1-4}$) alkyl halides, e.g., methyl, ethyl, iso-propyl and tert-butyl chlorides, bromides and iodides; di-($C_{1-4}$) alkyl sulfates, e.g., dimethyl, diethyl and diamyl sulfates; alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the hydroxamic compound of the invention. For example, the hydroxamic compounds can be in a crystalline form, in amorphous form, and have any particle size. The particles may be micronized, or may be agglomerated, particulate granules, powders, oils, oily suspensions or any other form of solid or liquid physical form.

DEFINITIONS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NRaRb where Ra and Rb are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers."Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —$NO_2$.

"Protected derivatives" means derivatives of inhibitors in which a reactive site are blocked with protecting groups. Protected derivatives are useful in the preparation of inhibitors or in themselves may be active as inhibitors. A comprehensive list of suitable protecting groups can be found in T. W. Greene, Protecting Groups in Organic Synthesis, 3rd edition, Wiley & Sons, 1999.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases.

"Prodrug" means a compound that is convertible in vivo metabolically into an inhibitor according to the present invention. For example, an inhibitor comprising a hydroxyl group may be administered as an ester that is converted by hydrolysis in vivo to the hydroxyl compound.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a hydroxamic compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

General

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase II inhibitors (e.g., Amsacrine, etoposide, etoposide phosphate, teniposide), and miscellaneous anti-neoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited to: serine/threonine specific kinases, receptor tyrosine specific kinases, and non-receptor tyrosine specific kinases. Examples of serine/threonine kinases include mitogen activated protein kinases (MAPK), meiosis specific kinase (MEK), RAF and aurora kinase. Examples of receptor kinase families include epidermal growth factor receptor (EGFR) (e.g., HER2/neu, HER3, HER4, ErbB, ErbB2, ErbB3, ErbB4, Xmrk, DER, Let23); fibroblast growth factor (FGF) receptor (e.g., FGFR, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g., IGFI-R); Eph (e.g., CEK5, CEK8, EBK, ECK, EEK, EHK-1, EHK-2, ELK, EPH, ERK, HEK, MDK2, MDK5, SEK); Axl (e.g., Mer/Nyk, Rse); RET; and platelet-derived growth factor receptor (PDGFR) (e.g., PDGFα-R, PDGFβ-R, CSF1-R/FMS, SCF-R/C-KIT, VEGF-R/FLT, NEK/FLK1, FLT3/FLK2/STK-1), and ALK. Examples of non-receptor tyrosine kinase families include, but are not limited to, BCR-ABL (e.g., p43aW, ARG); BTK (e.g., ITK/EMT, TEC); CSK, FAK, FPS, JAK, SRC, BMX, FER, CDK and SYK.

In another aspect of the invention, the subject compounds may be administered in combination with one or more targeted anti-cancer agents that modulate non-kinase biological targets or processes. Such targets include DNA methyltransferase (DNMT), heat shock proteins (e.g., HSP90), poly-ADP (adenosine diphosphate)-ribose polymerase (PARP), matrix metalloproteinase (MMP), hedgehog signaling protein, and farnesyl transferase, and proteosomes.

In certain preferred embodiments, the compounds of the invention are administered in combination with one or more of therapeutic agents that include, but are not limited to, angiogenesis inhibitors, apoptosis promoters (for example, Bcl-xL, Bcl-w and Bfl-1 inhibitors), activators of a death receptor pathway, hormonal therapies, gene therapy, chemoprotective agents (e.g., amfostine, mesna, and dexrazoxane), immunotherapeutic agent, vaccines (e.g., sipuleucel-T), antibody conjugate (e.g brentuximab vedotin, ibritumomab tioxetan), or monoclonal antibodies (e.g., Bevacizumab, Alemtuzumab, Rituximab, Trastuzumab).

In certain preferred embodiments, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain preferred embodiments, the compounds of the invention are administered in combination with one or more of traditional chemotherapeutic agents, targeted anti-cancer agents, monoclonal antibodies, immunotherapeutic agent, antibody conjugate, gene therapy, cancer vaccines, angiogenesis inhibitors, apoptosis promoters, activators of a death receptor pathway, hormonal therapies, chemoprotective agents, radiation therapy or surgeries. For example, a combination therapy illustratively include administration of compounds of the present invention with one or more of abarelix, abiraterone acetate, aldesleukin, alemtuzumab, altretamine, anastrozole, asparaginase, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, Ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

The invention further provides methods for the prevention or treatment of a neoplastic disease or immune disease. In one embodiment, the invention relates to a method of treating a neoplastic disease or immune disease in a subject in need of treatment comprising administering to said subject a therapeutically effective amount of a compound of the invention. In one embodiment, the invention further provides for the use of a compound of the invention in the manufacture of a medicament for halting or decreasing a neoplastic disease or immune disease.

The neoplastic disease includes but not limited to lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome and myeloproliferative disease.

It is well known that immunosuppression is one of major side-effect of many conventional chemotherapeutics. For example, at low dose, cyclophosphamide can be used to treat immune diseases such as multiple sclerosis, rheumatoid arthritis and the suppression of transplant rejections (Emadi A, et al, *Nat Rev Clin Oncol.* 2009 November; 6(11):638-47; Perini P, et al. *Neurol Sci.* 2008 September; 29 Suppl 2:S233-4) and is also widely used in bone marrow transplantation "conditioning" and "mobilization" regimens, and for the treatment of refractory severe autoimmune conditions, such as systemic lupus erythematosus (SLE), minimal change disease, severe rheumatoid arthritis, Wegener's granulomatosis (with trade name Cytoxan), scleroderma, and multiple sclerosis (with trade name Revimmune). In addition, HDAC has recently emerging as a promising target for treating immune disease [Szyf M. *Clin Rev Allergy Immunol.* 2010 August; 39(1):62-77]. Therefore it is not difficult to imagine the compounds of present invention could be used, at low dose, for treatment of an immune disease.

In a preferred embodiment, the immune disease is selected from the group consisting of the rejection of transplanted organs and tissues, a graft-versus-host disease, a non-autoimmune inflammatory disease, and an autoimmue disease, wherein said autoimmue disease is selected from the group consisting of acute disseminated encephalomyelitis, addison's disease, ankylosing spondylitis, antiphospholipid antibody syndrome, autoimmune hemolytic anemia, autoimmune hepatitis, autoimmune inner ear disease, bullous pemphigoid, coeliac disease, chagas disease, chronic obstructive pulmonary disease, churg-strauss syndrome, dermatomyositis, Crohn's disease, diabetes mellitus type 1, endometriosis, goodpasture's syndrome, graves' disease, guillain-barré syndrome, hashimoto's disease, hidradenitis suppurativa, idiopathic thrombocytopenic purpura, interstitial cystitis, lupus erythematosus, morphea, multiple sclerosis, myasthenia gravis, narcolepsy, neuromyotonia, pemphigus vulgaris, pernicious anaemia, polymyositis, primary biliary cirrhosis, psoriasis, psoriatic arthritis, rheumatoid arthritis, schizophrenia, scleroderma, temporal arteritis, vasculitis, vitiligo, and wegener's granulomatosis.

It should be understood that the invention is not limited to the particular embodiments shown and described herein, but that various changes and modifications may be made without departing from the spirit and scope of the invention as defined by the claims.

General Synthetic Methods

The HDAC-inhibiting derivatives of camptothecin according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As an example, compounds with the formula

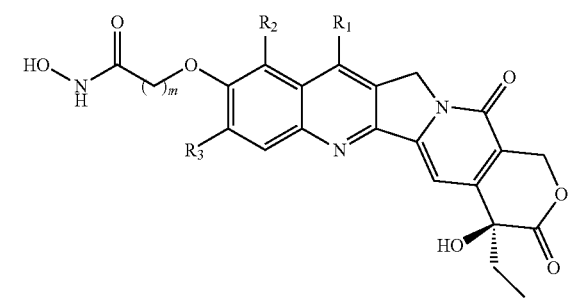

in which $R_1$, $R_2$, $R_3$, and m in general Scheme 1 are the same as those described in the Summary section above.

Scheme 1
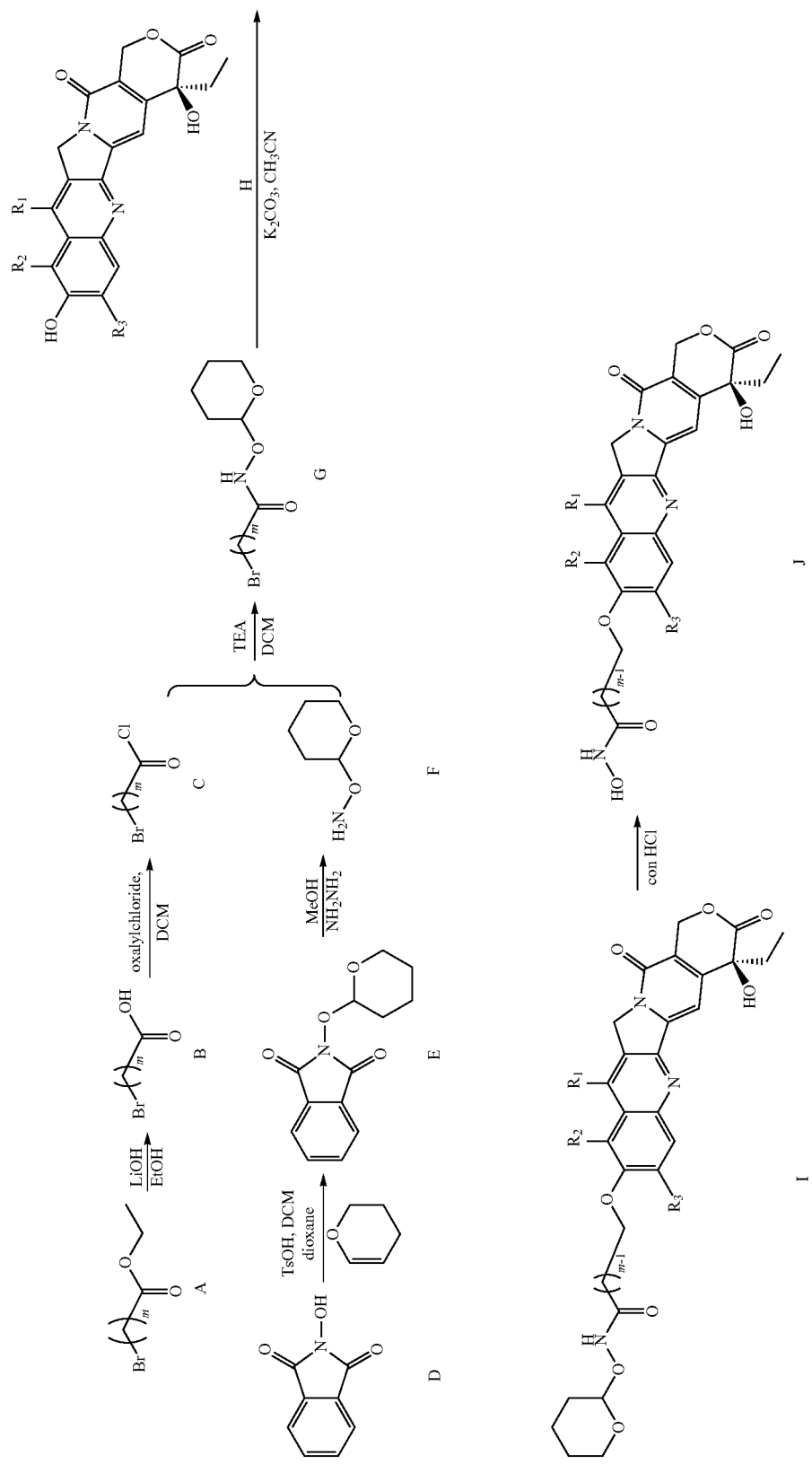

The starting material A is first converted into intermediate B and then intermediate C by standard organic reactions. After that, N-hydroxyphthalimide (D) can react with dihydropyran to afford intermediate (E) with high yield. The intermediate (E) can react with hydrazine in MeOH resulting intermediate (F), which will subsequently react with intermediate (C) to afford the key intermediate G. The coupling of G and Camptothecin H leads to intermediate I, which will undergo hydrolysis in acid to give the target product J.

In the Scheme 1, the key raw materials H may be commercially available. For example the compounds H-1 to H-10 in the following table are commercially available. For other starting materials H can be obtained by standard procedures of organic chemistry. For example, H-11 can be produced by etherization of the commercially available starting material H-1 (10-hydroxy-camptothecin) with alkyl bromide in the presence of a base (usually $K_2CO_3$) followed by a Claisen rearrangement. H-12 can be prepared by the reduction of the commercially available starting material H-5 with $H_2$ over $PtO_2$ in absolute ethanol.

H-1
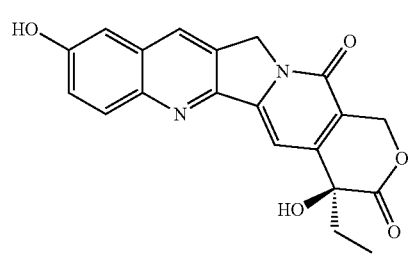

H-2
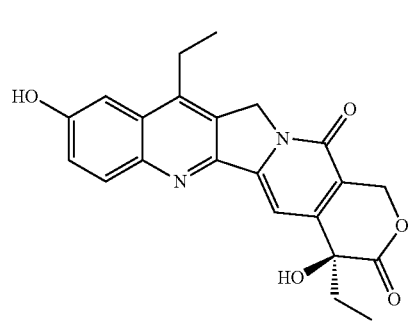

H-3
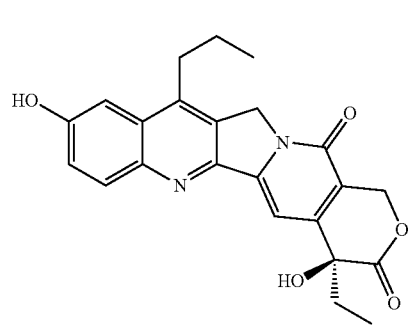

H-4
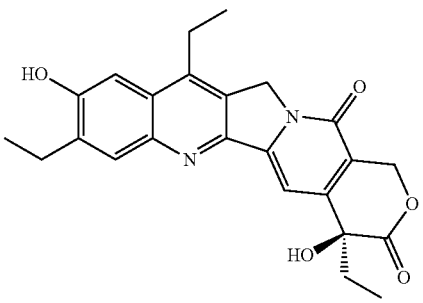

H-5
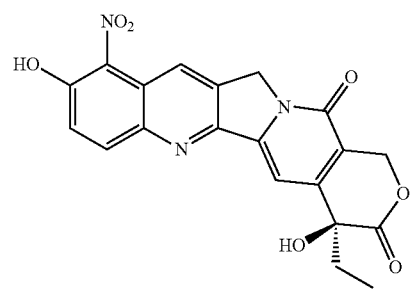

H-6
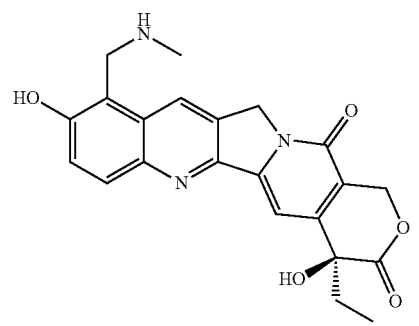

H-7
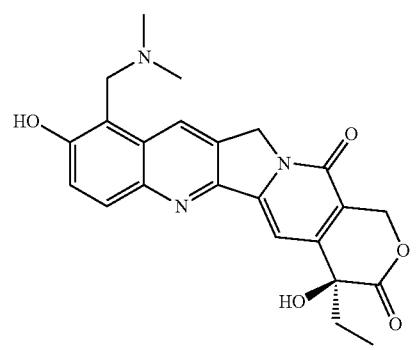

H-8
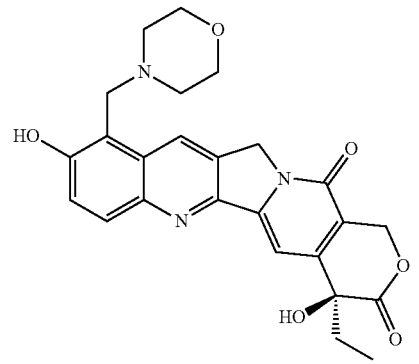

H-9
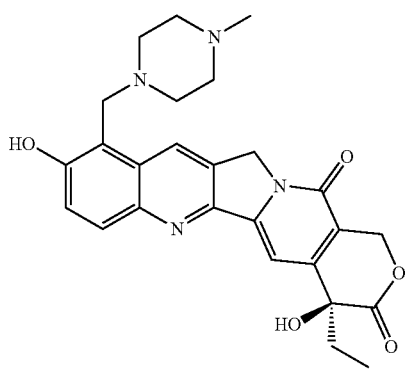

H-10
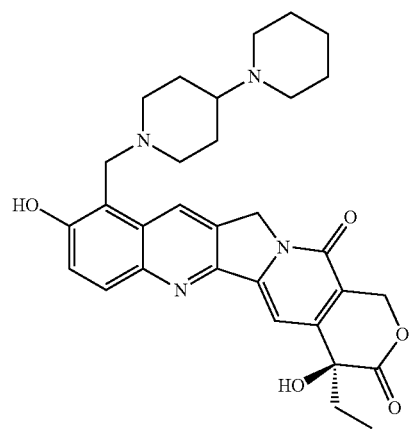

H-11
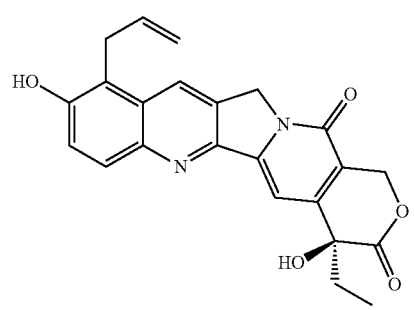

H-12
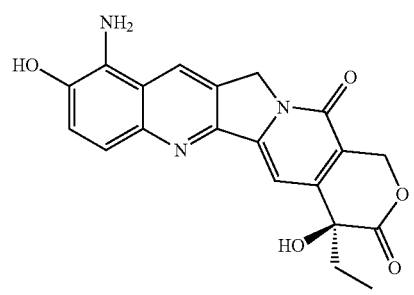

H-13
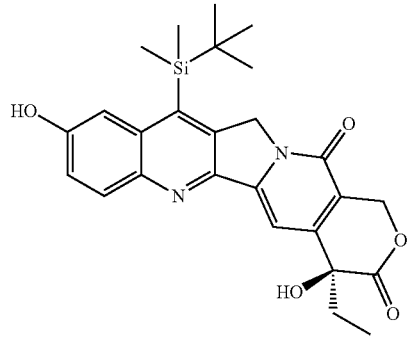

H-14
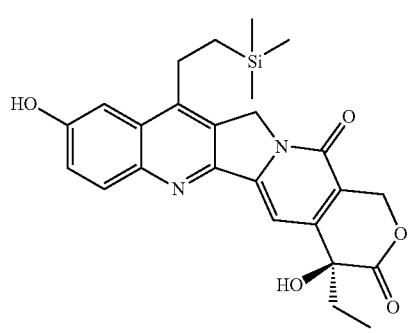

H-15
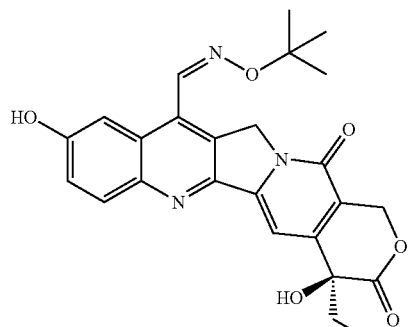

H-16
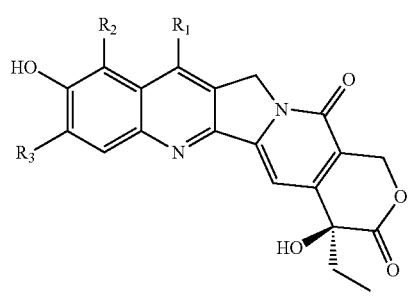

The raw material H-13 can be prepared according to the Scheme 2 below; the reaction of camptothecin with Tbdms-H, (t-BuO)$_2$ and t-BuSH in refluxing dioxane gives the 7-silylcamptothecin, which is treated with H$_2$O$_2$ in hot AcOH to give the N-oxide. Finally, this compound is isomerized by photolysis in dioxane/H$_2$SO$_4$ to afford the target silylated 10-hydroxycamptothecin (H-13).

Scheme 2

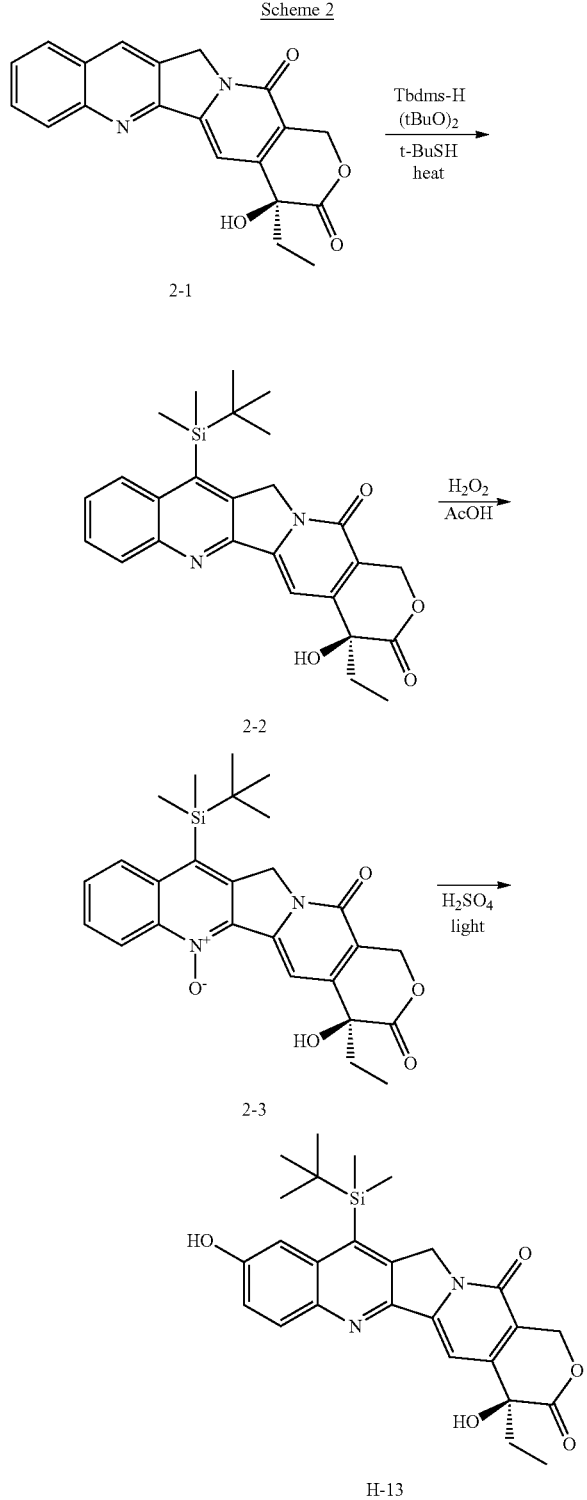

Scheme 3

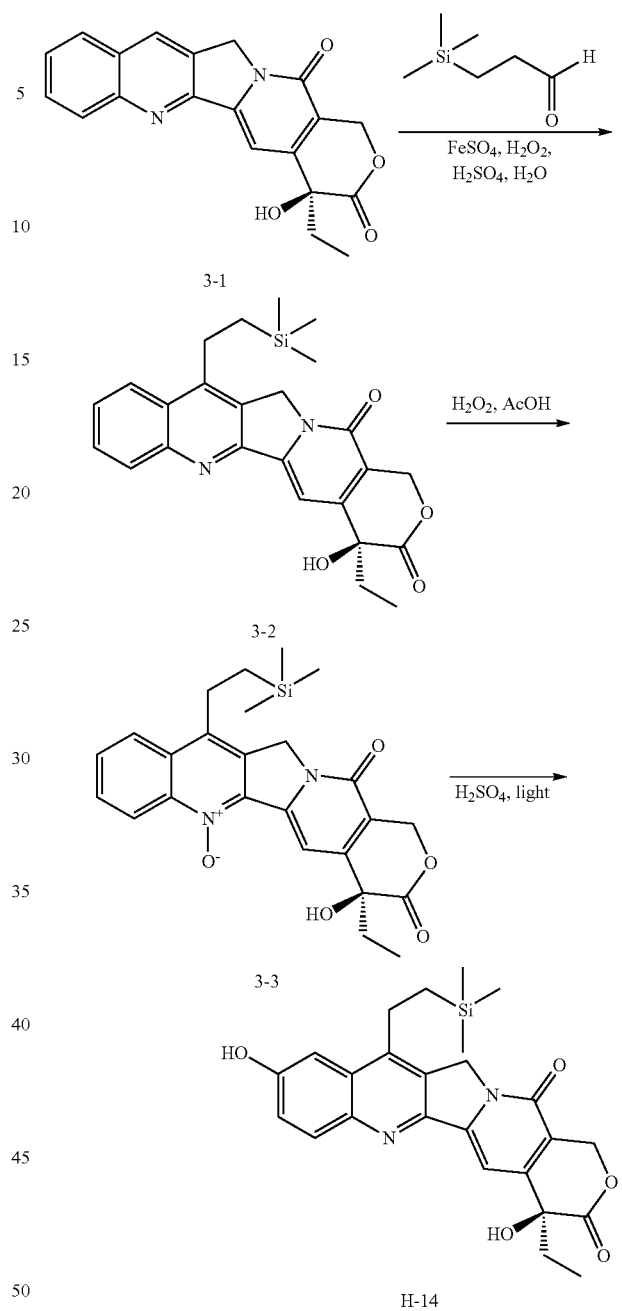

The raw material H-14 can be prepared according to the Scheme 3 below: The reaction of camptothecin with 3-(trimethylsilyl)propanal in the presence of $FeSO_4$ and $H_2O_2$ gives the 7-(2-trimethylsilylethyl)camptothecin, which is treated with $H_2O_2$ in hot AcOH to give the N-oxide. Finally, this compound is isomerized by photolysis in dioxane/$H_2SO_4$ to afford the target silylated 10-hydroxycamptothecin (H-14).

The raw material H-15 can be prepared according to the Scheme 4 below: The reaction of 10-hydroxycamptothecin (4-1) with $Ac_2O$ and pyridine gives the diacetate (intermediate 4-2). The radical alkylation of intermediate 4-2 with hydrogen peroxide and ferrous sulfate in methanolic sulfuric acid provides the 7-hydroxymethyl camptothecin (intermediate 4-3). Subsequent heating of intermediate 4-3 with acetic acid results in the formation of aldehyde (intermediate 4-4). A similar oxidation is observed by treatment of 7-hydroxymethyl camptothecin with other cationoid reagents, including $H_2SO_4$, $BF_3 \cdot Et_2O$, $POCl_3$, $SOCl_2$, TsCl and $PPh_3$-$CCl_4$. After that, the condensation of 7-aldehyde camptothecin with O-tert-butylhydroxylamine hydrochloride in ethanolic pyridine affords the corresponding oxime (intermediate 4-5). Finally, intermediate 4-5 is deacetylated by reaction with NaOMe in methanol or HCl in ethanol to afford the target compound (H-15).

Scheme 4

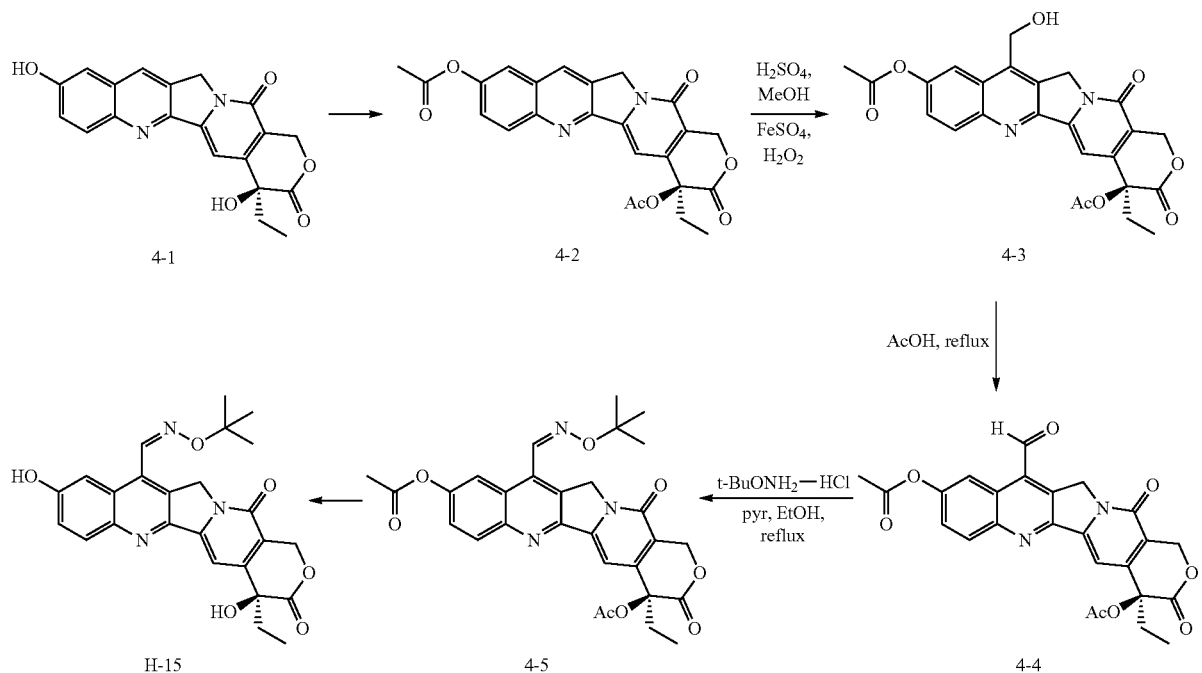

In general, the raw material H-16 can be prepared by the coupling of 5-A and the tricyclic triketone (5-B), as shown in Scheme 5. The 5-A can be prepared by the standard procedures of organic chemistry, in which the protecting group could be the Silyl ethers. The tricyclic triketone 5-B can be synthesized according to the paper of J Org Chem, 1997, 62(19): 6588.

Scheme 5

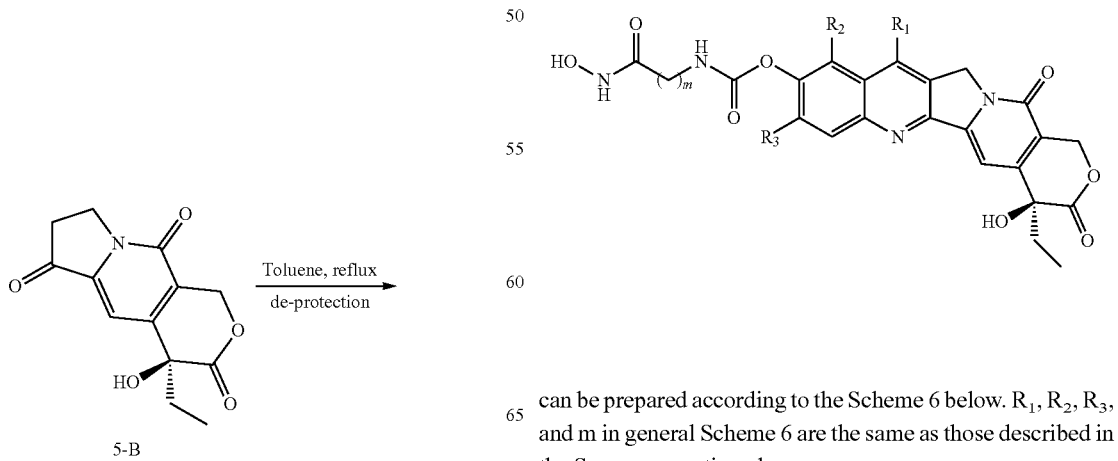

As another example, compounds with the general formula

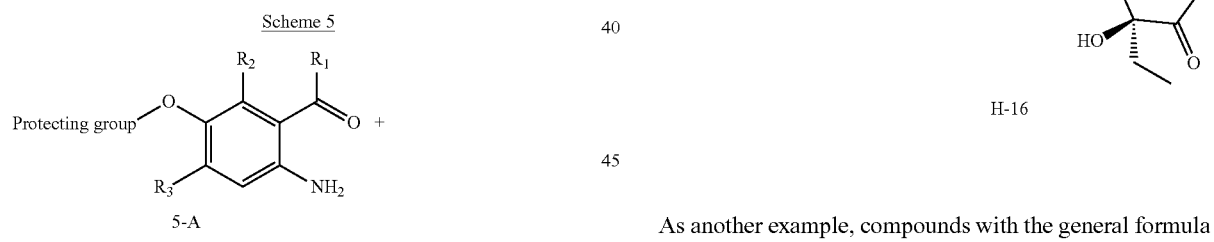

can be prepared according to the Scheme 6 below. $R_1$, $R_2$, $R_3$, and m in general Scheme 6 are the same as those described in the Summary section above.

Scheme 6

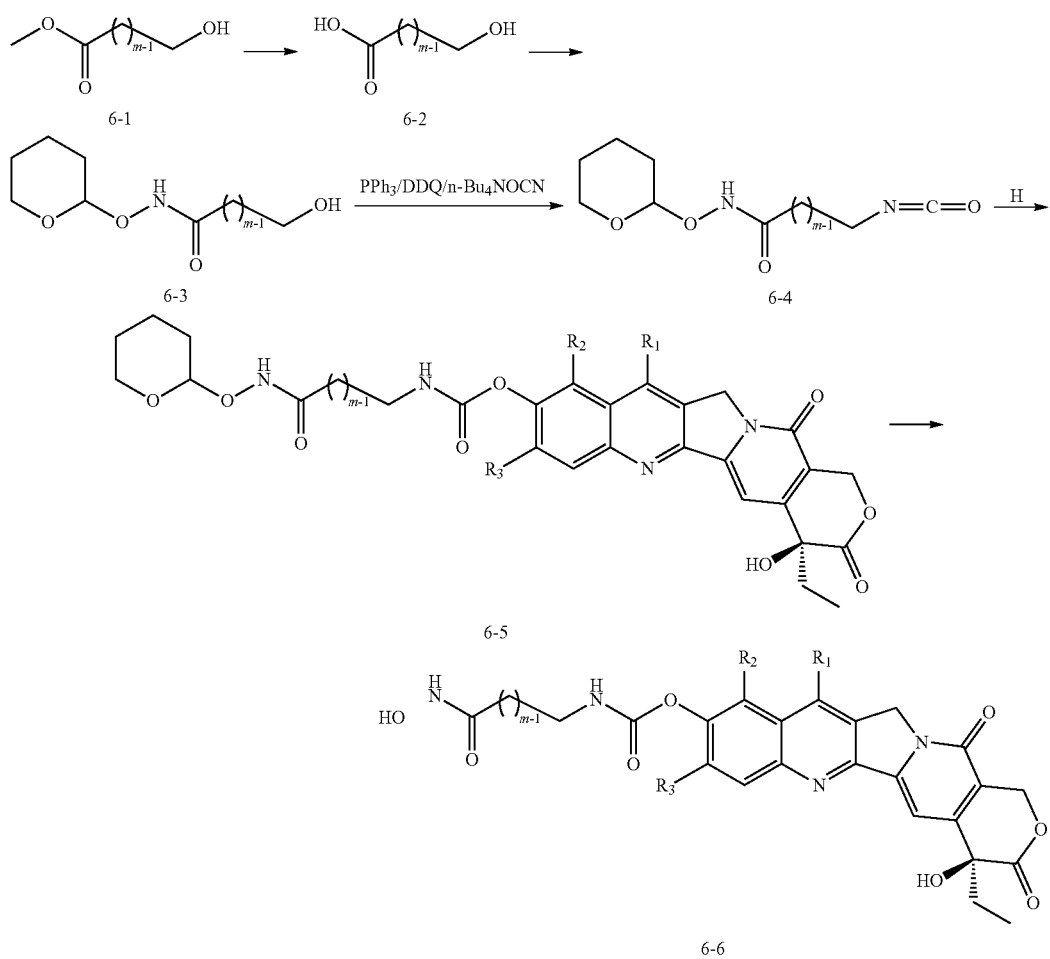

The starting material 6-1 is first hydrolyzed to intermediate 6-2, which can couple with O-(tetrahydro-2H-pyran-2-yl) hydroxylamine to afford alcohol intermediate 6-3. After that, the alcohol intermediate 6-3 will be converted to the isocyanate intermediate 6-4 according the method reported by B. Akhlaghinia (*Synthesis*, 2005, 1955-1958). The coupling of 6-4 and Camptothecin H leads to intermediate 6-5, which will undergo hydrolysis in acid to give the target product 6-6.

Alternatively, isocyanate intermediate 6-4 can be prepared according to the Scheme 6A below. The starting material 6A-1 can couple with O-(tetrahydro-2H-pyran-2-yl)hydroxylamine followed by an amine deprotection process to afford intermediate 6A-2, which can be subsequently converted to 6-4 by standard organic reaction.

Scheme 6A

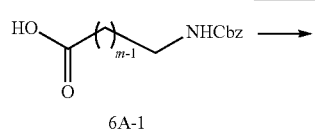

-continued

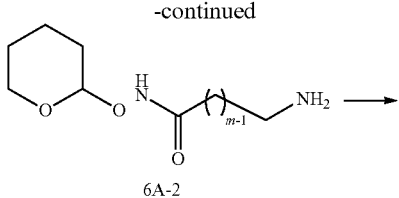

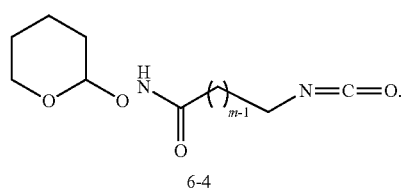

As another example, compounds with the general formula
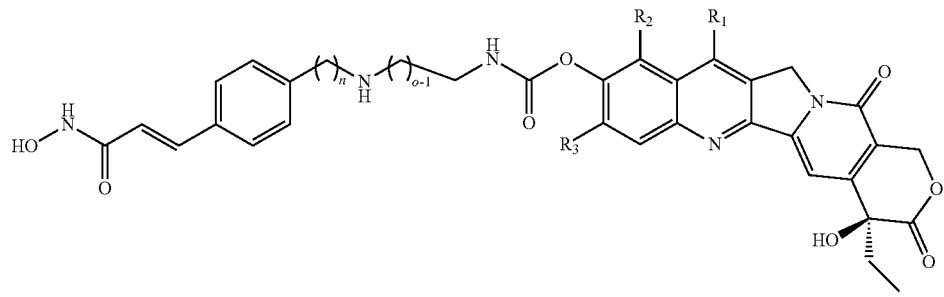
can be prepared according to general Scheme 7 below. n, o, $R_1$, $R_2$, and $R_3$ in general Scheme 7 are the same as those described in the Summary section above.
Scheme 7
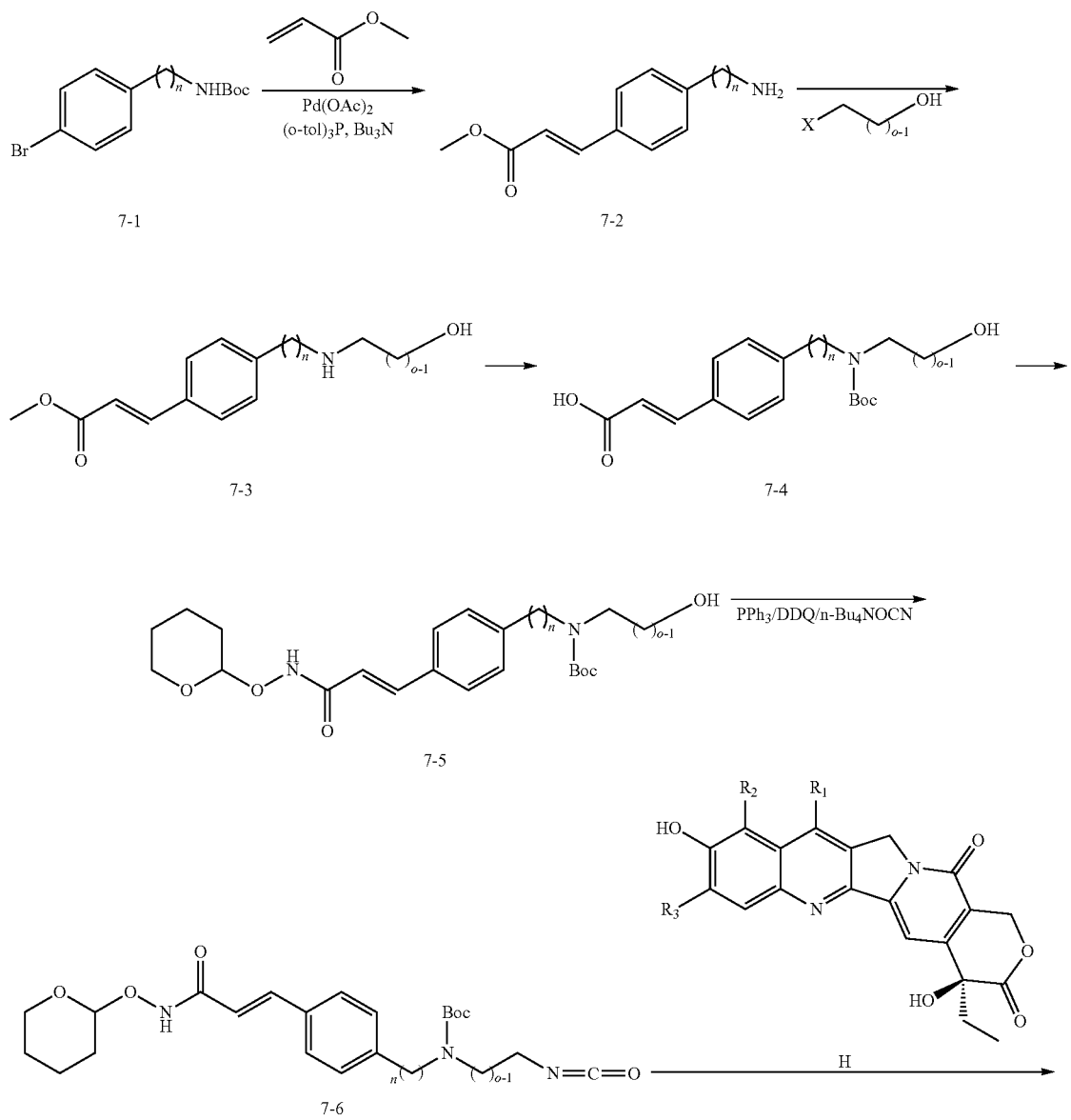

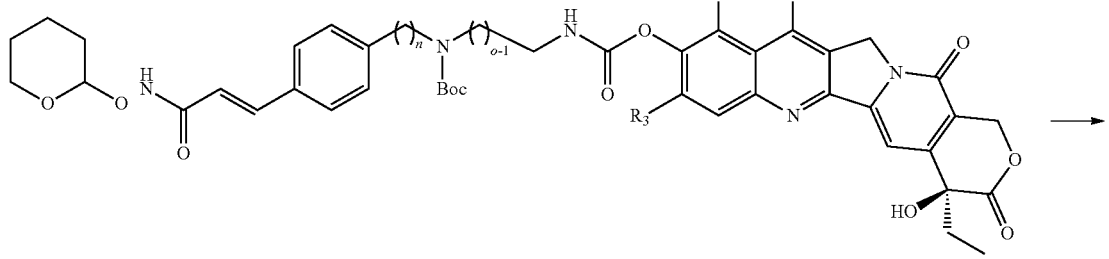

7-7

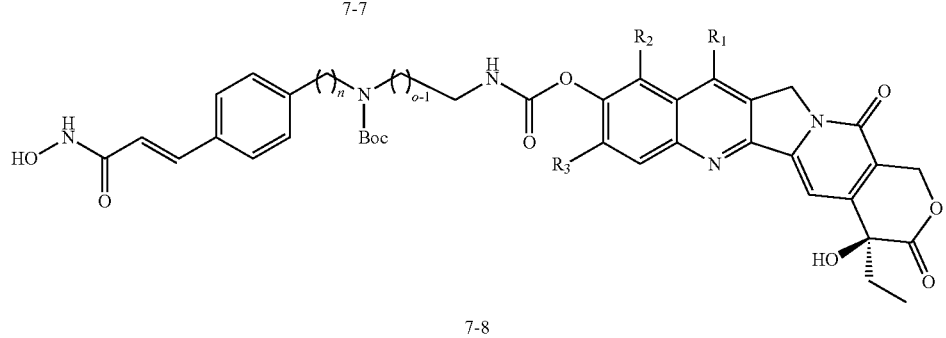

7-8

The cinnamate intermediate 7-2 can be prepared by a Pd-catalyzed coupling of methyl acrylate with the starting material 7-1 followed by the deprotection of amine group. After that Intermediate 7-2 will react with an appropriate haloalcohol to afford intermediate 7-3, which will undergo hydrolysis and then and then the amine is protected to yield carboxylic acid intermediate 7-4. Intermediate 7-4 can couple with O-(tetrahydro-2H-pyran-2-yl)hydroxylamine to afford alcohol intermediate 7-5, which can be converted to the isocyanate intermediate 7-6 according the method reported by B. Akhlaghinia (*Synthesis,* 2005, 1955-1958). The coupling of 7-5 and Camptothecin H leads to intermediate 7-7, which will undergo hydrolysis in acid to give the target product 7-8.

Alternatively, isocyanate intermediate 7-6 can be prepared according to the Scheme 7A below. The cinnamate intermediate 7A-2 can be prepared by a Pd-catalyzed coupling of methyl acrylate with the starting material 7A-1. After that Intermediate 7A-2 can undergo a hydrolysis to afford 7A-3, which can couple with O-(tetrahydro-2H-pyran-2-yl)hydroxylamine to afford intermediate 7A-4. The intermediate 7A-4 will undergo a deprotection process thereby yielding intermediate 7A-5, which will react with an appropriate haloalkyl ester to afford intermediate 7A-6. After a protection and a deprotection process, intermediate 7A-6 can be converted to intermediate 7A-7, which can be subsequently converted to isocyanate 7-6 by standard organic reaction.

Scheme 7A

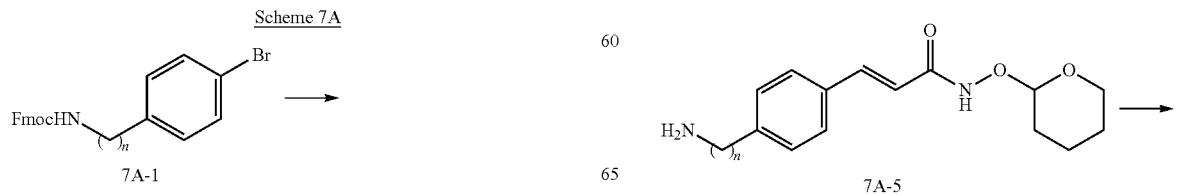

7A-1

-continued

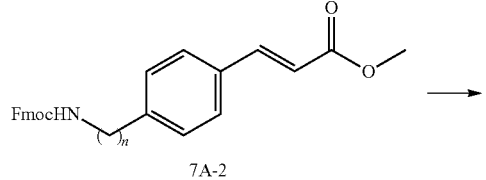

7A-2

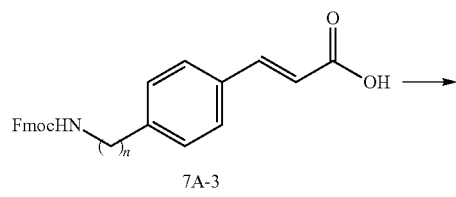

7A-3

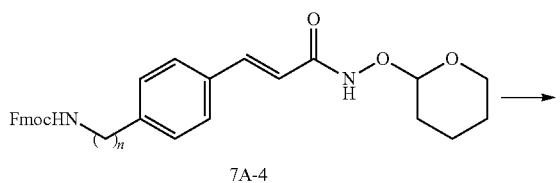

7A-4

H₂N 7A-5

75
-continued
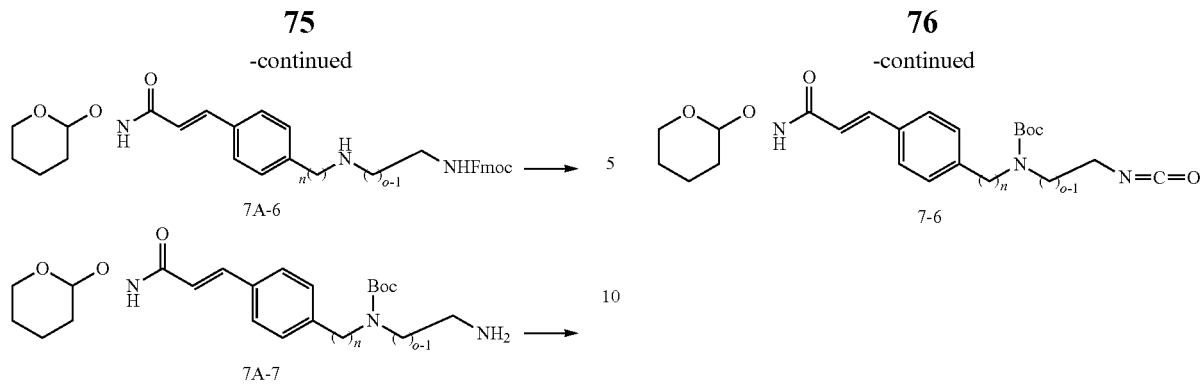
As another example, compounds with the general formula
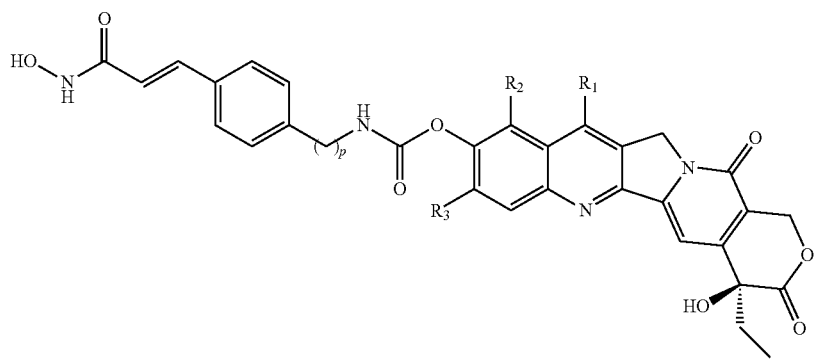
can be prepared according to general Scheme 7B. p, $R_1$, $R_2$, and $R_3$ in Scheme 7B are the same as those described in the Summary section above.
Scheme 7B
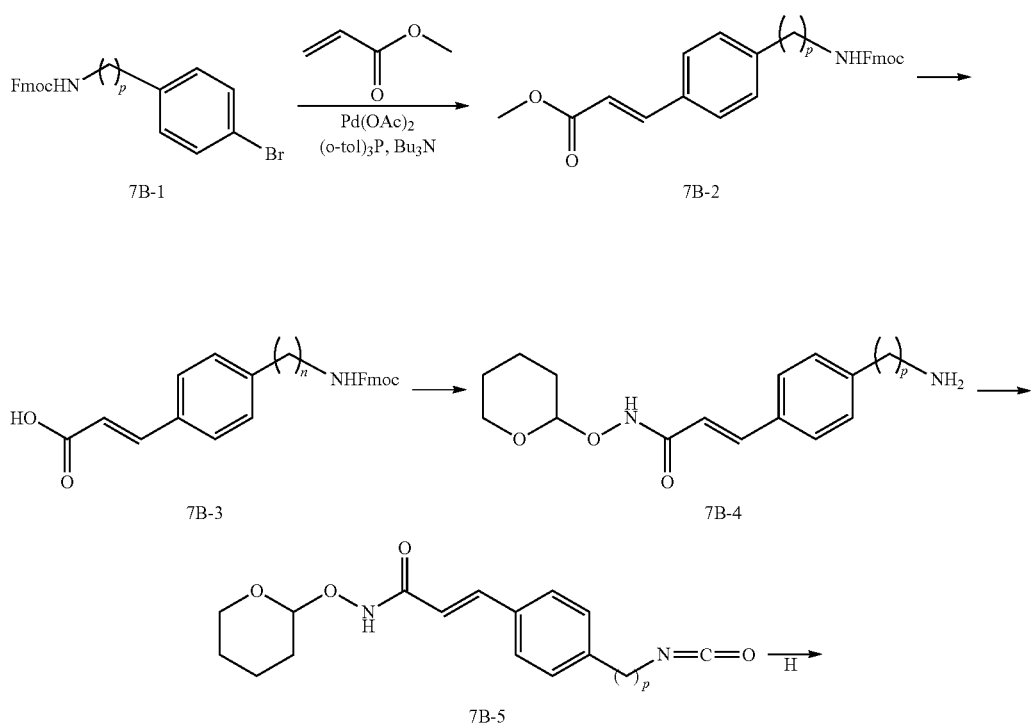

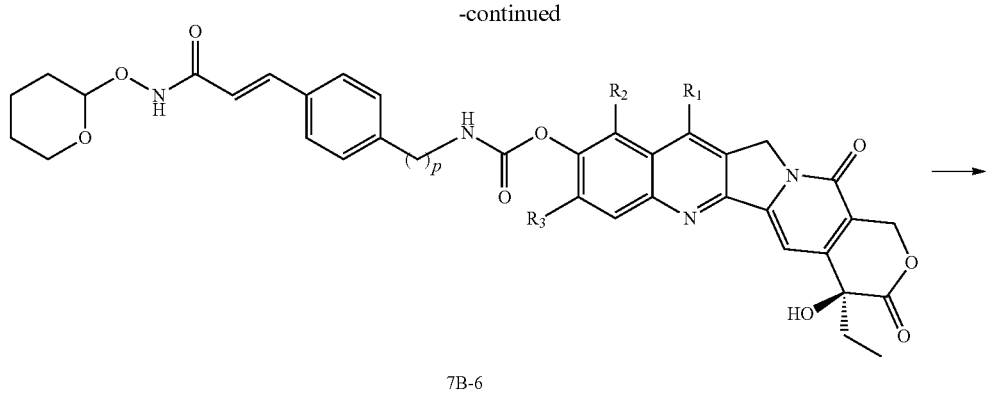

7B-6

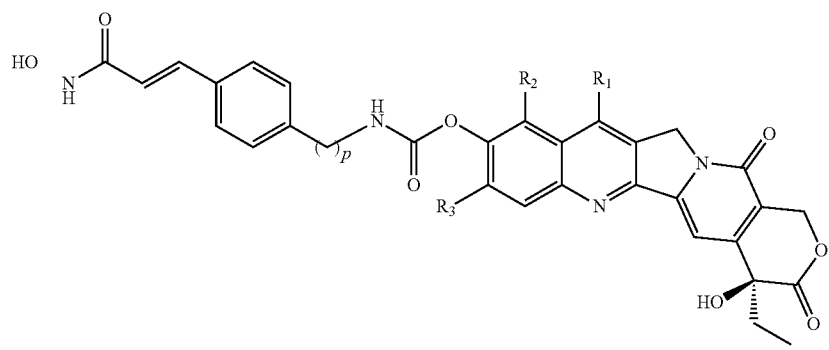

7B-7

The cinnamate intermediate 7B-2 can be prepared by a Pd-catalyzed coupling of methyl acrylate with the starting material 7B-1. After that Intermediate 7B-2 will undergo hydrolysis yielding carboxylic acid intermediate 7B-3, which can couple with O-(tetrahydro-2H-pyran-2-yl)hydroxylamine and de-protect the amine protecting group to afford alcohol intermediate 7B-4. Intermediate 7B-4 can be converted to the isocyanate intermediate 7B-5 by standard organic reaction. The coupling of 7B-5 and Camptothecin H leads to intermediate 7B-6, which will undergo hydrolysis in acid to give the target product 7B-7.

As another example, compounds with the general formula

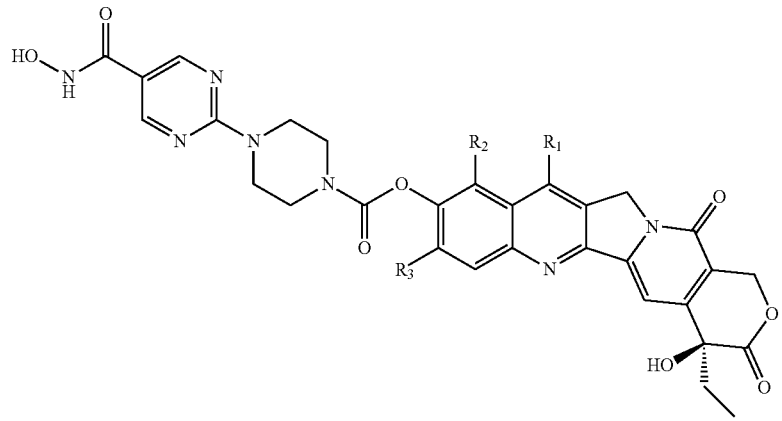

can be prepared according to general Scheme 8 below. $R_1$, $R_2$, and $R_3$ in general Scheme 8 are the same as those described in the Summary section above.
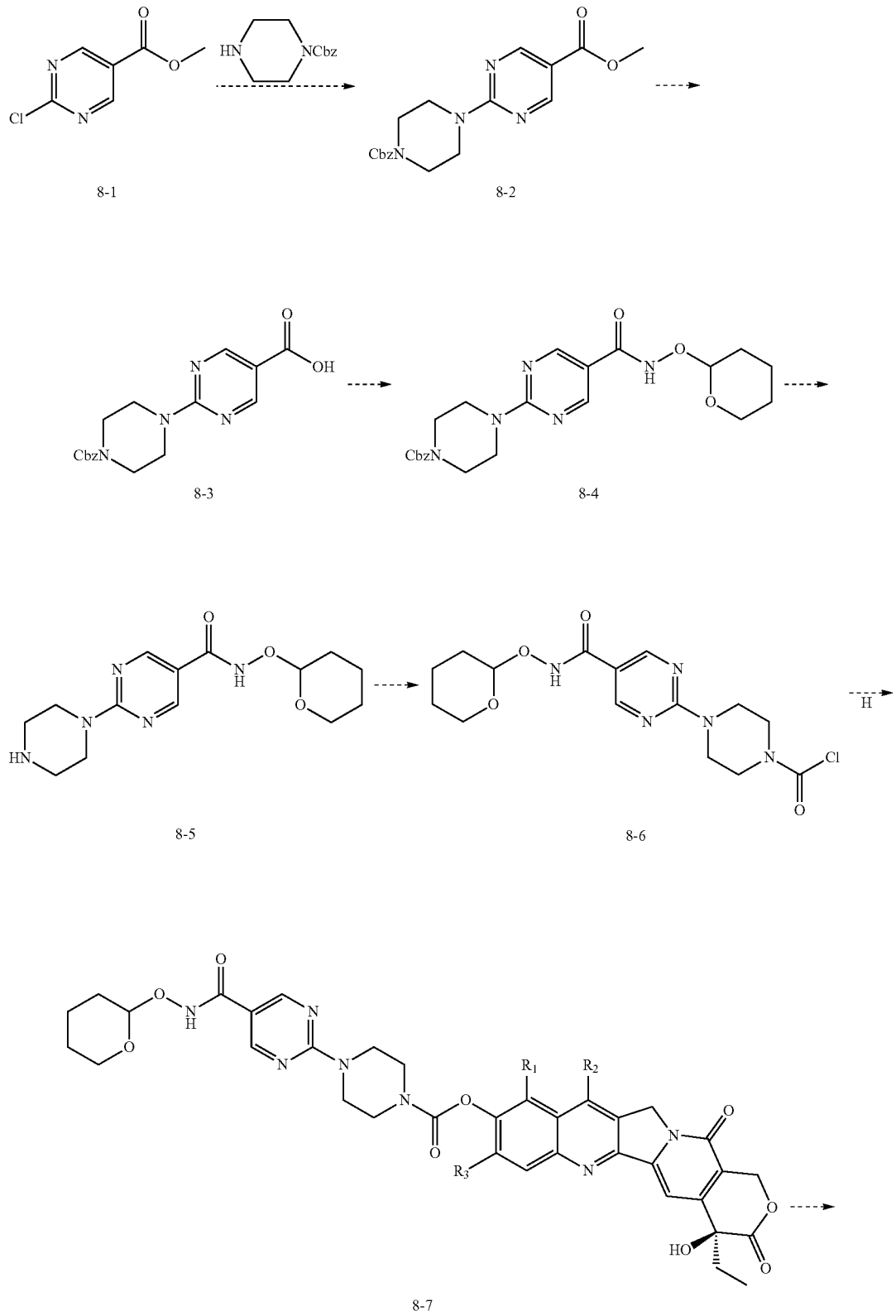

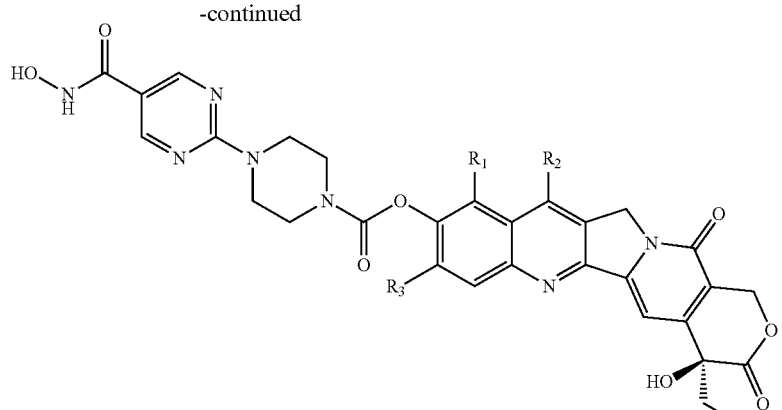

8-8

The starting material 8-1 is first converted into intermediate 8-2 and then intermediate 8-3 by standard organic reactions. After that, 8-3 can couple with O-(tetrahydro-2H-pyran-2-yl)hydroxylamine to afford intermediate 8-4, which will undergo a deprotection process thereby yielding key intermediate 8-5. The intermediate 8-5 will be then converted to an acyl chloride intermediate 8-6. The coupling of 8-6 and Camptothecin H leads to intermediate 8-7, which will undergo hydrolysis in acid to give the target product 8-8.

As another example, compounds with the general formula

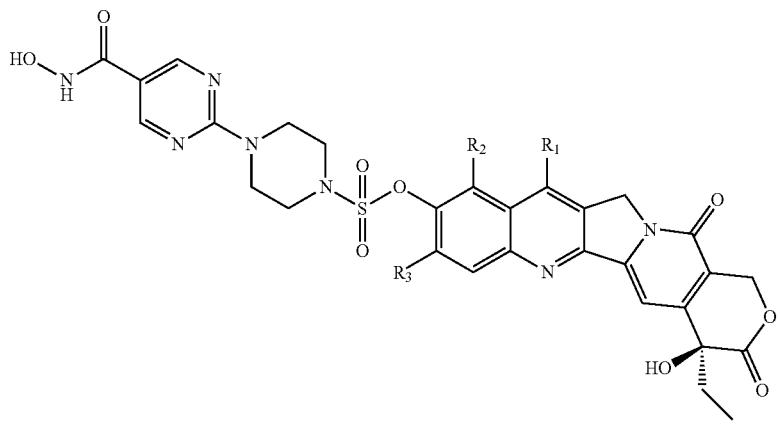

can be prepared according to general Scheme 8A. $R_1$, $R_2$, and $R_3$ in general Scheme 8A are the same as those described in the Summary section above.

Scheme 8A

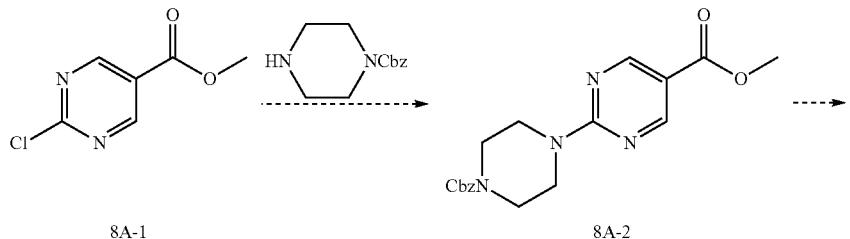

8A-1         8A-2

-continued
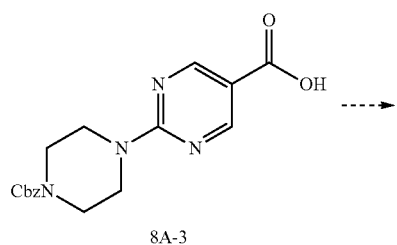
8A-3
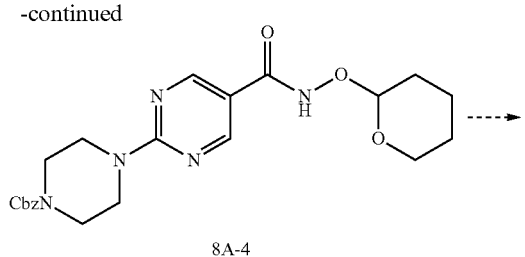
8A-4
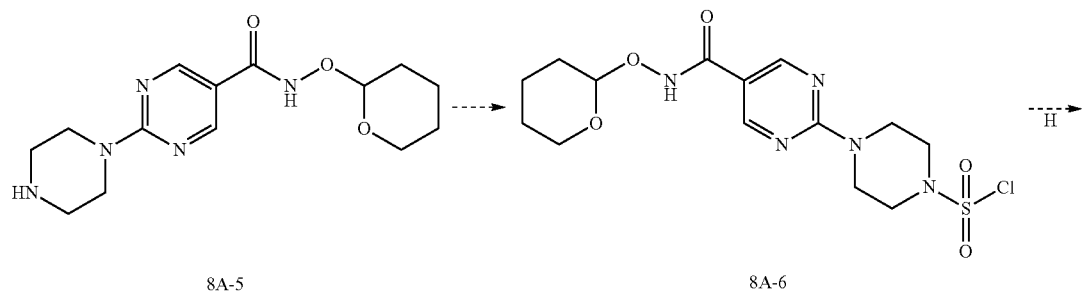
8A-5
8A-6
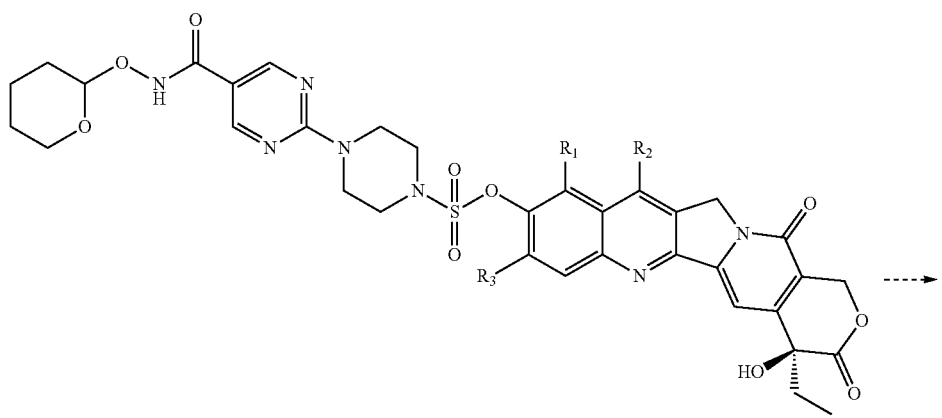
8A-7
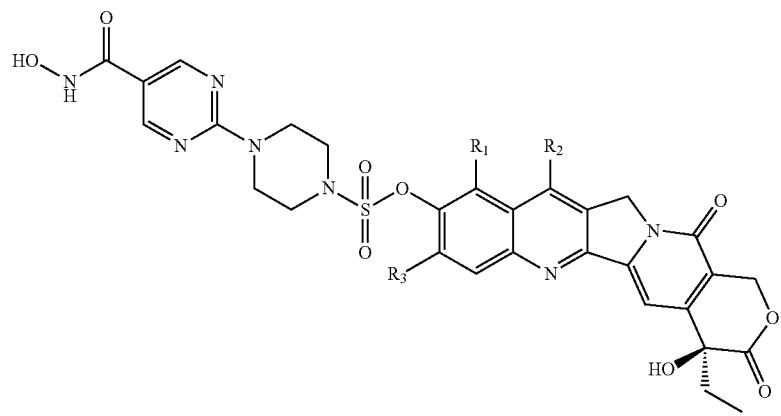
8A-8

The starting material 8A-1 is first converted into intermediate 8A-2 and then intermediate 8A-3 by standard organic reactions. After that, 8A-3 can couple with O-(tetrahydro-2H-pyran-2-yl)hydroxylamine to afford intermediate 8A-4, which will undergo a deprotection process thereby yielding key intermediate 8A-5. The intermediate 8A-5 will be then converted to an sulfonyl chloride intermediate 8A-6. The coupling of 8A-6 and Camptothecin H leads to intermediate 8A-7, which will undergo hydrolysis in acid to give the target product 8A-8.

As another example, compounds with the general formula

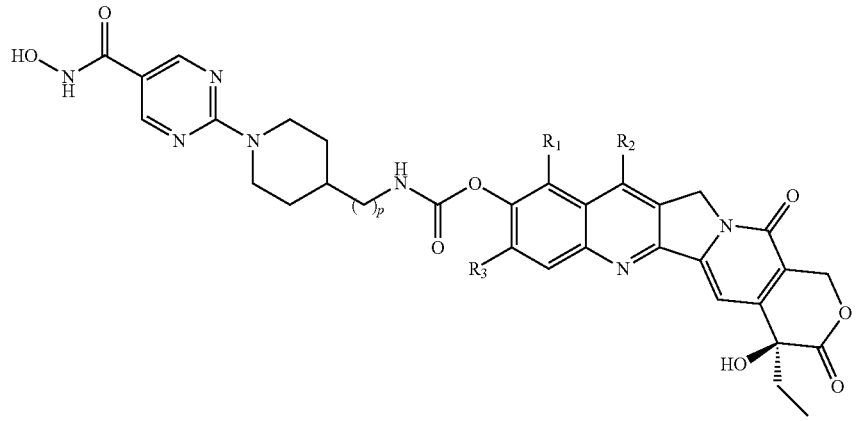

can be prepared according to general Scheme 8B. $R_1$, $R_2$, and $R_3$ in general Scheme 8B are the same as those described in the Summary section above.

Scheme 8B

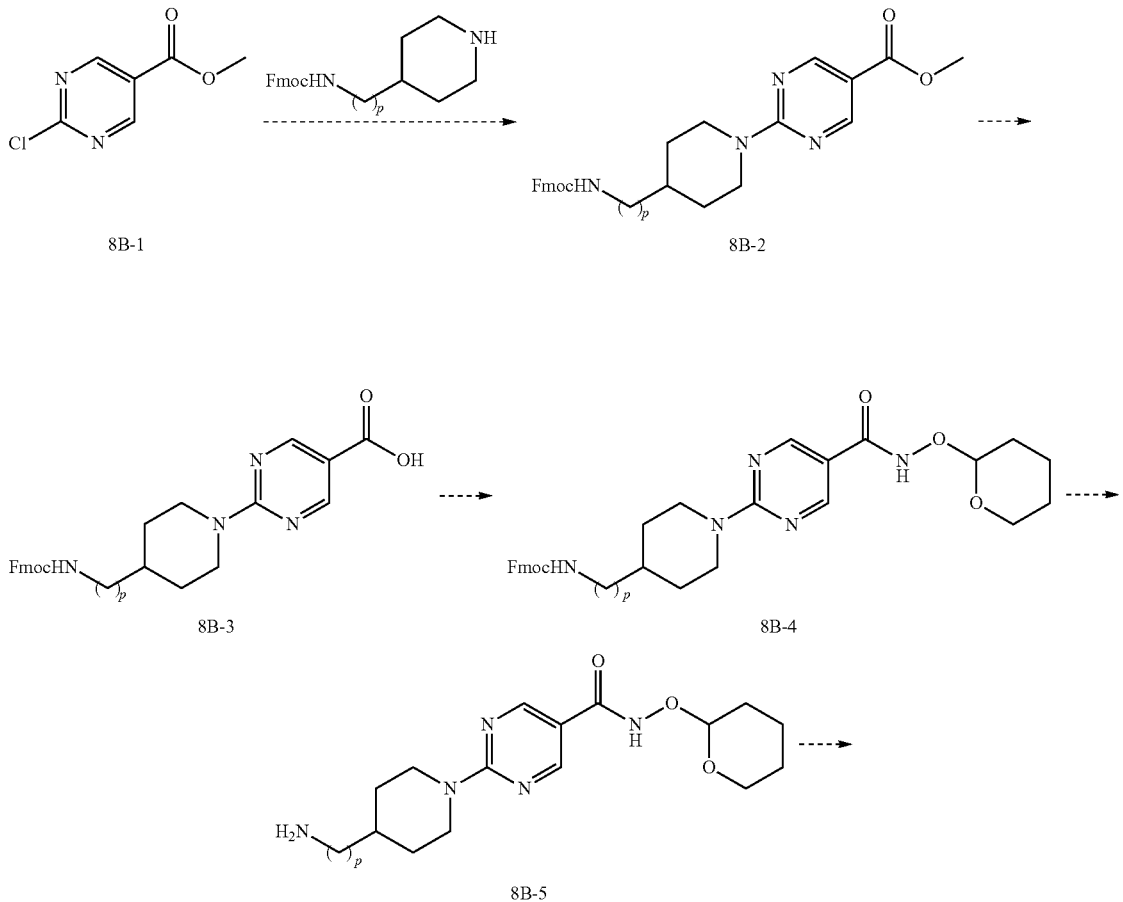

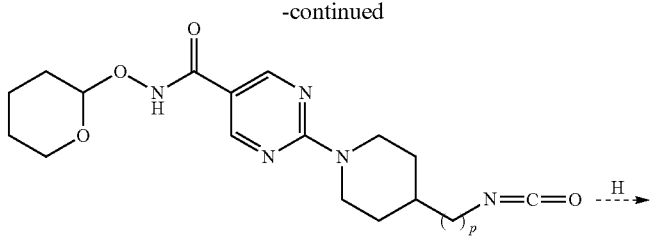

8B-6

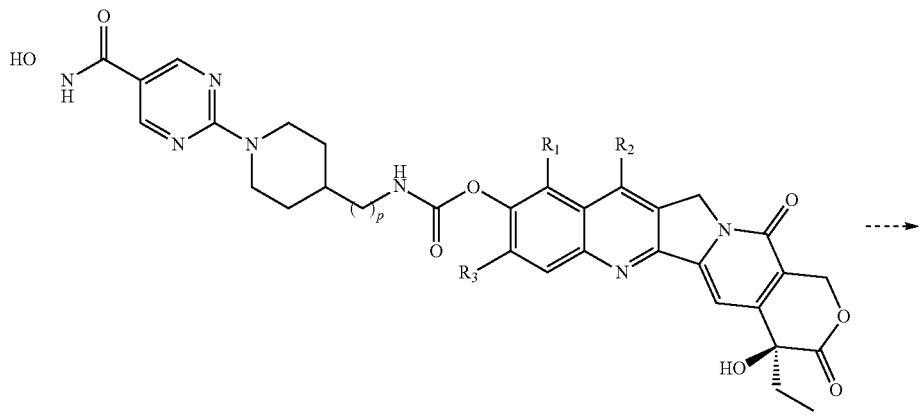

8B-7

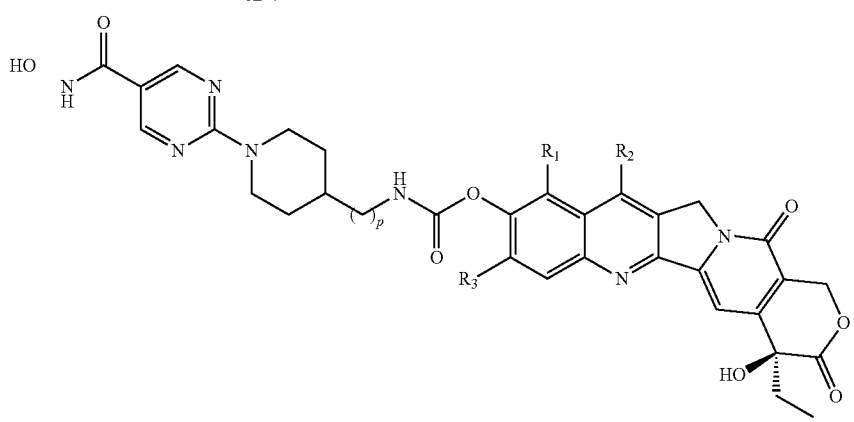

8B-8

The starting material 8B-1 is first converted into intermediate 8B-2 and then intermediate 8B-3 by standard organic reactions. After that, 8B-3 can couple with O-(tetrahydro-2H-pyran-2-yl)hydroxylamine to afford intermediate 8B-4, which will undergo a deprotection process thereby yielding key intermediate 8B-5. The intermediate 8B-5 will be then converted to an isocyanate intermediate 8B-6. The coupling of 8B-6 and Camptothecin H leads to intermediate 8B-7, which will undergo hydrolysis in acid to give the target product 8B-8.

EXAMPLES

Where NMR data were presented, $^1$H NMR and $^{13}$C NMR spectra were recorded on a Bruker Avance III (500 MHz $^1$H, 125 MHz $^{13}$C) with DCH Cryo-Probe. Chemical shift values (δ) were reported in ppm relative to CDCl$_3$ [δ 7.26 ppm (1H), 77.16 ppm ($^{13}$C)]. The proton spectra were reported as follows δ (multiplicity, number of protons). Multiplicities were indicated by s (singlet), d (doublet), t (triplet), q (quartet), p (pentet), h (heptet), m (multiplet) and br (broad).

Where HPLC data were presented, analyses were performed using an Agilent 1100 system. Alltima C18, 4.6×250 mm, 5 mm, gradient; Samples were eluted using a linear gradient of 0-100% acetonitrile, 30 minutes with a flow rate of 1 mL/min Chromatograms were generated at 230-400 nm using a diode array detector.

Where LC/MS data were presented, samples were analyzed by LC-MS/MS using an Agilent 6410 mass spectrometer coupled with an Agilent 1200 HPLC and a CTC PAL chilled auto sampler, all controlled by MassHunter software (Agilent).

Example 1

Synthesis of CY-700, a First-in-Class Dual-Functional Semisynthetic Camptothecin/HDAC inhibitor

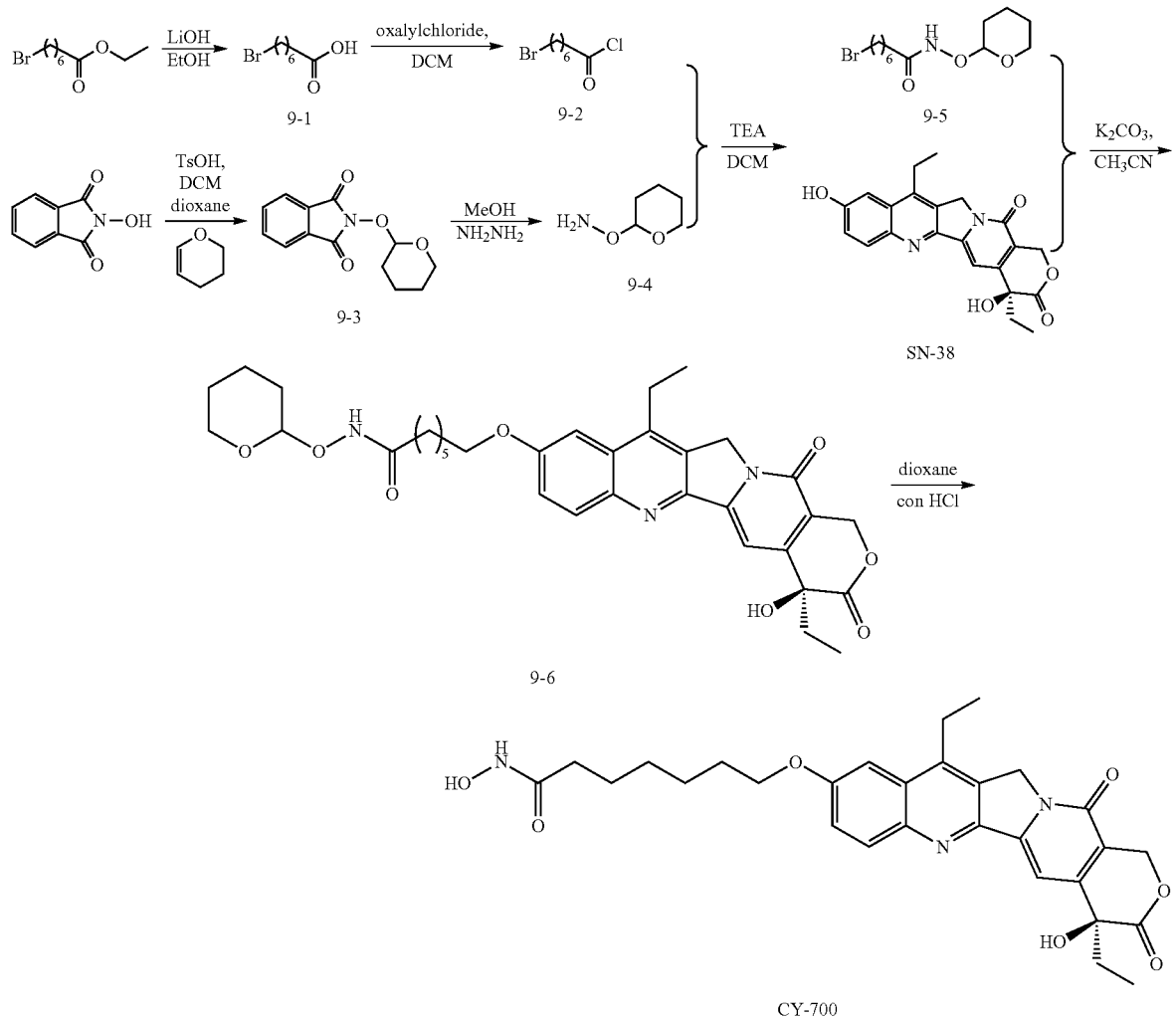

Synthesis of 9-1: to a solution of ethyl 7-bromoheptanoate (2.0 g, 8.43 mmol, 1 eq) in EtOH (15 mL) and $H_2O$ (10 mL) was added LiOH (2.0 g, 83.3 mmol, 10 eq). The mixture was stirred overnight at room temperature. The mixture was neutralized with 2N aqueous HCl with cooling in an ice-water bath, and the mixture was extracted with EtOAc. The EtOAc layer was separated, washed with water and brine, and dried over $Na_2SO_4$. Filtration and concentration in vacuo gave 1.7 g (96%) of the 7-Bromoheptanoic acid as a white solid.

Synthesis of 9-2: to a suspension of 7-bromoheptanoic acid (1.7 g, 8.13 mmol) obtained above in $CH_2Cl_2$ (30 mL) were added oxalylchloride (2.13 mL, 24.39 mmol) and a catalytic amount of DMF. The mixture was stirred overnight at room temperature. The solvent was removed by evaporation in vacuo to give 1.84 g (100%) of the 7-bromoheptanoyl chloride as a yellow solid.

Synthesis of 9-3: to a vigorously stirred solution of N-hydroxyphthalimide (10.0 g, 61.4 mmol) in $CH_2Cl_2$ (70 mL) and dioxane (80 mL) was added dihydropyran (6.16 mL, 67.6 mmol) and p-toluenesulfonic acid (200 mg). The resulting solution was stirred overnight at room temperature. The reaction was quenched by slow addition of saturated $NaHCO_3$ (100 mL). After separation, the organic layer was washed with brine and dried over $Na_2SO_4$. Solvent removal under vacuum yielded 13.4 g (88%) of 2-(tetrahydro-2H-pyran-2-yloxy)isoindoline-1,3-dione as a white solid.

Synthesis of 9-4: to a solution of 2-(tetrahydro-2H-pyran-2-yloxy)isoindoline-1,3-dione (13.4 g, 54.25 mmol, 1.00 equiv) in MeOH (200 mL) was added hydrazine (6 mL). The resulting solution was stirred for 30 mins at 60° C. in an oil bath. The reaction mixture was cooled with a water/ice bath. The solids were filtered out. The resulting mixture was concentrated under vacuum. This resulted in 5.6 g (88%) of $H_2N$-OTHP as a colorless oil witch solidified upon storage at 4° C.

Synthesis of 9-5: to a solution of H₂N-OTHP (1.0 g, 8.54 mmol) and triethylamine (2.46 g, 24.39 mmol) in CH₂Cl₂ (20 mL) was added a solution of 7-bromoheptanoyl chloride (1.84 g, 8.13 mmol) obtained above in CH₂Cl₂ (10 mL) dropwise cooling in an ice-water bath. The mixture was stirred at room temperature for 1 h. It was diluted with EtOAc and washed with aqueous saturated NaHCO3, water, and brine, before being dried over MgSO₄. Filtration and concentration in vacuo and purification by silica gel flash chromatography (n-hexane/EtOAc=3/1) gave 1.3 g (52%) of 7-bromo-N-(tetrahydro-2H-pyran-2-yloxy)-heptanamide as yellow solid.

Synthesis of 9-6: to a suspension in dry CH₃CN of SN-38 (1.0 g, 2.55 mmol) and potassium carbonate (1.0 g, 7.24 mmol) was added H₂N-OTHP (1.0 g, 3.24 mmol), and the reaction mixture was stirred for 18 h at 60° C. The reaction mixture was diluted with EtOAc (500 mL) and filtered, the organic phase was concentrated in vacuo and purification by silica gel flash chromatography (MeOH/EtOAc=1/30) to give 250 mg (16%) of Compound 6 as a yellow solid.

Synthesis of CY-700: to a solution of Compound 6 (250 mg, 0.4 mmol) in dioxane (15 mL) was added 5 mL con.HCl. The resulting solution was stirred for 1 h at room temperature. The reaction mixture was concentrated in vacuo. The residue was recrystallized with MeOH/Et2O, this resulted in ~60 mg (28%) of CY-301 as a yellow solid. Purity>95%, HNMR (300 MHz, CD3OD, ppm): δ8.03 (1H, d), 7.59 (1H s), 7.47-7.39 (2H m), 5.24 (2H s), 4.19-4.15 (2H m), 3.22-3.20 (2H m), 2.18-2.15 (2H m), 1.98-1.30 (12H m), 1.25-1.21 (3H t), 1.11-0.99 (3H t); LCMS: 536 [MH⁺].

The following compounds were prepared by methods analogous to those disclosed in Scheme 1, 6, 7, 7B, 8, 8A, and 8B:

| ID | Structure | m/z(MH⁺) |
|---|---|---|
| 701 | 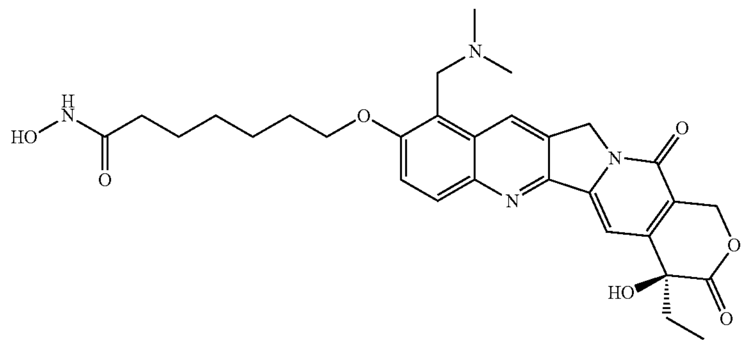 [SMILES: CC[C@@]1(O)C(=O)OCc2c1cc1n(c2=O)Cc2cc3c(CN(C)C)c(OCCCCCCC(=O)NO)ccc3nc2-1] | 565 |
| 702 | 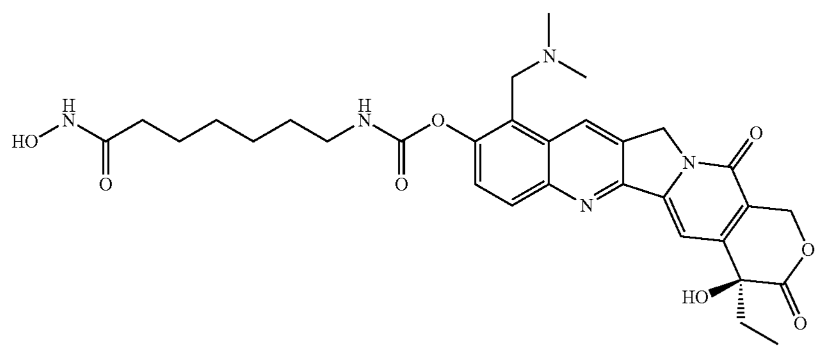 [SMILES: CC[C@@]1(O)C(=O)OCc2c1cc1n(c2=O)Cc2cc3c(CN(C)C)c(OC(=O)NCCCCCCC(=O)NO)ccc3nc2-1] | 608 |
| 703 | 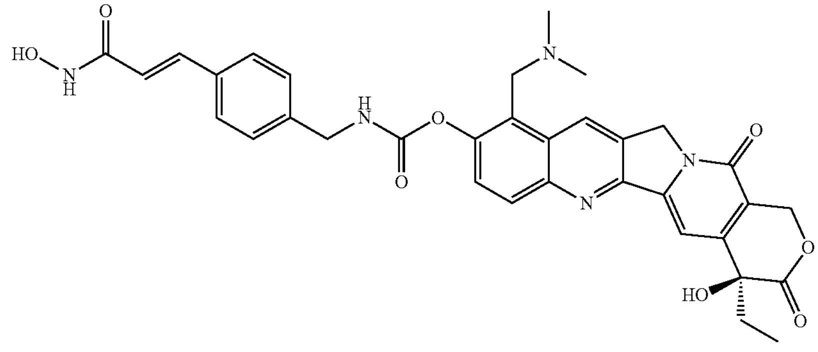 [SMILES: CC[C@@]1(O)C(=O)OCc2c1cc1n(c2=O)Cc2cc3c(CN(C)C)c(OC(=O)NCc4ccc(/C=C/C(=O)NO)cc4)ccc3nc2-1] | 640 |

| ID | Structure | m/z(MH+) |
|---|---|---|
| 704 | 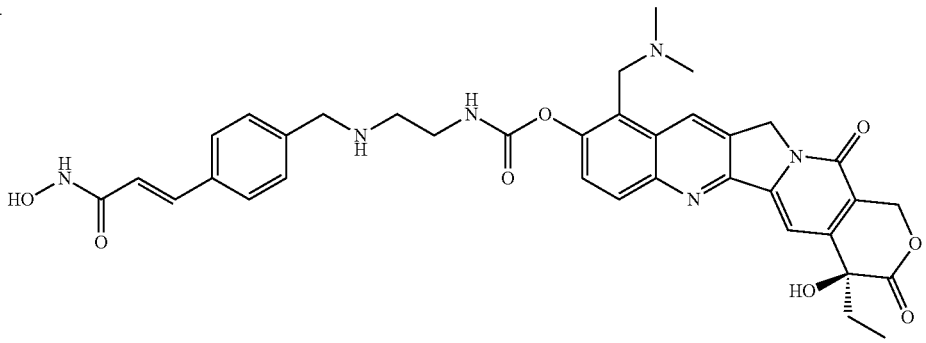 [SMILES: CC[C@@]1(O)C(=O)OCc2c1cc1n(c2=O)Cc2cc3c(CN(C)C)c(OC(=O)NCCNCc4ccc(/C=C/C(=O)NO)cc4)ccc3nc2-1] | 683 |
| 705 | 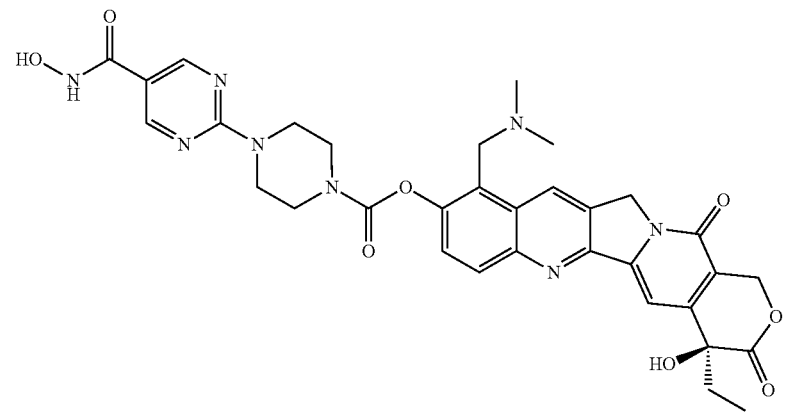 [SMILES: CC[C@@]1(O)C(=O)OCc2c1cc1n(c2=O)Cc2cc3c(CN(C)C)c(OC(=O)N4CCN(c5ncc(C(=O)NO)cn5)CC4)ccc3nc2-1] | 671 |
| 706 | 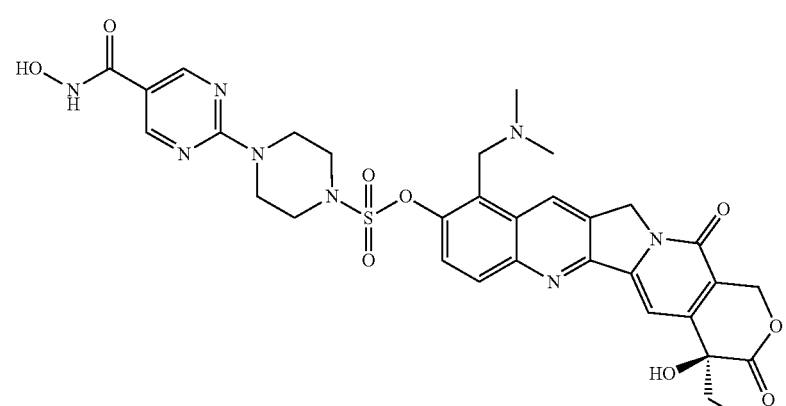 | 708 |
| 707 | 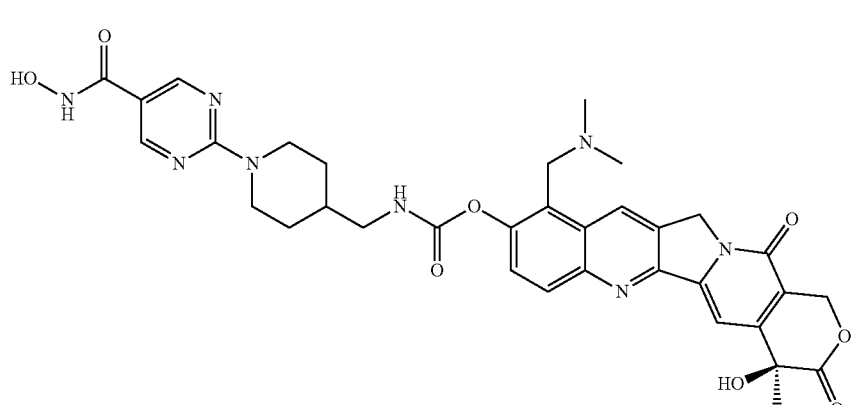 | 699 |

Biological Assays:
(a) Inhibition of Histone Deacetylase Enzymatic Activity

The following assay protocol was used to assay the compounds of the invention against the HDAC enzymes (HDAC-1, 2, 3, 4, 5, 6, 7, 8, 9, 10, and 11.). The buffer used in this assay was 25 mM HEPES, pH 8.0, 137 mM NaCl, 2.7 mM KCl, 1 mM $MgCl_2$ and the substrate was Fluor-de-Lys substrate (Biomol, Cat. # KI-104) in a 50 mM stock solution in DMSO. The enzyme stock solution was 4 μg/mL in buffer. The compounds were pre-incubated (2 μl in DMSO diluted to 13 μl in buffer for transfer to assay plate) with enzyme (20 μl of 4 μg/ml) for 10 minutes at room temperature (35 μl pre-incubation volume). The mixture was pre-incubated for 5 minutes at room temperature. The reaction was started by bringing the temperature to 37° C. and adding 15 μl substrate. Total reaction volume was 50 μl. The reaction was stopped after 20 minutes by addition of 50 μA developer, prepared as directed by Biomol (Fluor-de-Lys developer, Cat. # KI-105). A plate was incubated in the dark for 10 minutes at room temperature before reading ($\lambda_{EX}$=360 nm, $\lambda_{Em}$=470 nm, Cutoff filter at 435 nm). The HDAC inhibitor SAHA was used as reference compound. Such assays, carried out with a range of doses of test compounds, allowed the determination of an approximate IC50 value. Although the inhibitory properties of the compounds of the present invention varied with structural change as expected, the activity generally exhibited by these agents was in the range of $IC_{50}$ 1-1000 nM.

For example, the following table shows the structures of the semisynthetic camptothecin derivative Irinotecan and its rationally designed HDAC-inhibiting derivative CY-700. Both Irinotecan and CY-700 have a camptothecin pharmacophore capable of inhibiting topoisomerase I. The HDAC IC50 values in the table clearly show that CY-700 is a very potent HDAC inhibitor. Therefore, CY-700, as far as we know, represents a First-in-Class dual-functional semisynthetic Camptothecin/HDAC inhibitor simultaneously targeting both topoisomerase pathway and HDAC pathway.

for five minutes in an orbital shaker at 700 rpm. This procedure will lyses the cells and stabilizes the ATP. Next, 50 μL substrate solution was added to the wells and microplate was shaken for five minutes in an orbital shaker at 700 rpm. Finally, the luminescence was measured by a PerkinElmer TopCount® Microplate Scintillation Counter. Such assays, carried out with a range of doses of test compounds, allow the determination of the cellular anti-antiproliferative IC50 of the compounds of the present invention.

The cellular antiproliferative assays were conducted side-by-side for Irinotecan (a FDA approved semisynthetic Camptothecin), and CY-700 (the first-in-class dual-functional semisynthetic Camptothecin/HDAC inhibitor), in 53 different cancer cell lines of breast cancer, renal cancer, non-small cell lung cancer, colon cancer, leukemia, multiple myeloma, ovarian cancer, prostate cancer, melanoma, and CNS cancer. Among these 53 cancer cell lines, the present inventors have pleasantly found that CY-700 has better in vitro potency in 47 cancer cell lines. The following table lists 16 cancer cell lines in which CY-700 is at lease X5 fold more potent than Irinotecan. These results clearly suggest that CY-700 (the first-in-class dual-functional semisynthetic Camptothecin/HDAC inhibitor) has significantly improved anti-cancer activities as compared to the parental Camptothecin drug Irinotecan.

| Cancer | Cell Line | CY-700 (IC50, uM) | Irinotecan (IC50 uM) | Ratio |
|---|---|---|---|---|
| CNS Cancer | SNB-19 | 1.1 | 24.1 | 22.0 |
| Renal Cancer | CAKI-1 | 0.7 | 10.1 | 15.3 |
| Renal Cancer | RXF 393 | 2.3 | 33.6 | 14.7 |
| Breast Cancer | MCF7 | 0.5 | 6.1 | 12.1 |
| Breast Cancer | T-47D | 2.1 | 24.4 | 11.7 |
| Leukemia | CCRF-CEM | 0.4 | 3.5 | 9.7 |
| CNS Cancer | SF-539 | 0.6 | 5.0 | 8.9 |
| Melanoma | SK-MEL-5 | 1.3 | 11.4 | 8.6 |
| Ovarian Cancer | NCI/ADR-RES | 5.1 | 42.2 | 8.2 |

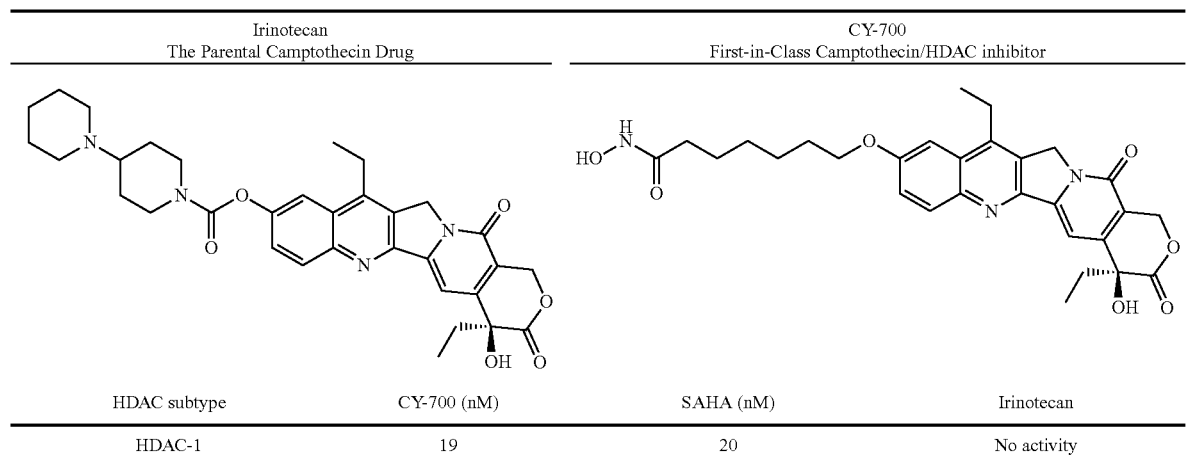

| Irinotecan The Parental Camptothecin Drug | | CY-700 First-in-Class Camptothecin/HDAC inhibitor | |
|---|---|---|---|
| HDAC subtype | CY-700 (nM) | SAHA (nM) | Irinotecan |
| HDAC-1 | 19 | 20 | No activity |

(b) In Vitro Anti-Proliferation Assay:

Cell antiproliferation was assayed by PerkinElmer ATPlite™ Luminescence Assay System. The cancer cell lines were plated at 10 k cells per well in Costar 96-well plates with different concentration of compounds for 72 hours with 5% PBS. After that, one lyophilized substrate solution vial was reconstituted by adding 5 mL of substrate buffer solution and was agitated gently until the solution is homogeneous. 50 μL of mammalian cell lysis solution was added to 100 μL of cell suspension per well of a microplate and the plate was shaken -continued

| Cancer | Cell Line | CY-700 (IC50, uM) | Irinotecan (IC50 uM) | Ratio |
|---|---|---|---|---|
| CNS Cancer | SF-268 | 0.5 | 3.9 | 7.4 |
| NSCLC | NCI-H226 | 1.2 | 8.5 | 7.2 |
| Breast Cancer | BT-549 | 2.6 | 18.5 | 7.0 |
| CNS Cancer | SNB-75 | 2.3 | 15.9 | 6.9 |
| Ovarian Cancer | OVCAR-8 | 2.7 | 17.2 | 6.4 |

| Cancer | Cell Line | CY-700 (IC50, uM) | Irinotecan (IC50 uM) | Ratio |
|---|---|---|---|---|
| CNS Cancer | U251 | 0.7 | 4.1 | 5.5 |
| Melanoma | LOX IMVI | 0.7 | 3.5 | 5.2 |

(c) In Vivo Xenograft Studies:

Since CY-705 has comparable in vitro activities as compared to CY-700 but has significantly better solubility, CY-705 is used in the in vivo studies in the xenograft models of MX-1 (breast cancer), H460 (NSCLC), MBA-MD-435 (melanoma), HCT-116 (colon cancer), HepG2 (liver cancer), Mia-Paca-2 (pancreatic), PC-3 (prostate cancer), and other cancer models. Typically athymic nude mice (CD-1 nu/nu) is obtained at age 6-8 weeks from vendors and acclimated for a minimum 7 day period. The cancer cells are implanted into nude mice, and depending on the tumor type, tumors are typically detectable about two weeks following implantation. When tumor sizes reach ~100-200 mm$^3$, the animals with appreciable tumor size and shape are randomly assigned into groups of 8 mice each, one vehicle control and treatment groups. Dosing varies depending upon the purpose and length of each study, which typically proceeds for 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of <42% are considered significant.

What is claimed is:

1. A compound of Formula I, or a pharmaceutically acceptable salt thereof:

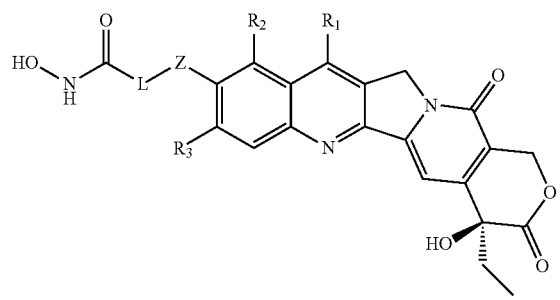

Formula I wherein

Z is deleted, $C(R_aR_b)$, $(CH_2)_p$, $(CH_2)_pNH(CH_2)_q$, CH=N, O, S, C(O), $N(R_a)$, $SO_2$, OC(O), C(O)O, $OSO_2$, $S(O_2)O$, C(O)S, SC(O), C(O)C(O), C(O)N($R_a$), N($R_a$)C(O), $S(O_2)N(R_a)$, $N(R_a)S(O_2)$, OC(O)O, OC(O)S, OC(O)N($R_a$), OC(O)NH(CH$_2$)$_{p+1}$NH (CH$_2$)$_q$, N($R_a$)C(O)O, N($R_a$)C(O)S, or N($R_a$)C(O)N ($R_b$), in which each of $R_a$ and $R_b$, independently, is H, alkyl, alkenyl, or alkynyl; each of p and q, independently, is 0, 1, 2, 3, or 4;

each $R_1$, $R_2$, and $R_3$, independently, is H, alkyl, alkenyl, alkynyl, cycloalkyl, heterocycloalkyl, cycloalkenyl, heterocycloalkenyl, aryl, heteroaryl, halo, nitro, —CH=NH, oxo, cyano, Si($R_cR_cR_c$), alkyl-Si($R_cR_c$ $R_c$), alkyl-$R_c$, alkyl-NR$_c$R$_c$, —CH=NOR$_c$, OR$_c$, OC(O)R$_c$, OC(O)OR$_c$, OC(O)SR$_c$, SR$_c$, C(O)R$_c$, C(O)OR$_c$, C(O)SR$_c$, C(O)NR$_c$R$_c$, SOR$_c$, SO$_2$R$_c$, NR$_c$R$_c$, N(R$_c$)C(O)R$_c$, in which each of R$_c$ independently, is H, alkyl, alkenyl, alkynyl, cycloalkyl, heterocycloalkyl, aryl, heteroaryl, halo, cyano, nitro, amino, hydroxyl, alkylamino, haloalkyl, or alkoxy, or $R_1$, $R_2$, and the atoms to which they are attached are taken together form a ring, which is optionally substituted with R$_c$;

L is —(CH$_2$)$_m$—,

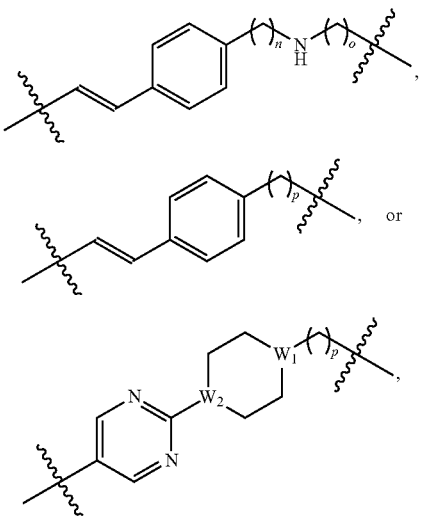

in which m is 5, 6, 7, 8, 9, 10, 11, 12, 13, 14, 15, or 16; each of n and o, independently, is 1, 2, 3, or 4; and each W$_1$ and W$_2$, independently, is CH or N.

2. The compound or salt of claim 1, wherein Z is deleted, (CH$_2$)$_p$, (CH$_2$)$_p$NH(CH$_2$)$_q$, CH=N, O, CO, NH, SO$_2$, OC(O), OSO$_2$, C(O)O, C(O)S, NHC(O), C(O)NH, OC(O) NH, OC(O)NH(CH$_2$)$_{p+1}$NH(CH$_2$)$_q$, OC(O)O, or OC(O)S; m is 5, 6, 7 or 8; and each R$_1$, R$_2$, and R$_3$, independently, is H, alkyl, alkenyl, alkynyl, cycloalkyl, heterocycloalkyl, nitro, oxo, halo, cyano, —CH=NH, Si(R$_c$R$_c$R$_c$), alkyl-Si(R$_c$R$_c$ R$_c$), alkyl-R$_c$, alkyl-NR$_c$R$_c$, CH=NOR$_c$, or NR$_c$R$_c$.

3. The compound or salt of claim 2, wherein Z is O, OC(O), OSO$_2$, OC(O)NH, OC(O)O, OC(O)S, OC(O)NH(CH$_2$)$_{p+1}$NH(CH$_2$)$_q$; m is 6 or 7; R$_3$ is H or F; each R$_c$ independently, is H, alkyl, alkenyl, alkynyl, cycloalkyl, heterocycloalkyl, nitro, amino, hydroxyl, alkylamino, haloalkyl, or alkoxy; and W$_2$ is N.

4. The compound or salt of claim 3, wherein each R$_1$ and R$_2$, independently, is H, alkyl, alkenyl, alkynyl, cycloalkyl, heterocycloalkyl, nitro, Si(R$_c$R$_c$R$_c$), alkyl-SnR$_c$R$_c$R$_c$), alkyl-R$_c$, alkyl-NR$_c$R$_c$, CH=NOR$_c$, or NR$_c$R$_c$.

5. The compound or salt of claim 4, wherein the compound is
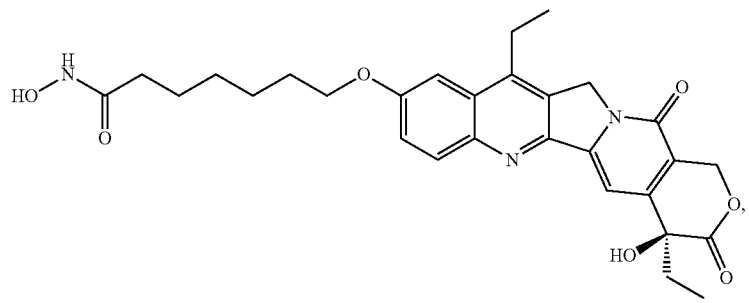
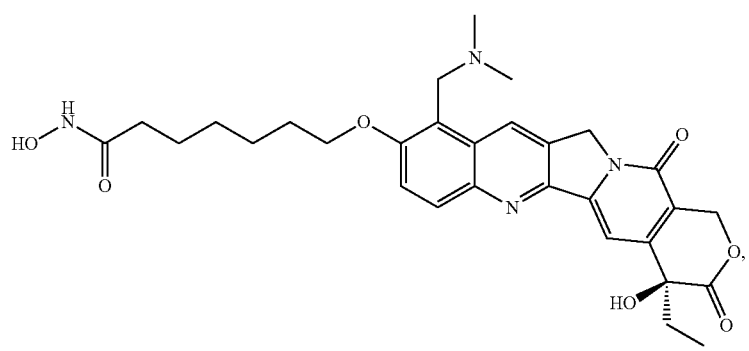
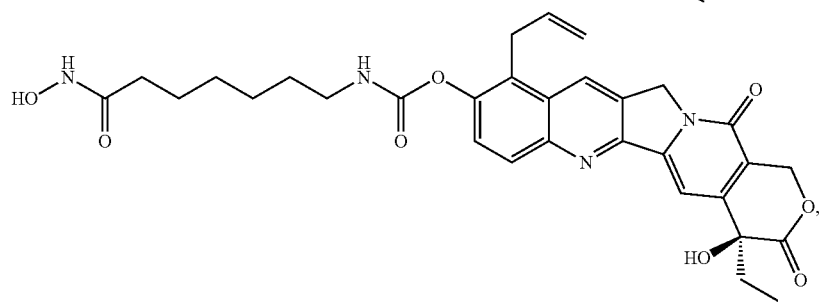
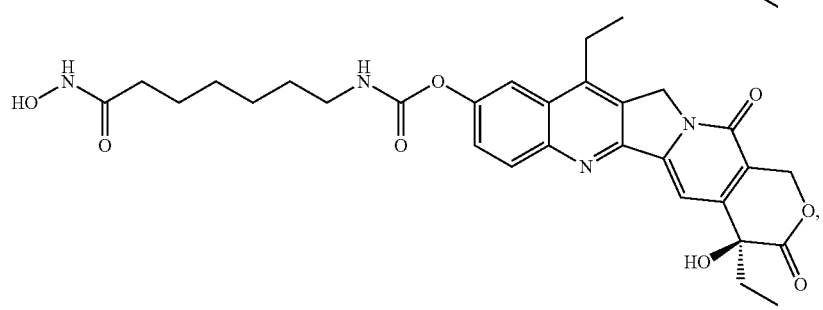
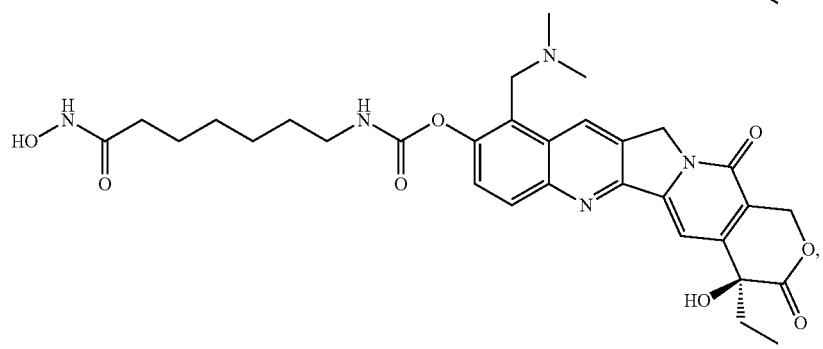

-continued
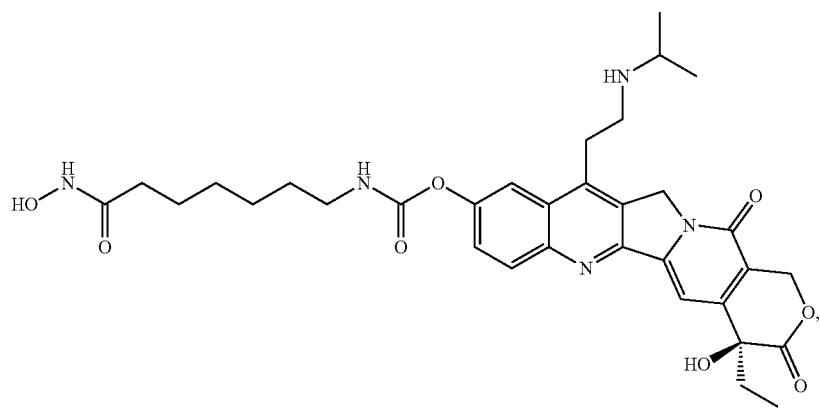
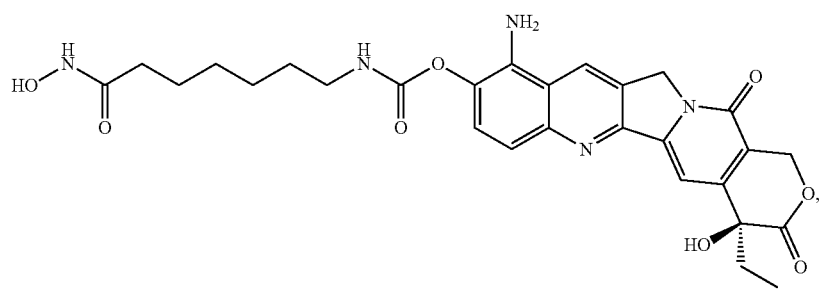
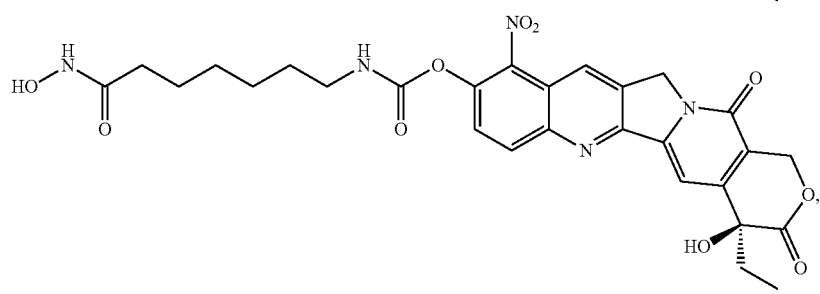
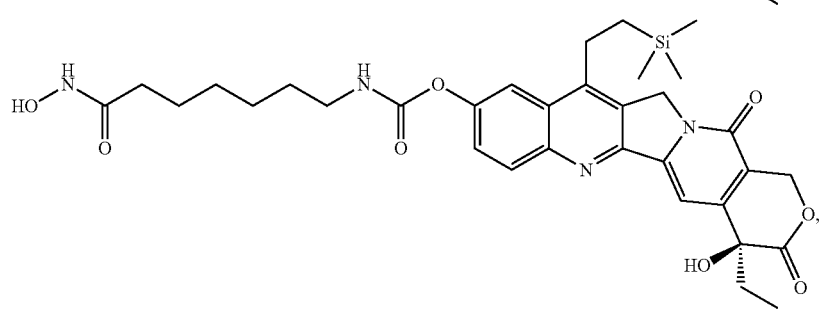
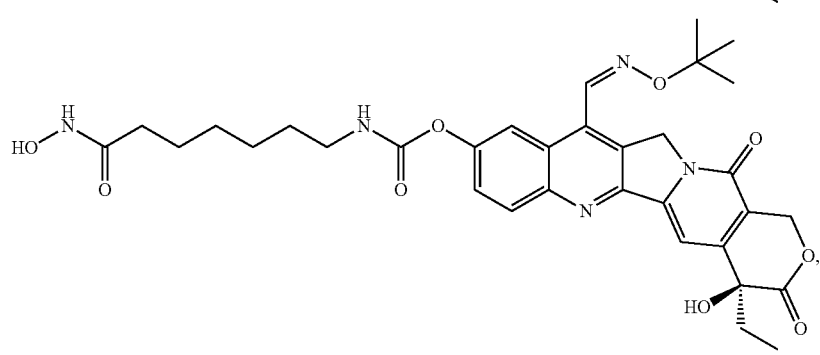

-continued
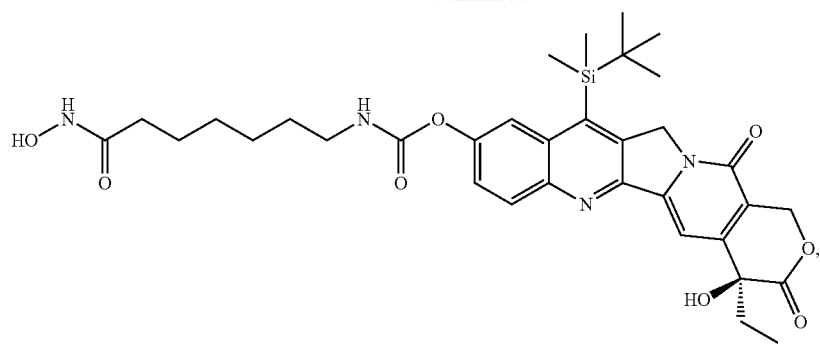
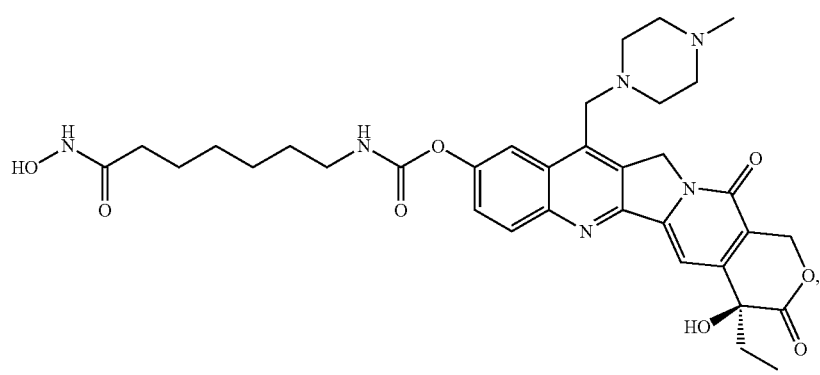
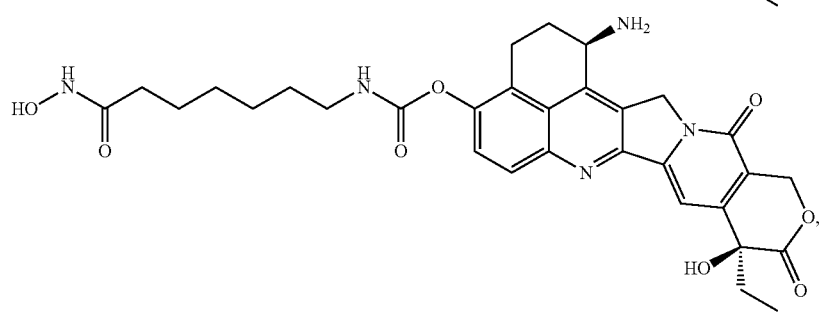
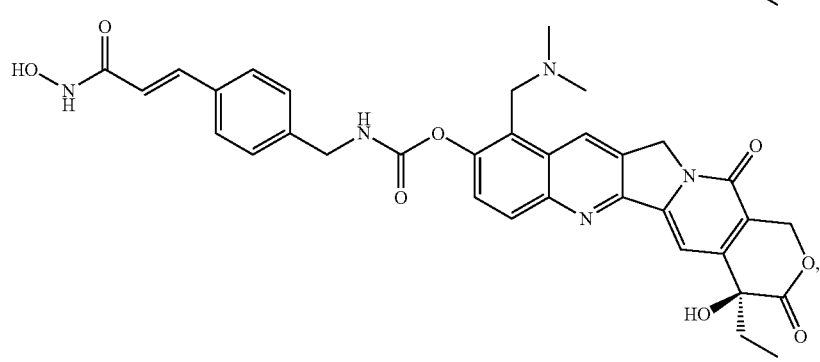
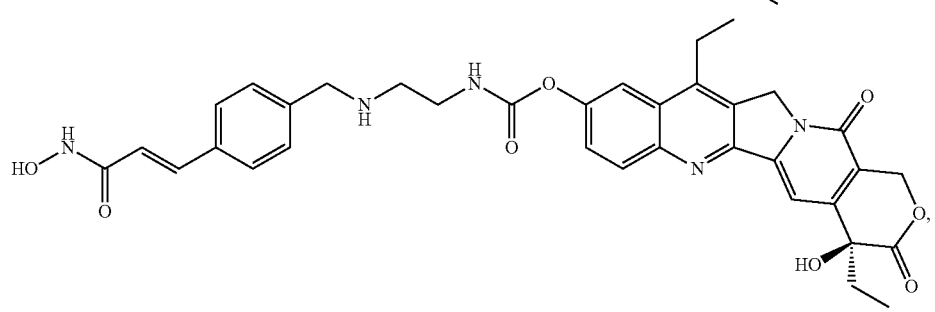

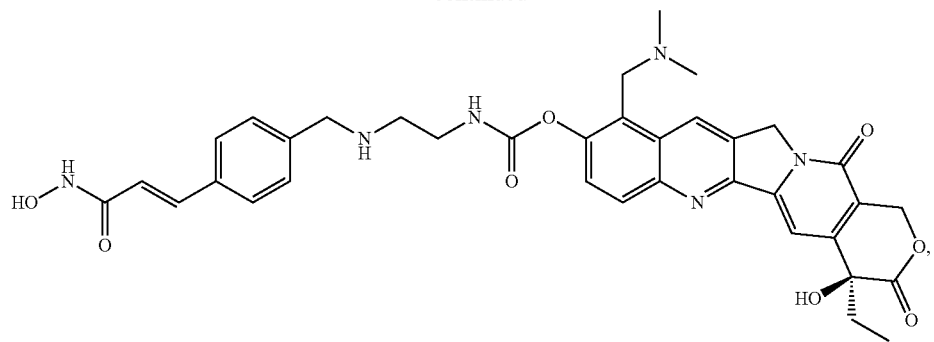
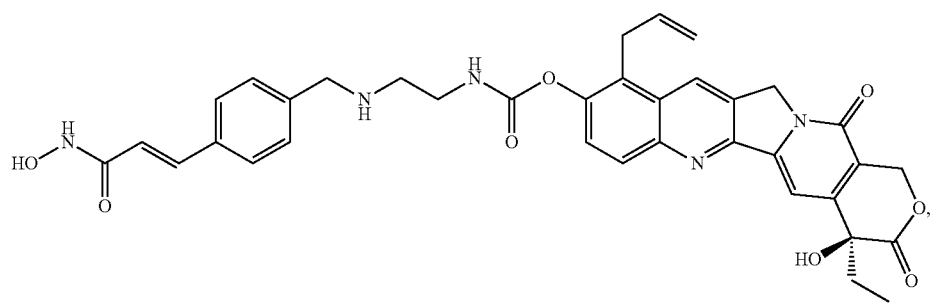
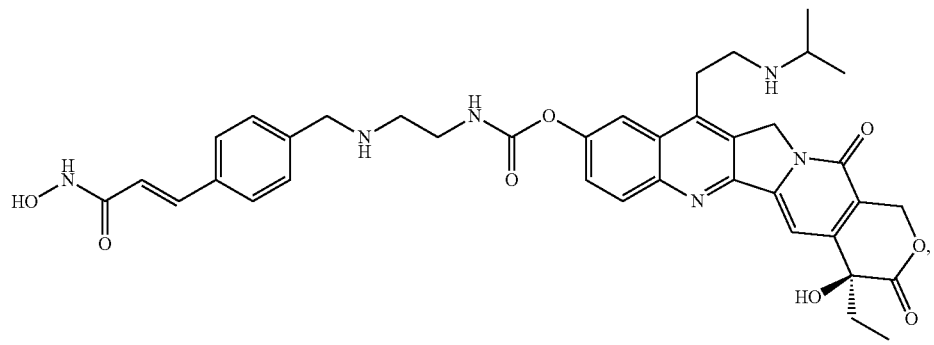
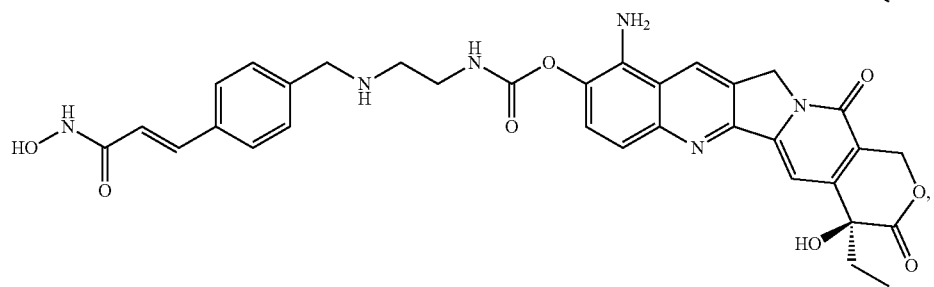
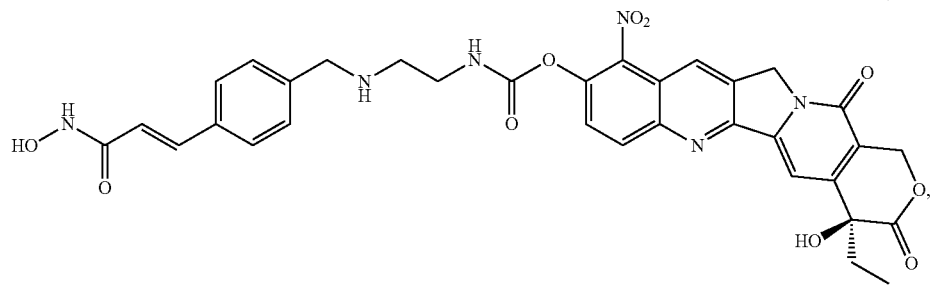

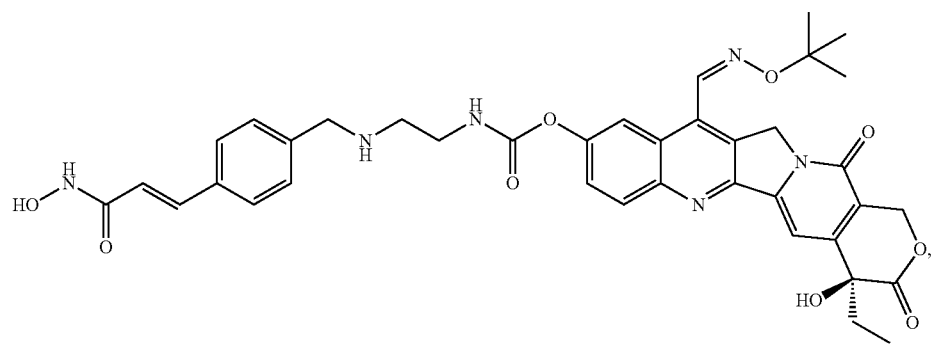
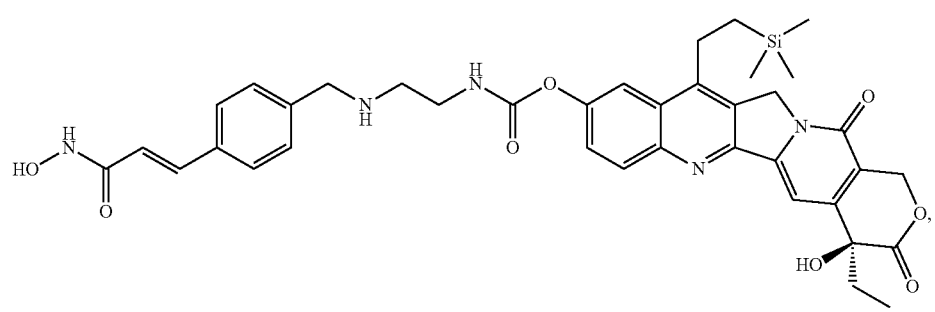
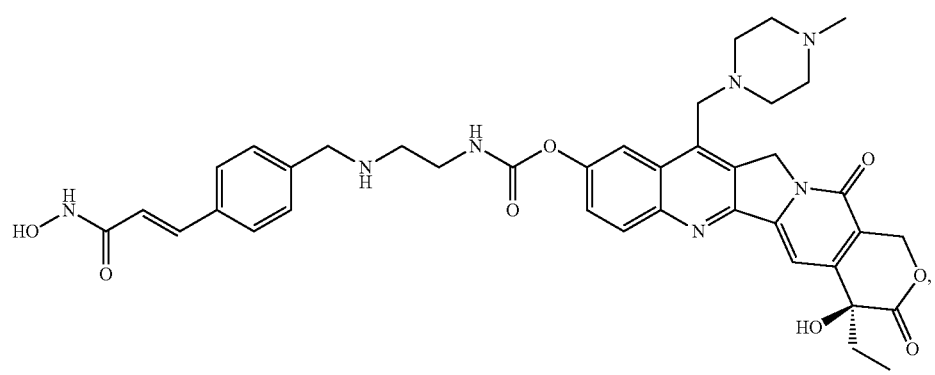
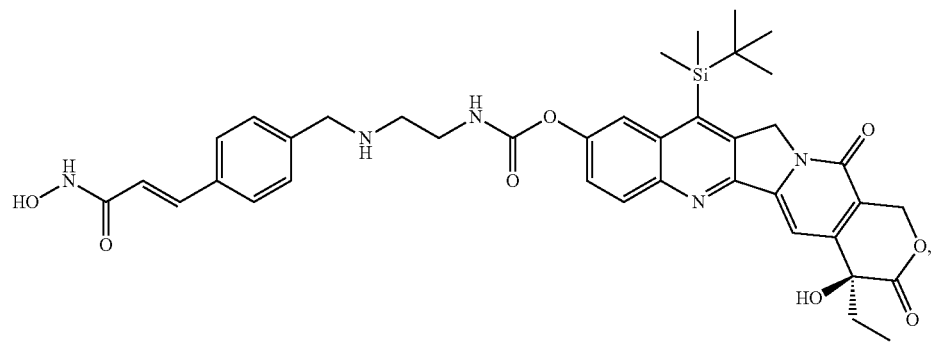

-continued
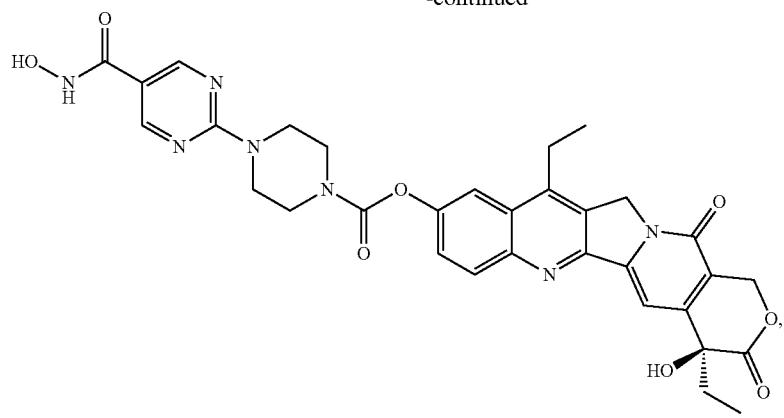
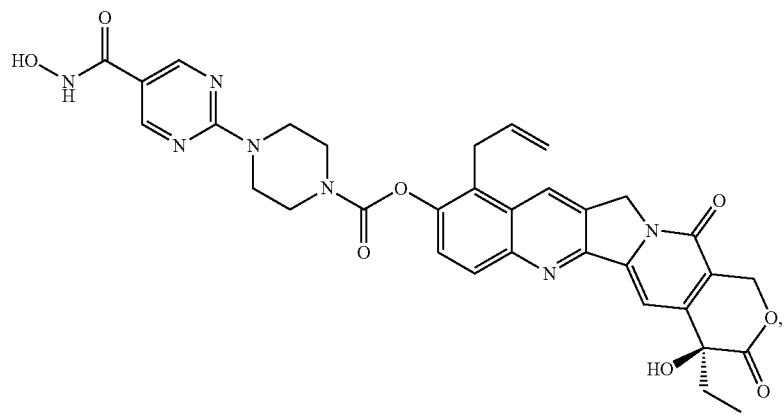
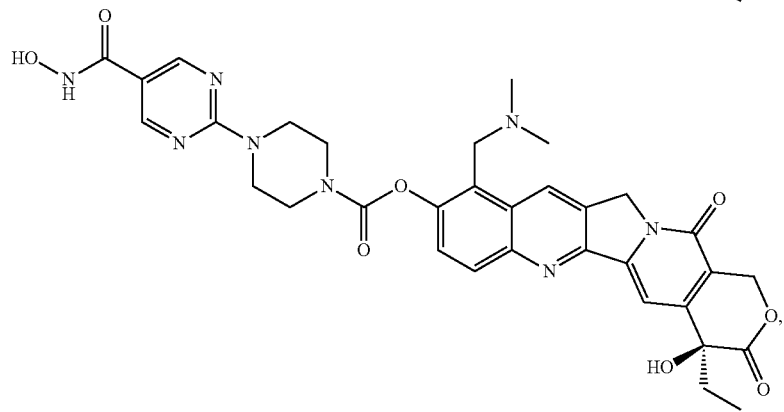
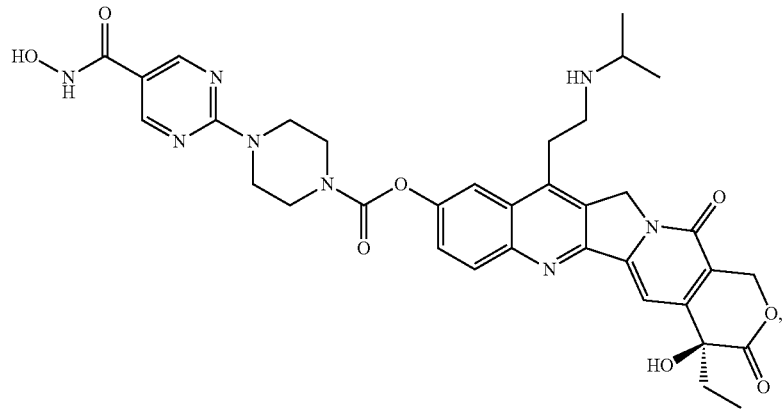

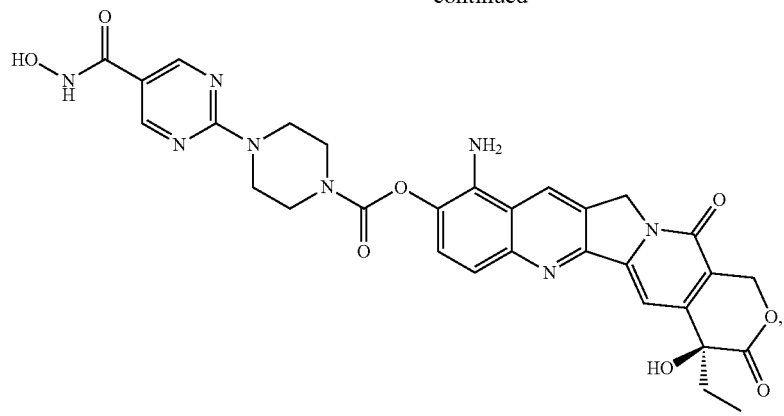
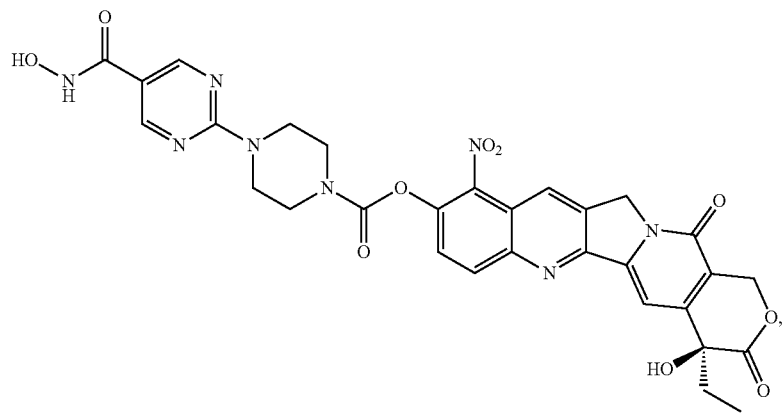
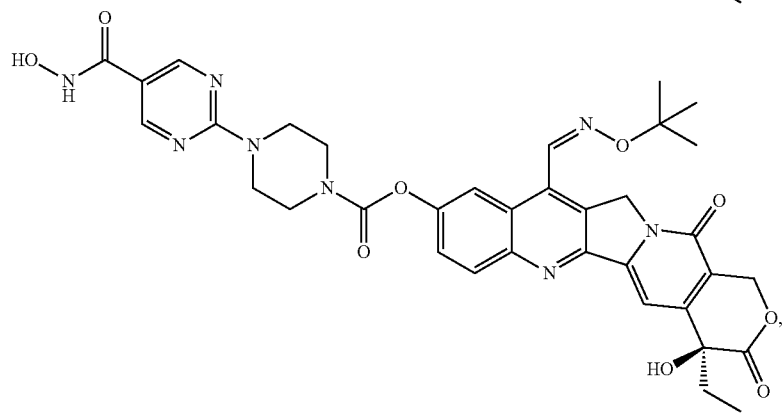
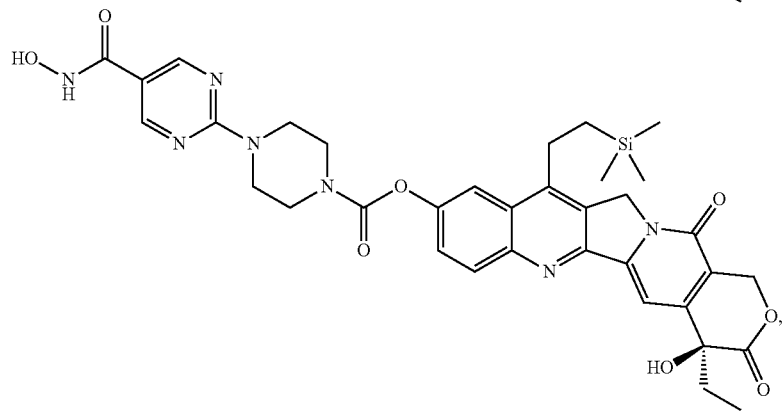

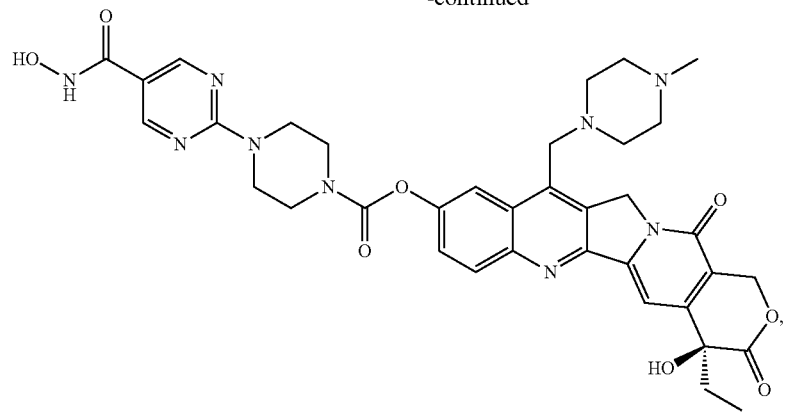
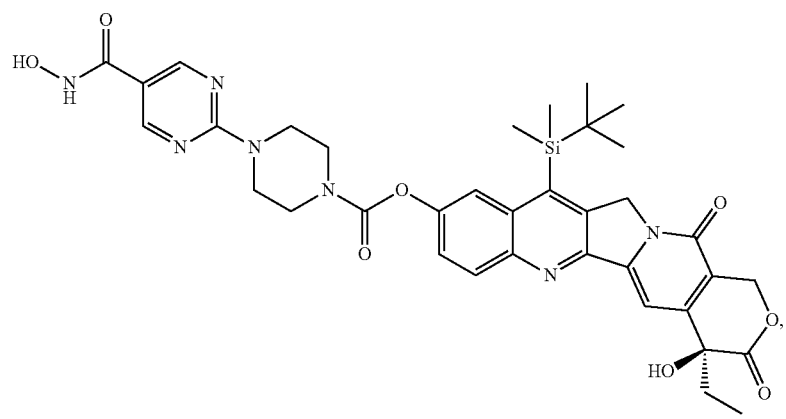
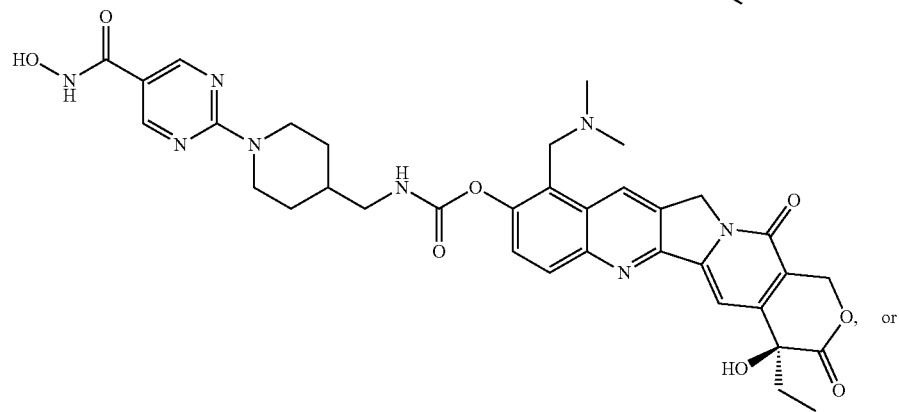
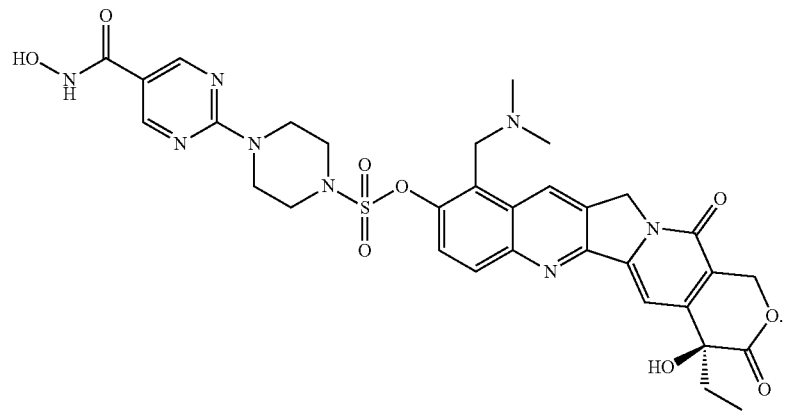

6. The compound or salt of claim 5, wherein the compound is
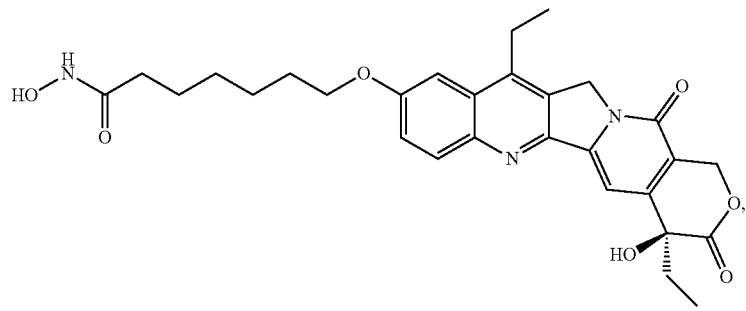 [SMILES: CCc1c2c(nc3ccc(OCCCCCCC(=O)NO)cc13)-c1cc3c(c(=O)n1C2)COC(=O)[C@]3(O)CC]
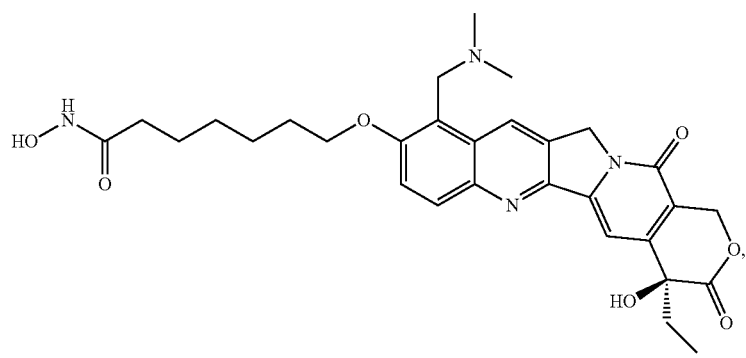
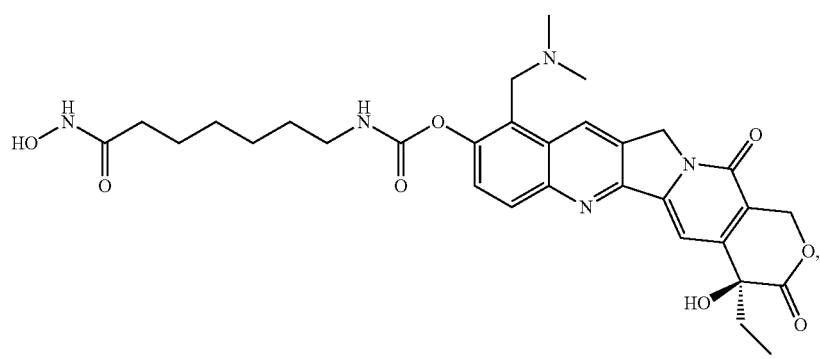
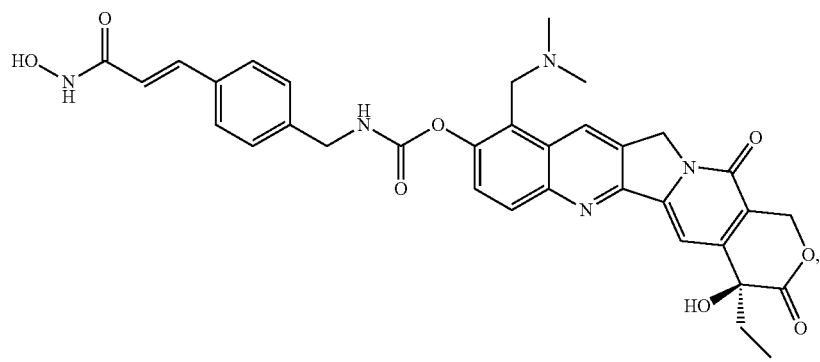

-continued
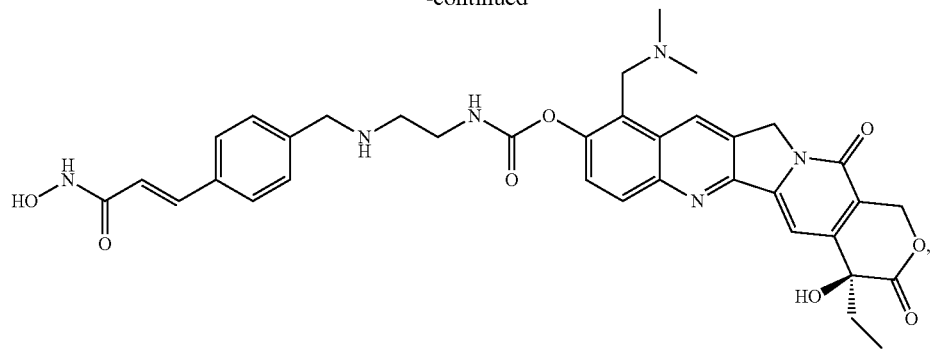
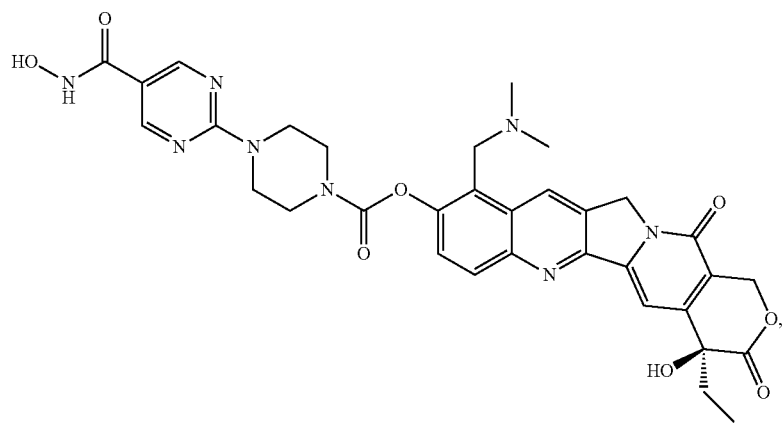
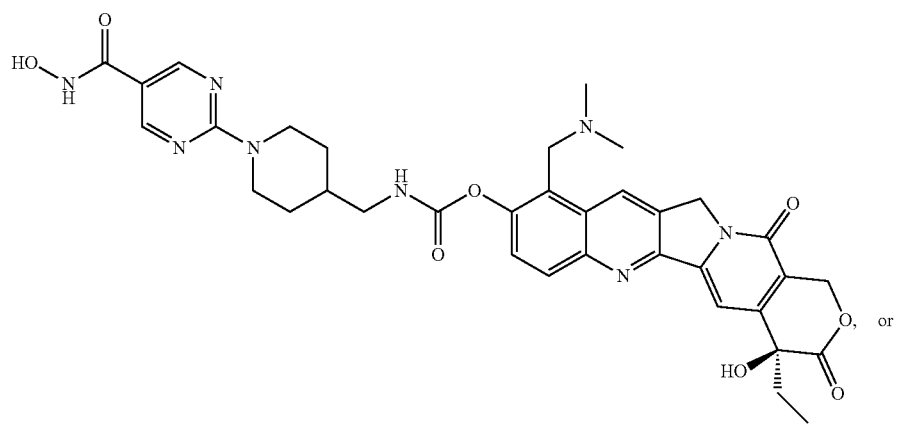
or
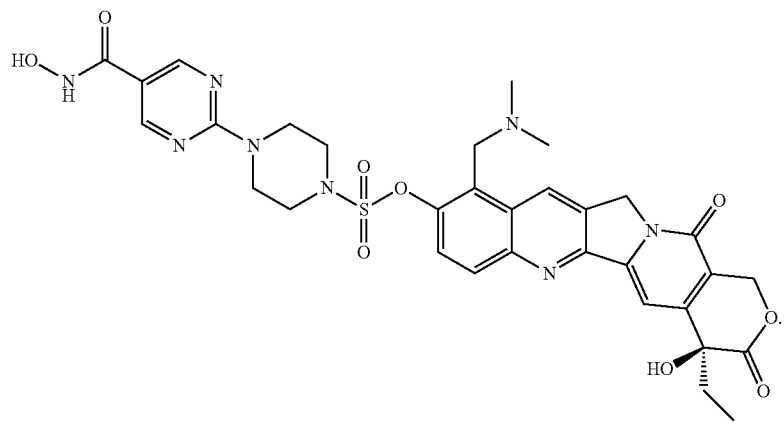

7. The compound or salt of claim 6, wherein the compound is

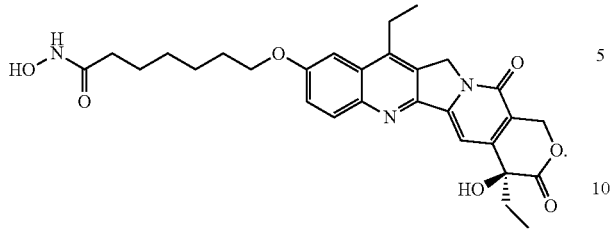

8. The compound or salt of claim 6, wherein the compound is

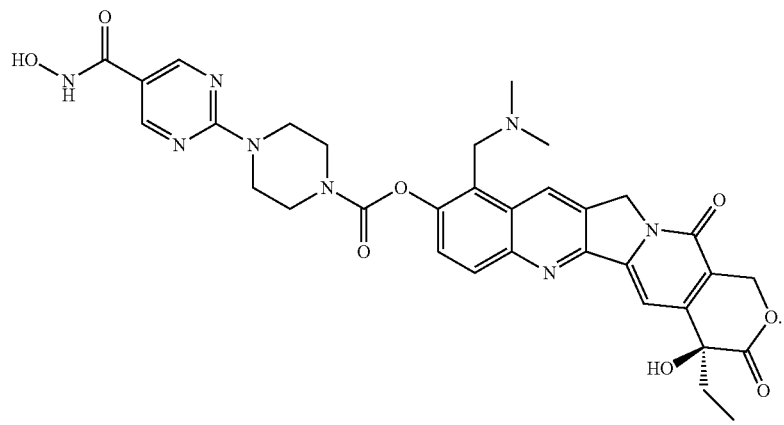 [SMILES: CC[C@@]1(O)C(=O)OCc2c1cc1n(c2=O)Cc2cc3c(CN(C)C)c(OC(=O)N4CCN(c5ncc(C(=O)NO)cn5)CC4)ccc3nc2-1]

9. A modified compound of a compound of claim 1 comprising a modification having improved pharmaceutical solubility, stability, bioavailability, and/or therapeutic index as compared to the unmodified compound.

10. A compound of claim 9, in which said modified compound is a prodrug derivative, a deuterium-enriched compound, a conjugate with a polyethylene glycol, dextran, polyvinyl alcohol, carbohydrate polymer, an antibody, a biomolecule, or mixtures thereof.

11. A pharmaceutical composition comprising a compound or salt of claim 1 and a pharmaceutically acceptable carrier.

12. A method of treating a neoplastic disease or an immune disease, comprising administering to a subject in need thereof an effective amount of a compound or salt of claim 1.

13. An anti-cancer agent simultaneously containing a hydroxamic acid pharmacophore capable of inhibiting histone deacetylases (HDAC) and a pharmacophore capable of inhibiting topoisomerases.

14. An anti-cancer agent of claim 13, wherein said pharmacophore capable of inhibiting topoisomerases is a camptothecin pharmacophore.

15. An anti-cancer agent of claim 13, wherein said topoisomerase is topoisomerase I.

* * * * *